US011896741B2

(12) United States Patent
Rabolt et al.

(10) Patent No.: US 11,896,741 B2
(45) Date of Patent: Feb. 13, 2024

(54) PROCESS FOR PREPARING A POLARIZED FILM OR SHEET CONTAINING β-FORM POLYHYDROXYALKANOATE BASED COPOLYMER

(71) Applicants: John F. Rabolt, Greenville, DE (US); Liang Gong, Newark, DE (US); D. Bruce Chase, Newark, DE (US); Isao Noda, Fairfield, OH (US); Brian Sobieski, Newark, DE (US)

(72) Inventors: John F. Rabolt, Greenville, DE (US); Liang Gong, Newark, DE (US); D. Bruce Chase, Newark, DE (US); Isao Noda, Fairfield, OH (US); Brian Sobieski, Newark, DE (US)

(73) Assignee: UNIVERSITY OF DELAWARE, Newark, DE (US)

( * ) Notice: Subject to any disclaimer, the term of this patent is extended or adjusted under 35 U.S.C. 154(b) by 1151 days.

(21) Appl. No.: 16/578,214

(22) Filed: Sep. 20, 2019

(65) Prior Publication Data

US 2020/0093966 A1   Mar. 26, 2020

Related U.S. Application Data

(60) Provisional application No. 62/734,360, filed on Sep. 21, 2018.

(51) Int. Cl.
*A61L 31/14* (2006.01)
*H10N 30/098* (2023.01)
(Continued)

(52) U.S. Cl.
CPC ............... *A61L 31/14* (2013.01); *A61B 5/01* (2013.01); *A61B 5/0215* (2013.01);
(Continued)

(58) Field of Classification Search
None
See application file for complete search history.

(56) References Cited

U.S. PATENT DOCUMENTS 4,668,449 A   5/1987 Soni et al.
5,602,227 A   2/1997 Noda
(Continued)

FOREIGN PATENT DOCUMENTS

CN   102112873 A   6/2011
CN   108352441 A   7/2018
(Continued)

OTHER PUBLICATIONS

Lotti, Nadia, et al. "Binary blends of microbial poly (3-hydroxybutyrate) with polymethacrylates." Polymer 34.23 (Apr. 6, 1993): 4935-4940. (Year: 1993).*

(Continued)

*Primary Examiner* — Benjamin A Schiffman
(74) *Attorney, Agent, or Firm* — RATNERPRESTIA

(57) ABSTRACT

Disclosed herein is a device comprising a PHA based copolymer layer comprising at least one of an electrospun ribbon of fibers of a polyhydroxyalkanoate based copolymer or the polarized polymeric composition obtained by the process of claim 1, wherein the layer is configured to exhibit one or more of a piezoelectric effect, a pyroelectric effect and a ferroelectric effect, wherein each of the electrospun ribbon of fibers and the polarized polymeric composition comprises a β-form of the PHA based copolymer present in an amount of from about 10% to about 99%, as measured by x-ray diffraction. The device can be configured for use as a sensor, a actuator, a nanomotor, or a biobattery.

13 Claims, 25 Drawing Sheets

(51) Int. Cl.
| | |
|---|---|
| A61B 5/145 | (2006.01) |
| A61B 5/1473 | (2006.01) |
| A61B 5/0215 | (2006.01) |
| A61N 1/375 | (2006.01) |
| C08J 5/00 | (2006.01) |
| A61L 31/06 | (2006.01) |
| A61M 5/142 | (2006.01) |
| A61B 5/00 | (2006.01) |
| A61B 5/01 | (2006.01) |
| D01D 5/00 | (2006.01) |
| D01F 6/84 | (2006.01) |
| H10N 30/20 | (2023.01) |
| H10N 30/045 | (2023.01) |
| H10N 30/30 | (2023.01) |
| H10N 30/857 | (2023.01) |
| H10N 30/00 | (2023.01) |

(52) U.S. Cl.
CPC ........ *A61B 5/1473* (2013.01); *A61B 5/14532* (2013.01); *A61B 5/14546* (2013.01); *A61B 5/6876* (2013.01); *A61L 31/06* (2013.01); *A61M 5/14276* (2013.01); *A61N 1/37512* (2017.08); *C08J 5/00* (2013.01); *D01D 5/003* (2013.01); *D01F 6/84* (2013.01); *H10N 30/045* (2023.02); *H10N 30/098* (2023.02); *H10N 30/1061* (2023.02); *H10N 30/20* (2023.02); *H10N 30/302* (2023.02); *H10N 30/857* (2023.02); *A61B 2562/029* (2013.01); *A61B 2562/12* (2013.01); *A61L 2400/12* (2013.01); *C08J 2367/00* (2013.01)

(56) References Cited

U.S. PATENT DOCUMENTS

| | | | |
|---|---|---|---|
| RE36,584 | E | 2/2000 | Härkönen et al. |
| 8,673,386 | B2 | 3/2014 | Lee et al. |
| 9,897,547 | B2 | 2/2018 | Rabolt et al. |
| 2003/0232122 | A1 | 12/2003 | Chappa et al. |
| 2010/0068460 | A1 | 3/2010 | Moriyama et al. |
| 2012/0025674 | A1 | 2/2012 | Yoshida et al. |
| 2012/0055257 | A1 | 3/2012 | Shaw-Klein |
| 2014/0145365 | A1 | 5/2014 | Omenetto et al. |
| 2017/0258585 | A1 | 9/2017 | Marquez et al. |
| 2019/0068108 | A1 | 2/2019 | Guhathakurta et al. |

FOREIGN PATENT DOCUMENTS

| | | | |
|---|---|---|---|
| JP | 2006106592 | A | 4/2006 |
| JP | 2014502416 | A | 1/2014 |
| JP | 2016102152 | A | 6/2016 |
| WO | 2010104196 | A1 | 9/2010 |

OTHER PUBLICATIONS

Murakami, Rumi, et al. "Formation and stability of β-structure in biodegradable ultra-high-molecular-weight poly (3-hydroxybutyrate) by infrared, Raman, and quantum chemical calculation studies." Polymer 48.9 (Mar. 3, 2007): 2672-2680. (Year: 2007).*
Gong, Liang, et al. "Discovery of β-form crystal structure in electrospun poly [(R)-3-hydroxybutyrate-co-(R)-3-hydroxyhexanoate](PHBHx) nanofibers: From fiber mats to single fibers." Macromolecules 48.17 (Aug. 18, 2015): 6197-6205. (Year: 2015).*
Broodhurst et al., "Piezo- and Pyroelectric Properties," Electrets, 1987, vol. 33, pp. 285-319.
Gong et al., "Polymorphic Distribution in Individual Electrospun Poly[(R)-3-Hydroxybutyrate-co-(R)-3-Hydroxyhexanoate] (PHBHX) Nanofibers," Macromolecules, 2017, vol. 50, pp. 5510-5517.
Gong et al., "Discovery of β-Form Crystal Structure in Electrospun Poly[(R)-3-Hydroxybutyrate-co-(R)-3-Hydroxyhexanoate] (PHBHX) Nanofibers: From Fiber Mats to Single Fibers, Macromolecules," 2015, vol. 48, pp. 6192-6205.
Sobieski, "Characterization of a Bio-Based, Biodegradable Class of Copolymers, Poly[(R)-3-Hydroxybutyrate-co-(R)-3-Hydroxyhexanoate], and Application Development," Dissertation submitted to the University of Delaware, 2017, 310 pages.
Sobieski et al., "Thermally Reversible Physical Gels of Poly [(R)-3-Hydroxybutyrate-co-(R)-3-Hydroxyhexanoate]: Part 1 Gelation in Dimethylformadide", Polymer, vol. 131, pp. 217-223.
Gong, L., "Discovery of the β-form Crystal Structure in Electrospun Nanofibers of Bio-Based Poly [(R)-3-Hydroxybutyrate-co-(R)-3-Hydroxyhexanoate] and its Implications on Properties," Dissertation submitted to the University of Delaware, 2017, 164 pages.
Kakade et al., "Electric Field Induced Orientation of Polymer Chains in Macroscopically Aligned Electrospun Polymer Fibers," Journal of the American Chemical Society, vol. 129(10), Feb. 16, 2007, pp. 2777-2782.
Australian Examination Report No. 2 for Australian Application No. 2019344010, dated Feb. 1, 2022, 8 pages.
Australian Examination Report No. 3 for Australian Application No. 2019344010, dated Feb. 28, 2022, 8 pages.
Australian Examination Report No. 4 for Australian Application No. 2019344010, dated Oct. 19, 2022, 9 pages.
Australian Examination Report No. 5 for Australian Application No. 2019344010, dated Dec. 12, 2022, 7 pages.
Australian Notice of Acceptance for Australian Application No. 2019344010, dated Dec. 21, 2022, 4 pages.
Singapore Written Opinion for Singapore Application No. 11202101878Q, dated Apr. 19, 2022, 6 pages.
Extended European Search Report for European Application No. 19862485.0, dated May 11, 2022, 8 pages.
Chinese Office Action for Chinese Application No. 20198006220.X dated Oct. 17, 2022 with translation, 14 pages.
Japanese Notice of Reasons for Refusal for Japanese Application No. 2021-515560, dated Jul. 20, 2023 with translation, 4 pages.
European Communication pursuant to Article 94(3) for European Application No. 19 862 485.0, dated Aug. 2, 2023, 4 pages.
Korean Request for the Submission of an Opinion for Korean Application No. 10-2021-7009803, dated Jul. 19, 2023 with translation, 19 pages.

* cited by examiner

PROCESS FOR PREPARING A POLARIZED FILM OR SHEET CONTAINING β-FORM POLYHYDROXYALKANOATE BASED COPOLYMER

CROSS-REFERENCE TO RELATED APPLICATION

This application claims priority to U.S. Provisional Patent Application No. 62/734,360, filed Sep. 21, 2018, the entire disclosure of which is incorporated herein by reference for all purposes.

STATEMENT REGARDING FEDERALLY SPONSORED RESEARCH

This invention was made with government support under Grant No. 130176 awarded by the Delaware NSF EPSCoR and Grant No. 1407255 awarded by the National Science Foundation through DMR Polymers program. The government has certain rights in the invention.

BACKGROUND OF THE INVENTION

Piezoelectricity, a Greek-derived term for pressure electricity, describes the ability of certain materials to generate electrical charge when subjected to mechanical stress (direct piezoelectric effect), or to expand or contract when placed in an electrical field (indirect converse piezoelectric effect). The piezoelectric, effect is recognized as the electromechanical interaction between the mechanical and electrical states in materials that lack inversion symmetry. The nature of the piezoelectric effect is strongly related to the existence of electrical dipole moments in solids, which may either be induced for ions at crystal lattice sites with asymmetric charge surroundings, or carried directly by molecular groups. When subjected to mechanical deformation, piezoelectric materials will exhibit a potential difference between the surfaces due to a change of dipole moments. This potential difference, or voltage, causes electrical charges to be driven around a circuit (current) and thus create electricity. Among all piezoelectric materials, piezoelectric polymers have attracted special attention over the last two decades because of their structural and dimensional flexibility, light weight, ease of processing, large sensitive area and relatively low cost implementation.

Polyhydroxyalkanoates (PHAs) are a class of biodegradable and biocompatible aliphatic polyesters synthesized by a variety of bacteria as intracellular carbon and energy storage materials. They have attracted scientific attention for their promising environmental, electrical, pharmaceutical, and biomedical applications. Among PHAs, poly(3-hydroxybutyrate) (PHB) homopolymer is the most common type and has been extensively studied over the past 30 years. However, due to the near perfect stereoregularity, bacterially produced PHB has very high crystallinity (>60%) and a melt temperature range (ca. 180° C.) near its thermal decomposition temperature. The constraint of the difficult-to-process thermal properties and rigid, and brittle nature of the material are major obstacles to most standard applications. Copolymerization with other small monomer units, such as 3-hydroxyvalerate (3HV), was attempted with relatively little success in improving the properties. This surprising result arises from the fact that 3HB and 3HV units are isodimorphous, with 3HV units being incorporated into the PHB crystalline lattice. Recently, in order to substantially enhance the properties of PHB, a small amount of hydroxyalkanoic acid monomers with longer side chains, such as 3-hydroxyhexanoate (3HHx), was copolymerized with 3HB units to avoid the isodimorphism and reduce the rigidity and brittleness of the resultant copolymer. These medium chain length (mcl) branches act as molecular defects, disrupting the excessive regularity of the polymer chain and consequently lowering the crystallinity and melting point (Tm). The resultant random copolymer, poly[(R)-3-hydroxybutyrate-co-(R)-3-hydroxyhexanoate] (PHBHx), becomes soft and flexible as the 3HHx content increases and results in properties similar to linear low-density polyethylene (LLDPE). Many properties of PHBHx, including chemical, thermal, and mechanical properties, can be adjusted by changing the comonomer content.

It has been established that PHB and poly[(R)-3-hydroxybutyrate-co-(R)-3-hydroxyvalerate] (PHBV, a PHB based random copolymer) can exhibit two different crystalline polymorphs, the α-form and β-form, depending on processing conditions. The α-form is the most common crystal structure of the PHB or PHBV polymers obtained from typical crystallization processes, such as melt or solution crystallization. In this crystal polymorph, the molecular chains adopt a left handed $2_1$ helical conformation. The unit cell is orthorhombic with a space group of $P2_12_12_1$-$D_2$ and lattice parameters of a=0.576 nm, b=1,320 nm, and c (fiber period)=0.596 nm. The other crystal polymorph, the β-form crystal, is recognized as a strain-induced paracrystalline structure with highly extended chains. In the β-form, the chains adopt a twisted planar zigzag conformation, which is a nearly fully extended chain conformation. The unit cell is also orthorhombic with lattice parameters of a=0,528 nm, b=0.920 nm, and c (fiber period)=0.470 nm. This metastable crystal structure, which can be annealed back to the α-form at 130° C., was first observed in hot-drawn PHB thin films and later was found in cold-drawn PHBV thin films. In particular, this β-form was found in a cold-drawn amorphous film, indicating that the generation of the β-form does not require prior alignment of the α-form crystals. Over the following 10 years, the metastable β-form has been successfully generated in thin films or melt-spun fibers of PHB and PHBV under different post processing conditions, where the films or fibers were highly stretched, although the draw ratios may vary. It is reported that the β-form remained relatively unchanged for months at room temperature, suggesting that this crystal structure does not undergo secondary crystallization.

The β-structure has long been accepted to originate from the orientation of the free chains in the amorphous phase between the α-form lamellar crystals. When experiencing high stretching forces, the tie molecules between the lamellar crystals will be strongly extended and orient along the stretching direction. As long as the free chains adopt a planar zigzag conformation, they would pack and form the β-structure. The generation of the β-form crystal structure has a large effect on various properties of the material, including the mechanical properties, biodegradability, and piezoelectric response.

Electrospinning is an effective and versatile technique, utilizing electrostatic forces to draw the solutions or melts of many different macromolecular systems to produce nanofibers (10 nm to 5 μm). Such fibers find applications in areas including composites, tissue engineering, energy storage and conversion, sensors, and filtration systems. Efforts have been made to elucidate the strong electrically driven stretching forces during the electrospinning process. The total draw ratio is estimated to be as high as 25000. In addition, one can introduce additional stretching forces on the fibers during fiber deposition by using modified collectors, such as rotating collectors (rotary drum, rotary disk, etc.) and gapped collectors (two charged metallic rods or plates separated by an insulated gap), eventually obtaining macroscopically aligned fibers along the roll-up direction or across the gap. These strong stretching forces, together with extremely rapid solvent evaporation, have been observed to induce formation of metastable phases or crystalline polymorphs. Therefore, electrospinning was explored as a processing technique to induce the metastable β-structure in PHA nanofibers. The β-structure was found in PHB nanofibers electrospun from dilute polymer solutions via conventional electrospinning techniques. Later, this metastable crystal structure was observed in the electrospun PHBV fibers collected on a rotary drum. The existence of the β-form in electrospun PHBHx was first reported in Gong, Liang, et al. "Discovery of β-form crystal structure in electrospun poly [(R)-3-hydroxybutyrate-co-(R)-3-hydroxyhexanoate] (PHBHx) nanofibers: from fiber mats to single fibers," Macromolecules 48, 17 (2015): 6197-6205 and Gong, Liang, et al, "Polymorphic Distribution in Individual Electrospun Poly [(R)-3-hydroxybutyrate-co-(R)-3-hydroxyhexanoate] (PHBHx) Nanofibers." *Macromolecules* 50, 14 (2017): 5510-5517.

There remains a desire in the art to develop applications for making, optimizing, and using β-form PHBHx in various implementations.

SUMMARY OF THE INVENTION

Disclosed herein for the first time are sensors comprising successfully produced materials comprising bin-based and biodegradable poly(hydroxyalkanoate) copolymers (PHAs) of 3-hydroxybutyrate and other 3-hydroxyalkanoate units with medium-chain-length (mcl) branches, such as poly[(R)-3-hydroxybutyrate-co-(R)-3-hydroxyalkanoate], which have a surprisingly high content of beta-form crystalline structure with the extended chains adopting a planar zig-zag conformation verified by wide angle X-ray diffraction (WAXD) analysis. Additionally, these materials comprising high content of beta-form crystal exhibits unexpectedly high level of piezoelectricity, pyroelectricity and ferroelectricity. Hence, these materials can be used for fabricating devices such as, actuators, sensors, and the like. Furthermore, materials comprising mcl-branched PHAs have substantial advantages over conventional PHAs because of the superior properties better suited for many end-use applications and much easier processability. This beta-form crystalline structure was produced under select and very specific conditions, in accordance with various embodiments of the present invention. The process method may include highly aligned electrospinning PHA nanofiber fabrication techniques involving an air-gap receiving electrode or a sharp edge high speed rotary disc fiber collection, drawing of very thin films, shearing of thin films between two glass slides, electrospraying of thin films, high-pressure annealing, nano fibril formation within thermoreversible gels, as well as high-pressure or high-temperature treatment.

Also disclosed herein are strain-induced metastable β-form crystal structure, with the extended chains adopting a planar zigzag conformation, in the macroscopically aligned electrospun nanofibers of poly[(R)-3-hydroxybutyrate-co-(R)-3-hydroxyhexanoate] (PHBHx) collected across the air gap on aluminum foil and on the tapered edge of a high-speed rotary disk. The presence of the β-form crystal structure in the fiber mats was confirmed by wide-angle X-ray diffraction (WAXD) and Fourier transform infrared spectroscopy (FUR). In addition, selected area electron diffraction (SAED) and AFM-IR were utilized to investigate the morphological and structural details of individual electrospun nanofibers. The SAED results confirmed a significant influence of the collection method on the crystal structure as well as the orientation level of the molecular chains in the crystals. The AFM-IR spectra of the single nanofibers matched well with the traditional FTIR spectra, but the finer features in the AFM-IR spectra were more distinct and better resolved. Based on the experimental results, new mechanisms for the generation of the β-form crystalline structure in electrospun PHBHx nanofibers are proposed.

In an embodiment, the β-form of PHBHx also displays pyroelectric and ferroelectric properties In an aspect of the present invention, there is a polymeric blend displaying at least one of piezoelectric, pyroelectric or ferroelectric property, wherein the polymer blend is for a use in a device, such as sensors and actuators etc. In an embodiment, the polymer blend is a Wend of one or more PHBHx copolymers, each one or more PHBHx copolymers having a different comonomer content. For example, the polymer blend may include a blend of PHBHx3.9 with PHBHx13.0 as an example of piezoelectric blends. In another embodiment, the polymer blend is a polymer blend of PHBHx with a compositionally different polymer. For example, the polymer blend may include, but is not limited to a polymer blend of PHBHx with poly(vinylidene fluoride) (PVF2) and its copolymers and/or Nylon 5, Nylon 7, Nylon 9, Nylon 11 etc.

Also disclosed herein are PHAs with longer side chains, such as pentyl, heptyl, etc., including but not limited to, Nodax™ class of PHA.

In general, PHA copolymers of the present invention preferably have a β-form present in the range of from about 10% to about 99% as measured via x-ray diffraction; more preferably from about 20% to about 80%; more preferably still from about 30% to about 70%, based on X-ray diffraction analysis.

In an aspect, one of the following methods may be used for making a PHA copolymer based piezoelectric material:
   Fibers produced by electrospinning process (currently known best method)
   Films or sheets subjected to high shear, such as calendar rolling
   Films or sheets made by crystallizing melt under shear or pressure
   Gels dried under pressure of shear
   Gels frozen to induce shear by the crystallization of the solvents
   Molded articles processed under shear or pressure
   Articles made from melt under electrical fields (poling)
   Other Processing Methods to increase Piezoelectric PHBHx include extrusion (e.g., as in a twin-screw extruder), injection molding, and traditional fiber spinning Disclosed herein is a single electrospun polymer nano fiber comprising a heterogeneous spatial distribution of crystalline polymorphs. Two crystalline polymorphs of PHBHx, the thermodynamically stable α-form consisting of chains with a $2_1$ helical conformation and the metastable β-form consisting of chains with a planar zigzag conformation, are spatially distributed as a core-shell structure composed of an α-form-rich core and a β-form-rich shell. In addition, it was found that the thickness of the shell is independent of the fiber diameter. The characterization of crystalline polymorphic distribution in individual nanofibers has been made possible by utilizing a technique combining atomic force microscopy (AFM) and infrared spectroscopy (IR), which simultaneously provides the nanoscale spatial resolution and crystalline phase specificity. Based on the experimental results, a possible generation mechanism of this polymorphic heterogeneous core-shell structure is proposed. The implications of this core-shell model on fiber properties are also discussed.

Disclosed herein are piezoelectric electrospun PHBHx nanofibers with crystalline regions exhibiting the β-form crystalline structure associated with chains of highly oriented planar zig-zag conformation. The piezoelectric properties of the aligned PHBHx nanofibers, were investigated as a function of varying crystal structure. The results indicated a strong correlation between the piezoelectric response of the fibers and the presence of the β-form crystal structure. The mechanisms for the development of piezoelectric response of the fibers will be proposed, and the sensitivity of the piezoelectric PHBHx nanofibers to pressure was also quantified.

Disclosed herein is a method of formation of the conformation in PHBHx films through stress induced beta crystallization, where the stress is applied by mechanical stretching the film.

Disclosed herein is a method of forming the β conformation in PHBHx films via a novel method of room temperature isothermal crystallization followed by mechanical stretching. It was confirmed that a crystallites must be present prior to formation of the β conformation. The ideal conditions to initially form the β conformation corresponded to 28 minutes of isothermal crystallization. Additionally, this β conformation was shown to be reversible and that the stretching process is different for the initial β formation and the re-stretching process. The β conformation could also be annealed back into the α conformation at temperatures as low as 48° C.

In an aspect, there is a process for preparing a polarized polymeric composition comprising the steps of:
  a) providing a layer of a polarizable polymeric composition, wherein the polarizable polymeric composition comprises a polyhydroxyalkanoate based copolymer;
  b) directionally perturbing the layer to induce polarization;
  c) optionally polarizing the polymeric composition of the directionally perturbed layer by applying a high electric field which is of less intensity than that which would cause substantial dielectric breakdown of the one or more polymers; and
  d) optionally annealing the polarized polymeric composition of the layer at a temperature less than the melting temperature of the crystals of the polarized polymeric composition, whereby the polarization is retained up to the crystal melting point of the polar crystals of the polymeric composition,
  wherein the polarized polymeric composition comprises a β-form of the PHA based copolymer, present it an amount of from about 10% to about 99%, as measured by x-ray diffraction.

In an embodiment of the process, the step of providing layer comprises electrospinning a ribbon of fibers from a solution of the polyhydroxyalkanoate based copolymer in one or more solvents, wherein the each fiber of the electrospun ribbon of fibers comprises a shell formed of β-form and a core formed of α-form.

In an embodiment of the process, the step of providing a layer comprises forming a layer from a solution of the polyhydroxyalkanoate based copolymer in one or more solvents.

In another embodiment of the process, the step of providing a layer comprises forming a layer from a melted composition of the polyhydroxyalkanoate based copolymer and the step of directionally perturbing the layer comprises calendar rolling, shearing or cold drawing the layer after quenching.

In an embodiment of the process, the step of providing a layer comprises forming a film from a gel composition of the polyhydroxyalkanoate based copolymer and the step of directionally perturbing the film comprises drying gel under shear pressure or freezing gel to induce shear by crystallization of solvent.

In an embodiment of the process, the step of providing a layer comprises forming an electrospun fiber mat from a solution of polyhydroxyalkanoate based copolymer in one or more solvents.

In an embodiment, the polyhydroxyalkanoate based copolymer comprises at least one monomer unit selected from the group consisting of hydroxybutyrate units, hydroxyhexanoate units, vinyl units, vinylidene units, ethylene units, acrylate units, methacrylate units, Nylon units, carbonate units, acrylonitrile units, cellulose units, units having pendant fluoro, chloro, amide, ester other than ester of acrylate and methacrylate units, cyanide, nitrile other than of acrylonitrile units, or ether groups, protein units and combinations thereof.

In another embodiment, the polarizable polymeric composition further comprises one or more polymers selected from the group consisting of polyvinylchloride, polymethylacrylate, polymethylmethacrylate, poly(vinylidene cyanide/vinyl acetate) copolymers, vinylidene cyanide/vinyl benzoate copolymers, vinylidene cyanide/isobutylene copolymers, vinylidene cyanide/methyl methacrylate copolymers, vinylidene fluoride copolymer, polyvinylfluoride, polyacrylonitrile, polycarbonate, cellulose, proteins, synthetic polyesters and ethers of cellulose, poly(gamma-methyl-L-glutamate), vinylidene copolymers, Nylon-3, Nylon-5, Nylon-7, Nylon-9, Nylon-11 and blends thereof.

In an aspect of the process, the layer comprises at least two layers of the polarizable polymeric composition formed from a multiphase composition of said polymer composition. In an embodiment, the at least two layers are co-extruded and are in contact with one another.

In an embodiment of the process, the step optionally polarizing the polymeric composition of the directionally perturbed layer is conducted using an electric field of, at least 1 MV/cm at a temperature from about 20° C. to about 120° C. for up to about 5 hours. In another embodiment, the layer is annealed at a temperature in the range of from about 125° C. to about 150° C. for at least one hour.

In an aspect of the present invention, there is a device comprising at least one of an electrospun fiber mat of a polyhydroxyalkanoate based copolymer or the polarized polymeric composition obtained by the process of claim 1, wherein the device is configured to exhibit one or more of a piezoelectric effect, a pyroelectric effect and a ferroelectric effect.

In an embodiment of the device, the device further comprises two or more layers of polarized polymeric composition, wherein the two or more layers are in the form of a ribbon of fibers stacked together In an aspect, the device is a sensor configured to produce a potential difference or voltage in response to a change in dimension of the layer of polarized polymeric composition. In an embodiment, the change in dimension is caused by a change in one or more of the following properties, humidity, temperature, salinity, nutrient attachment or infusion and metalloid attachment at a surface of the sensor layer of the polarized polymeric composition.

In another aspect of the device, the sensor comprises a plurality of sensor surfaces and/or interfaces, wherein each surface/interface is independently configured to monitor one of the following properties, humidity, temperature, salinity, nutrient attachment or infusion and metalloid attachment.

In an aspect, the device is an actuator configured to expand or contract in response to an application of an electrical charge across the layer of the polarized polymeric composition.

In an aspect, there is a nanomotor comprising one or more piezoelectric actuators as described hereinabove.

In another aspect, there is a device comprising one or more actuators as disclosed hereinabove, configured for placement or implantation near a vascular system component of an animal or a human patient and configured to produce a change in dimension of the PHA based copolymer layer due to heartbeats of the animal or the human patient to generate a potential difference or voltage to operate a monitoring or treatment device. In an embodiment, the treatment or monitoring device comprises a pacemaker, insulin pump, in-situ glucose monitor, or blood pressure monitor. In another embodiment, the vascular system component comprises a vein or artery that beats in a cadence corresponding to heart beats of the patient.

In an aspect, there is a method comprising the step of providing a PHA based copolymer sensor layer configured to monitor one of the following properties, humidity, temperature, salinity, nutrient attachment or infusion and metalloid, attachment, wherein the PHA based copolymer sensor layer comprises at least one of electrospun ribbon of fibers of a polyhydroxyalkanoate based copolymer or the polarized polymeric composition obtained by the process as disclosed hereinabove. The method further comprises exposing a PHA based copolymer sensor layer to one or more of the said properties, such that the PHA based copolymer sensor layer undergo a change in dimension caused by a change in one or more of the said properties, and detecting a potential difference or voltage in response to a change in dimension of the PHA based copolymer sensor layer

BRIEF DESCRIPTION OF THE DRAWINGS

FIG. 56: Schematic of the SAED Patterns of Single Fibers Collected with Different Methods and Central Angles of the Arc Reflections of the Indexed Crystalline Planes.

DETAILED DESCRIPTION OF THE INVENTION

Figure 1:
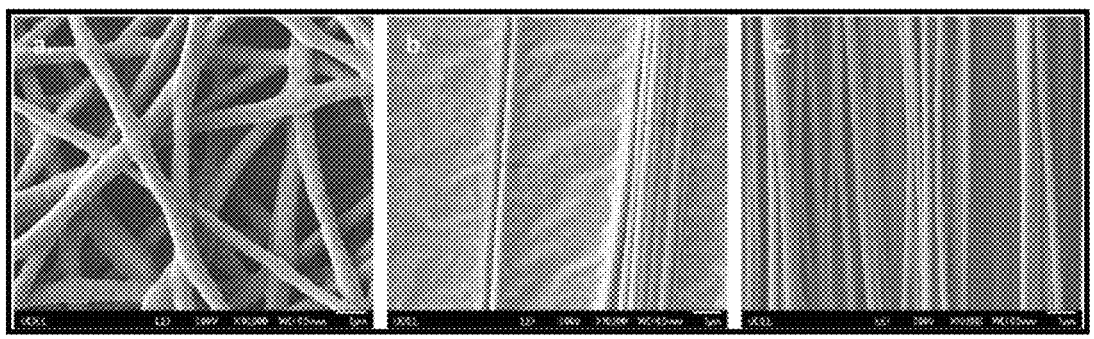
FIG. 1: SEM images of electrospun PHBHx fibers collected (a) on the aluminum foil off the air gap, (b) across the air gap, and (c) on the rotary disk.

As used herein, "PHA" means a polyhydroxyalkanoate of the present invention. As used herein, "PHB" means the homopolymer poly-(3-hydroxybutyrate). As used herein, "PHBV" means the copolymer poly(3-hydroxybutyrate-co-3-hydroxyvalerate). As used herein, "PHBHx" means the copolymer Poly[(R)-3-hydroxybutyrate-co-(R)-3-hydroxyhexanoate], wherein x represents the amount as mol % of the comonomer hydroxyhexanoate (Hx) present in the copolymer.

In an embodiment, the PHBHx copolymer is produced by the chiral ring opening polymerization of optically Pure 3HB and ³HHx [R] configuration comonomers. In another embodiment, the PHBHx copolymer is biologically produced bio-based isotactic PHBHx.

β-Form Crystal Structure in Electro spun Poly[(R)-3-hydroxybutyrate-co-(R)-3-hydroxyhexanoate] (PHBHx) Nanofibers: from Fiber Mats to Single Fibers Disclosed herein are the β crystalline polymorph macroscopically aligned electrospun PHBHx nanofibers obtained using two modified collectors, i.e., an aluminum foil with a rectangular air gap and a rotary disk with a tapered edge. For fiber mats, the fiber morphology, crystal structure, and chain conformation were characterized by scanning electron microscopy (SEM), wide-angle X-ray diffraction (WAXD), and transmission Fourier transform infrared spectroscopy (FTIR). In addition, the structure and orientation within PHBHx nanofibers at the single fiber scale were investigated with the aid of selected area electron diffraction (SAED) and AFM-IR. Example 1 disclosed hereinbelow provides an exemplary method of forming β-Form Crystal Structure in Electrospun Poly[(R)-3-hydroxybutyrate-co-(R)-3-hydroxyhexanoate] (PHBHx) Nanofibers including experimental procedures and results.

Piezoelectricity in Electrospun Poly[(R)-3-hydroxybutyrate-co-(R)-3-hydroxyhexanoate] (PHBHx) Nanofibers According to Broadhurst and Davis (Broadhurst, M. G., and G. T. Davis, "Piezo- and pyroelectric properties." Electrets, Springer, Berlin, Heidelberg, 1980, 285-319), there exist four critical elements for all piezoelectric polymers: (1) the occurrence of permanent molecular dipoles; (2) the ability to align the molecular dipoles; (3) the ability to sustain this dipole alignment once it is achieved; and (4) the ability of the material to undergo large strains when mechanically stressed. Electrospun PHBHx nanofiber meet all these criteria because (1) O=C—CH2 dipoles exist in the material; (2) the rapid and extensive stretching during electrospinning orients the molecular chains along the fiber axis, and thus aligns the molecular dipoles; (3) the fast solvent evaporation during electrospinning facilitates the preservation of dipole alignment through fiber solidification; and (4) the flexible fibers can withstand large deformations.

In an aspect, piezoelectric response of electrospun PHBHx nanofibers as a function of crystal structure or structures present in the fibers is disclosed herein. Macroscopically aligned PHBHx nanofibers containing the metastable β-form crystalline structure were fabricated using a high-speed rotary disk as the collector. A control sample was made by annealing these fibers at 130° C. for 24 hours, so that the annealed fibers contained only the α-crystalline form. The piezoelectric properties of the aligned fibers, both before and after annealing, were characterized utilizing a piezoelectric cantilever. The mechanisms for the development of piezoelectric response of the fibers are proposed and the sensitivity of the piezoelectric PHBHx nanofibers to pressure was quantified. Example 3 disclosed herein below provides an exemplary method of measuring piezoelectric effect in electrospun PHBHx nanofibers.

In an embodiment, the β-form of PHBHx also displays pyroelectric and ferroelectric properties.

Polarizable Copolymers and Polymer Blends Displaying at Least One of a Piezoelectric, a Pyroelectric or a Ferroelectric Property In an aspect, there is a polyhydroxyalkanoate (PHA) copolymer comprising a polarizable polymer unit selected from the group consisting of hydroxybutyrate units, hydroxyhexanoate units, vinyl units, vinylidene units, ethylene units, acrylate units, methacrylate units, Nylon units, carbonate units, acrylonitrile units, cellulose units, units having pendant fluoro, chloro, amide, ester other than ester of acrylate and methacrylate units, cyanide, nitrite other than of acrylonitrile units, or ether groups, protein units and combinations thereof.

In another aspect, there is a piezoelectric copolymer selected from the group consisting of poly(hydroxybutyrate/hydroxyhexanoate), poly(vinylidene fluoride/trifluoroethylene), poly(vinylidene fluoride/tetrafluoromethylene), poly(vinylidene fluoride/vinyl trifluoride), poly(vinylidene fluoride/vinyl chloride) and poly(vinylidene fluoride/methylmethacrylate).

The comonomer may be present in the polyhydroxyalkanoate copolymer in any suitable molar amount, including up to 1%, 2%, 3%, 5%, 10%, 15%, 20%, 25%, 30%, 35% or in the range of 2-30% or 3-25% or 5-20%. In an embodiment, the comonomer unit hydroxyhexanoate is present in the poly(hydroxybutyrate/hydroxyhexanoate) in any suitable molar amount, including up to 1%, 2%, 3%, 5%, 10%, 15%, 20%, 25%, 30%, 35%.

In yet another aspect, there is a polarizable polymeric composition comprising one or more polymers selected from the group consisting of polyvinylchloride, polymethylacrylate, polymethylmethacrylate, poly(vinylidene cyanide/vinyl acetate) copolymers, vinylidene cyanide/vinyl benzoate copolymers, vinylidene cyanide/isobutylene copolymers, vinylidene cyanide/methyl methacrylate copolymers, polyvinylfluoride, polyacrylonitrile, poly-carbonate, cellulose, proteins, synthetic polyesters and ethers of cellulose, and poly(gamma-methyl-L-glutamate).

In an embodiment, the polarizable polymeric composition comprises one or more polymers selected from the group consisting of poly(vinylidene fluoride) and vinylidene fluoride copolymer. In another embodiment, the polarizable polymeric composition comprises one or more copolymers selected from the group consisting of poly(hydroxybutyrate/hydroxyhexanoate), poly(vinylidene fluoride/trifluoroethylene), poly(vinylidene fluoride/tetrafluoroethylene), poly(vinylidene fluoride/vinyl trifluoride), poly(vinylidene fluoride/vinyl chloride) and poly(vinylidene fluoride/methylmethacrylate). In yet another embodiment, the polarizable polymeric composition comprises one or more polymers selected from the group consisting of soluble ceramic materials, PHBHx, poly(vinylidene fluoride), vinylidene copolymers, Nylon-3, Nylon-5, Nylon-7 Nylon-9 and Nylon-11 and blends thereof.

In an aspect of the present invention, the polarizable polymeric composition is a polymeric blend displaying at least one of piezoelectric, pyroelectric or ferroelectric property, wherein the polymer blend is for a use in a device, such as sensors and actuators etc. In an embodiment, the polymer blend is a blend of one or more PHBHx copolymers, each one or more PHBHx copolymers having a different comonomer content. For example, the polymer blend may include a blend of PHBHx3.9 with PHBHx13.0 as an example of piezoelectric blends. In another embodiment, the polymer blend is a polymer blend of PHBHx with a compositionally different polymer. For example, the polymer blend may include, but is not limited to a polymer blend of PHBHx with poly(vinylidene fluoride) (PVF2) and its copolymers and/or Nylon 5, Nylon 7, Nylon 9, Nylon 11 etc.

In another aspect of the present invention, the polarizable polymeric composition is a PHA with longer side chains, such as pentyl, heptyl, etc. In an embodiment, the polarizable polymeric composition is a polymer blend of PHBHx and one or more PHAs with longer side chains. In another embodiment, the polarizable polymeric composition is a copolymer of PHBHx and one or more PHAs with longer side chains. Exemplary PHAs with longer side chains include but are not limited to, PHBO with pentyl side groups, PHBD with heptyl side group, and the like with side group as as C15 side group chains, the Nodax™ class of medium-chain-length branched polyhydroxyalkanoates, mcl-PHA, available from Danimer Scientific. For a list beyond PHBHx, see U.S. Pat. No. 5,602,227 and RE 36,584, which is incorporated herein by reference.

In an embodiment, the polarizable polymeric composition is a blend of PHBHx, poly(vinylidene fluoride) and vinylidene fluoride-vinyl fluoride (80/20) copolymer. In another embodiment, there is a 50:50 by weight blend of PHBHx and vinylidene fluoride-vinyl fluoride (80/20) copolymer. In yet another embodiment, there is a 50:50 by weight blend of PHBHx and poly(vinylidene fluoride).

β-Form in PHA Copolymers and Blends of PHA Copolymers

In general PHA copolymers and blends of PHA copolymers of the present invention preferably have a β-form present in the range of from about 10% to about 99% as measured via x-ray diffraction; more preferably from about 20% to about 80%; more preferably still from about 30% to about 70% based on X-ray diffraction analysis.

Process of Making PHA Copolymer Based Piezoelectric Materials Comprising PHAs Under Directional Perturbations Any suitable method may be used for remaking a PHA copolymer based piezoelectric material, including, but not limited to:

Fibers produced by electrospinning process (currently known best method).

Films or sheets subjected to high shear, such as calendar rolling, Example 5 disclosed herein below provides an exemplary method for the production of, beta form of PHBHx copolymer based films by mechanical stretching.

Films or sheets made by crystallizing melt under shear or pressure, Example 4 disclosed herein below provides an exemplary method stress-induced beta crystallization of PHBHx copolymer based films.

Gels dried under pressure of shear. Example 6 disclosed hereinbelow provides an exemplary method for the production of beta form of PHBHx copolymer based gel films by mechanical stretching.

Gels frozen to induce shear by the crystallization of the solvents.

Molded articles processed under shear or pressure.

Articles made from melt under electrical fields.

Other Processing Methods to increase Piezoelectric PHBHx include extrusion (e.g., as in a in-screw extrude). Injection molding and traditional fiber spinning.

In an aspect, there is a process for preparing a polarized polymeric composition comprising the steps of a) providing a layer of a polarizable polymeric composition, wherein the polarizable polymeric composition comprises a polyhydroxyalkanoate based copolymer;

b) directionally perturbing the layer to induce polarization;

c) optionally polarizing the polymeric composition of the directionally perturbed layer by applying a high electric field which is of less intensity than that which would cause substantial dielectric breakdown of the one or more polymers; and d) optionally annealing the polarized polymeric composition of the layer at a temperature less than the melting temperature of the crystals of the polarized polymeric composition, whereby the polarization is retained up to the crystal melting point of the polar crystals of the polymeric composition, wherein the polarized polymeric composition comprises a β-form of the PHA based copolymer, present in an amount of from about 10% to about 99%, as measured by x-ray diffraction.

In an embodiment of the process, the step of providing a layer comprises electrospinning a ribbon of fibers from a solution of the polyhydroxyalkanoate (PHA) based copolymer in one or more solvents, wherein the each fiber of the electrospun ribbon of fibers comprises a shell formed of β-form and a core formed of α-form. In an embodiment, a dilute solution, such as upto 1 wt % or upto 2 wt % or upto 5 wt % of the PHA based copolymer in a suitable solvent, such as 1,1,1,3,3,3-hexafluoro-2-propanol (HFIP) can use used for electrospinning using an experimental set up such as disclosed hereinbelow in Example 1.

In an embodiment of the process, the step of providing a layer comprises forming a layer from a solution of the polyhydroxyalkanoate based copolymer in one or more solvents. The polyhydroxyalkanoate based copolymer may be present in an amount of from 1-99% or 5-90% or 0-80%, based on the total weight of the solution. Any suitable solvent may be used, including but not limited to, chloroform, toluene, acetone, and the like. The layer can be formed using any suitable method such as, casting.

In another embodiment of the process, the step of providing a layer comprises forming a layer from a melted composition of the polyhydroxyalkanoate based copolymer and the step of directionally perturbing the layer comprises calendar rolling, shearing or cold drawing the layer after quenching.

In an embodiment of the process, the step of providing a layer comprises forming a film from a gel composition of the polyhydroxyalkanoate based copolymer and the step of directionally perturbing the film comprises drying gel under shear pressure or freezing gel to induce shear by crystallization of solvent. The gel composition of the polyhydroxyalkanoate based copolymer can be formed by any suitable method, such as disclosed hereinbelow in Example 6.

In an embodiment of the process, the polyhydroxyalkanoate based copolymer comprises at least one monomer unit selected from the group consisting of hydroxybutyrate units, hydroxyhexanoate units, vinyl units, vinylidene units, ethylene units, acrylate units, methacrylate units, Nylon units, carbonate units, acrylonitrile units, cellulose units, units having pendant fluoro, chloro, amide, ester other than ester of acrylate and methacrylate units, cyanide, nitrile other than of acrylonitrile units, or ether groups, protein units and combinations thereof.

In another embodiment of the process, the polarizable polymeric composition further comprises one or more polymers selected from the group consisting of polyvinylchloride, polymethylacrylate, polymethylmethacrylate, poly(vinylidene cyanide/vinyl acetate) copolymers, vinylidene cyanide/vinyl benzoate copolymers, vinylidene cyanide/isobutylene copolymers, vinylidene cyanide/methyl methacrylate copolymers, vinylidene fluoride copolymer, polyvinylfluoride, polyacrylonitrile, polycarbonate, cellulose, proteins, synthetic polyesters and ethers of cellulose, poly (gamma-methyl-L-glutamate), vinylidene copolymers, Nylon-3, Nylon-5, Nylon-7, Nylon-9, Nylon-11 and blends thereof.

In an aspect of the process, the layer comprises at least two layers of the polarizable polymeric composition formed from a multiphase composition of said polymer composition. In an embodiment, the at least two layers are co-extruded and are in contact with one another.

In an embodiment of the process, the step optionally polarizing the polymeric composition of the directionally perturbed layer is conducted using an electric field of at least 1 MV/cm at a temperature from about 20° C. to about 120° C. for up to about 5 hours. In one embodiment, the layer is annealed at a temperature in the range of from about 125° C. to about 150° C. for at least one hour.

In an embodiment, the polarized polymeric composition is a polarized poly(hydroxybutyrate-co-hydroxyhexanoate) (PHBHx) copolymer in which the polarization is essentially stable to about the crystal melting range of its polar crystals. In another embodiment, the polarized polymeric composition is a polarized Poly(hydroxybutyrate)/poly(vinylidene fluoride) copolymer.

In an embodiment, the polarized polymeric composition is a blend of a polarized polyhydroxyalkanoate (PHA) based copolymer and a copolymer selected from the group consisting of poly(hydroxybutyrate/hydroxyhexanoate), poly (vinylidene fluoride/trifluoroethylene), poly(vinylidene fluoride/tetrafluoroethylene), poly(vinylidene fluoride/vinyl trifluoride), poly(vinylidene fluoride/vinyl chloride) and poly(vinylidene fluoride/methylmethacrylate). In another embodiment, the polarized polymeric composition is a blend of PHBHx copolymer and one or more components selected from the group consisting of soluble ceramic materials, poly(vinylidene fluoride), vinylidene copolymers, Nylon-3, Nylon-5, Nylon-7, and Nylon-11. In an embodiment, the polarized polymeric composition comprises 50:50 by weight of each of Nylon-7 and Nylon-11 and the polarized PHA based copolymer. The polarized PHA based copolymer may be present in the blend in any suitable amount, such as 1-99% or 5-90% or 10-80%, based on the total weight of the blend composition.

In an embodiment, the polarized polymeric composition is a blend of poly(vinylidene fluoride) and vinylidene fluoride-vinyl fluoride (80/20) copolymer. In another embodiment, the polarized polymeric composition comprises a 50:50 by weight blend of PHBHx and vinylidene fluoride-vinyl fluoride (80/20) copolymer. In another embodiment, the polarized polymeric composition comprises a 50:50 by weight blend of PHBHx and poly(vinylidene fluoride).

In an aspect of the present invention, there is a device comprising at least one of an electrospun fiber of a polyhydroxyalkanoate based copolymer or the polarized polymeric composition obtained by the process of claim 1, wherein the device is configured to exhibit one or more of a piezoelectric effect, a pyroelectric effect and a ferroelectric effect. In an embodiment, the layer of the polarized polymeric composition is a self-supporting sheet of polarized polymeric composition is a self-supporting sheet. In another embodiment, the layer of the polarized polymeric composition is a non-self-supporting layer of said composition disposed on a support substrate.

In an embodiment of the device, the device further comprises two or more layers of polarized polymeric composition, wherein the two or more layers are in the form of a ribbon of fibers stacked together In an aspect, the device is a sensor configured to produce a voltage in, response to a change in dimension of the layer of polarized polymeric composition.

In another aspect, the device is a universal a sensor configured to produce a potential difference or voltage in response to a change in dimension caused by a change in one or more of the following properties, humidity, temperature, salinity, nutrient attachment or infusion and metalloid attachment at a surface of the sensor layer of the polarized polymeric composition.

In another aspect of the device, the sensor comprises a plurality of sensor surfaces and/or interfaces, wherein each surface/interface is independently configured to monitor one of the following properties, humidity, temperature, salinity, nutrient attachment or infusion and metalloid attachment.

In an aspect, the device is an actuator configured to expand or contract in response to an application of an electrical charge across the layer of the polarized polymeric composition.

In an aspect, there is a nanomotor comprising one or more piezoelectric actuators as described hereinabove.

Also discussed herein below is an example of fabrication method for so-called poled polymeric article, electrets).

Disclosed here process by which highly polarized materials can be produced which are free or substantially free of mechanically-induced orientation and in which polarization is essentially stable up to about the crystal melting temperature range (or glass transition temperature) of the polarized material or up to about the softening temperature range or glass transition temperature range of the polarized material in the case of non-crystalline polarized material. The process comprises dissolving a material to be polarized in a solvent or solvents for that material. The solvent is selected which is adapted to the polarization of the material and which can be removed to the extent desired by evaporation during the course of the polarization or prior to or subsequent to the polarization. The temperature employed may be one at which polarization effectively occurs, ordinarily at an elevated temperature at which no substantial dielectric breakdown occurs. The DC field employed in the polarization may be selected to provide the desired polarization. Example 7 disclosed herein below provides an exemplary method of making poled PHA copolymer based articles.

Also provided, herein are polarized products which are free or substantially free of mechanically induced orientation and which are essentially stable up to about the crystal melting point of the material or in the case of non-crystalline material up to about the softening temperature range or glass transition temperature range of the material. The material presently preferred is copolymers of poly(hydroxyalkanoates) and, as a specific example, poly(hydroxybutyrate) polymers.

In an embodiment of the present invention is provided a polarized polymeric composition which is characterized as follows:

is free or substantially free of mechanically-induced molecular orientation;

has polarization which is essentially stable to about the crystal melting temperature range of the polar crystals of the material or to about the softening temperature range or glass transition temperature range of the material if it is non-crystalline; and has mechanical and electromechanical properties isotropic or substantially isotropic in a plane perpendicular to the poling field direction; said polarized material being composition composing essentially all or all of said material.

In an embodiment, the single electrospun finer of PHBHx3.9 mol % yielded a piezoelectric response of 230 milliVolts peak to peal response.

Electrospun Poly[(R)-3hydroxybutyrate-co-hydroxyhexanoate] (PHBHx) Nanofibers

Introduction

Electrospinning, a technique which relies on self-organization via electric charges and their interaction with an applied field, is an efficient and versatile technique to produce ultrafine fibers with diameters down to the range of a few tens of nanometers. Because of the strong stretching forces and fast solvent evaporation kinetics associated with the electrospinning process, the electrospun fibers can have a distinct crystallization behavior compared to the bulk materials. This can lead to the formation of metastable phases or crystalline polymorphs. For some polymeric materials, more than one crystalline polymorph can be found in the electrospun nanofibers, and the population of each polymorph can often be controlled by varying the electrospinning conditions. For example, the coexistence of two crystalline polymorphs have been observed in the electrospun nanofibers of biobased poly[(R)-3-hydroxybutyrate-co-(R)-3-hydroxyhexanoate] (PHBHx) collected with modified collectors. In addition, the concentration of the two crystalline polymorphs, the thermodynamically stable α-form with chains exhibiting a $2_1$ helical conformation and the strain-induced metastable α-form with chains adopting a planar zigzag conformation, can be affected by the collection methods. The implications of these observations are far-reaching since the crystalline structure of a polymer plays an important role in its properties which are manifested after processing. In order to further elucidate the crystallization behavior of the polymer chains during the electrospinning process, studies on the internal structure of a single electrospun nanofiber, including the spatial distribution of the crystalline polymorphs, become essential. Unfortunately, very few techniques can simultaneously provide the necessary spatial resolution and phase sensitivity/specificity.

The combination of atomic force microscopy (AFM) and infrared (IR) spectroscopy can overcome these technical limitations. This new technique, known as AFM-IR, is based on the photothermal induced resonance effect (PTIR). It is a powerful tool which provides topographic information that can be correlated with chemical, conformational, and molecular orientation information at a spatial resolution of 50-100 nm. Unlike conventional FT-IR spectroscopy, the AFM-IR technique uses a sharp, gold-coated AFM tip to detect the rapid thermal expansion of the sample caused by the absorption of short (10 ns) pulses of IR radiation. When the monochromatic laser radiation approaches an IR frequency that excites a molecular vibration in the sample, the light is absorbed and induces a rapid thermal expansion of the sample, which is in contact with the AFM tip. This results in a simultaneous deflection of the AFM tip and causes a "ring down" of the cantilever at its natural deflection resonant frequencies as the heat dissipates. These motions of the cantilever are "detected" by a second laser beam reflected off the top, of the cantilever, and this signal is measured using a position-sensitive photodetector. The resonance amplitude induced in the cantilever is proportional to the amount of IR radiation absorbed by the sample. Thus, the resulting AFM-IR spectrum is obtained by measuring the ring-down amplitudes while tuning the IR laser over the IR fingerprint region. More details concerning this AFM-IR instrument can be found elsewhere. The development of the AFM-IR technique, with the fine spatial resolution provided by the AFM tip and the phase sensitivity provided by the IR spectroscopy is used herein to probe the spatial distribution of crystalline polymorphs in a single electrospun nanofiber.

Disclosed herein is an investigation of polymorphic distribution in single electrospun nanofibers utilizing the AFMIR technique. Bio-based PHBHx nanofibers were fabricated by electrospinning onto the tapered edge of a high-speed rotary disk. The coexistence of the α- and β-form crystalline polymorphs in single nanofibers was confirmed by both AFM-IR and selected area electron diffraction (SAED) via low dose TEM. In addition, the dependence of the β-content and the molecular orientation on fiber size were investigated by these two techniques at the single fiber scale. Furthermore, the spatial distribution of the two polymorphs throughout individual fibers with different diameters was examined by AFM-IR spectroscopy and imaging at a spatial resolution of 50 nm.

Also disclosed herein is a method of formation of the β conformation in PHBHx films through stress induced beta crystallization, where the stress is applied by mechanical stretching the PHBHx film.

Also disclosed herein is a method of forming the β conformation in PHBHx films via a novel method of room temperature isothermal crystallization followed by mechanical stretching. It was confirmed that a crystallites must be present prior to formation of the conformation. The ideal conditions to initially form the β conformation corresponded to 28 minutes of isothermal crystallization. Additionally, this β conformation was shown to be reversible and that the stretching process is, different for the initial β formation and the re-stretching process. The β conformation could also be annealed back into the a conformation at temperatures as low as 48° C.

Due to the apparent importance of the beta form of PHBHx, a solid understanding of this crystal form is desirable. Specifically, evaluating processes through which the polymer transitions into this phase may facilitate the design of processing methods to promote beta formation. IR and Raman spectroscopy are preferred analysis methods for this process, considering the number of vibrational bands attributed to the beta form. Additionally, the resulting spectra can easily be analyzed using 2DCOS, which can determine the sequential order of change in a sample. The most promising avenue is to record spectra as a function of percent strain on a polymer film of PHBHx. Each spectroscopy has its own limitations that need to be considered. The infrared requires the sample to be measured in transmission mode to keep the film from relaxing. However, thin samples are necessary for transmission measurements making them difficult to handle and stretch. On the other hand, though Raman spectroscopy does not require a thin sample, the spectra are recorded only at the laser spot and could be focused away from the area of strain. To overcome this limitation, cuts can be made in the films to form a dog-bone shape, which will force the sample to strain in that region. Therefore, Raman may have advantages over infrared. Resulting samples may be measured with XRD and DSC, if possible. XRD profiles can be obtained with the sample still under strain by positioning the mechanical stretcher in the instrument, thus keeping the sample taut. DSC analysis, however, typically requires the sample to be removed from the mechanical stretching device. Films annealed under stress at a low enough temperature to increase the alpha content but not melt the beta form may permit retention of the strained sample. Preliminary results indicate that inserting the entire mechanical stretcher into a convection oven and annealing the film for approximately four hours may be suitable. The annealing temperature is dependent on the 3HHx content, so to properly determine the correct annealing temperature a series of samples with beta content may be annealed at different temperatures and subsequently measured in the XRD. Once the beta peak disappears in the XRD, a temperature below that sample's annealing temperature may be chosen to lock in the strained structure. DSC measurements can be carried out with these samples, though one should be aware that mechanical relaxation may occur as, the sample is heated. To avoid this the samples may be wrapped around a piece of aluminum before inserting into the DSC pan. Such an analysis not only reveals the specific vibrational bands for the beta form and the process of its formation, but also determines the thermal behavior, i.e. melting point, of the beta crystals. With this information, samples with greater beta content can be more easily designed and applications can be generated with the thermal limitations in mind. Example 2 disclosed herein below provides an exemplary detailed investigation of polymorphic distribution in individual electrospun PHBHx fiber including experimental procedure(s), results and discussion.

Devices Based on PHA Based Copolymers

In an aspect, poly(hydroxybutyrate) PHA copolymer based piezoelectric material of the present invention, as disclosed herein, may be used for any suitable application, including, but not limited to a universal sensor, an actuator, a biobattery, a nanomotor. If used in a nanofiber form, for example, any change in dimension caused by, e.g., humidity, temperature, salinity, nutrient attachment or infusion, metalloid attachment, etc. will create a potential difference (electrical voltage) across its ends. This will give rise to a signal that can be detected remotely. Such a multi-purpose sensor does not exist and the development of such would be transformative, impacting many environmental venues.

In another aspect, PHA copolymer based piezoelectric materials of the present invention, which are biocompatible, biodegradable, and piezoelectric, are used for disposable nanomotors and sensors. In an embodiment, PHA copolymer based piezoelectric materials of the present invention may be used for medical sensors and nanomotors.

Figure 37:
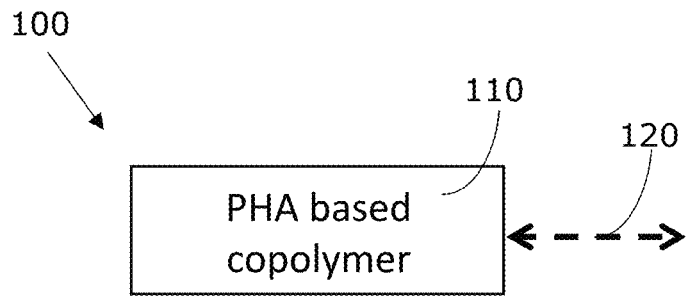
FIG. 37 is a schematic illustration of a sensor/actuator device in accordance with an exemplary embodiment of the invention.

FIG. 37 shows an exemplary device 100, the device 100 comprising a PHA based copolymer layer 110 comprising at least one of an electrospun ribbon of fibers of a polyhydroxyalkanoate based copolymer or the polarized polymeric composition obtained by the process of claim 1, wherein the layer 110 is configured to exhibit one or more of a piezoelectric effect, a pyroelectric effect and a ferroelectric effect, wherein each of the electrospun ribbon of fibers and the polarized polymeric composition comprises a β-form of the PHA based copolymer present in an amount of from about 10% to about 99%, as measured by x-ray diffraction.

In an embodiment, the device 100 may be a sensor configured to produce a potential difference or voltage, corresponding to dashed line 120, in response to a change in dimension of the PHA based copolymer layer. As shown in FIG. 37, in a sensor application, a change in dimension of the sensor, a PHA based copolymer 110, creates a signal output (i.e. electrical charge or voltage) signified by dashed line 120 with the arrow head pointing away from copolymer 110.

In another embodiment, the device 100 may be an actuator configured to change in dimension (e.g. expand or contract) in response to an application of an electrical charge or voltage, corresponding to the dashed line 120, across the PHA based copolymer layer. As shown in FIG. 37, in an actuator application, a charge input, signified by dashed line 120 with the arrow head pointing toward copolymer 110, causes a change in dimension of the PHA based copolymer 110, which change in dimension actuates a desired result.

Figure 38:
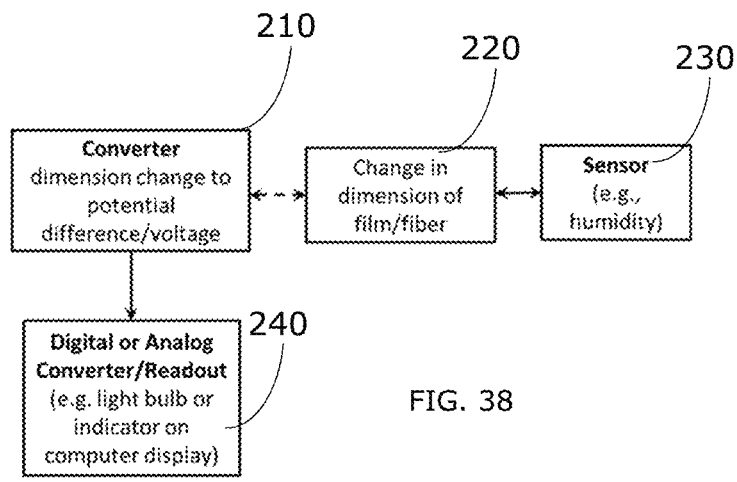
FIG. 38 is a schematic illustration depicting a flowchart relating to an exemplary method of using an exemplary sensor embodiment of the invention.

In a specific example, schematically illustrated in FIG. 38, sensor 100/230 may, comprise a film/fiber 110 that is placed under tension. The presence of a stimulus (e.g. humidity adsorbed into the fiber) may result in a change in dimension 220 of the film/fiber (e.g. swelling) that produces a potential difference 210 via piezoelectric activity that is digitally detected or converted to an analog signal (e.g. lighting of a lightbulb) 240. Changes in, other properties (e.g. temperature, salinity, nutrient attachment or infusion, metalloid attachment, etc.) may produce similar results and outputs.

Figure 39:
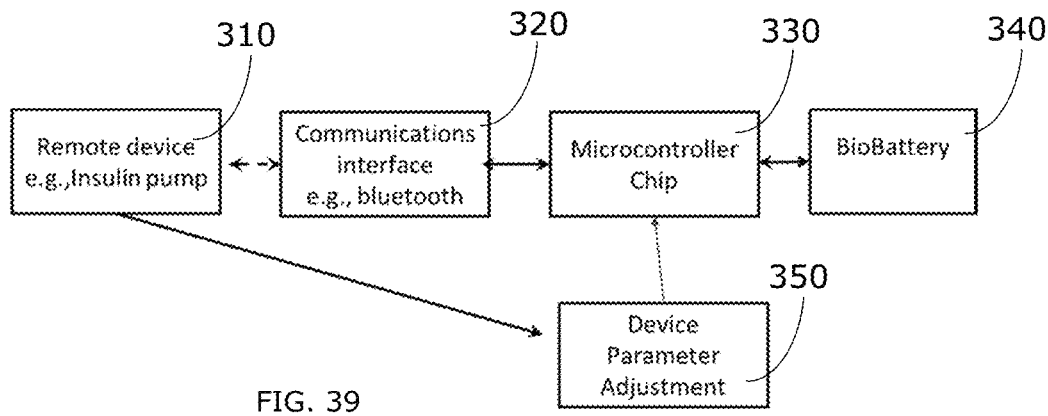
FIG. 39 is a schematic illustration depicting a flowchart relating to an exemplary method of using an exemplary sensor embodiment of the invention in a biological application.

In another specific example, schematically illustrated in FIG. 39, sensor 100/340 may be activated by a biological stimulus, such as in implementation in which the sensor is a "biobattery" (e.g. an energy storing device that is powered by organic compounds, such as, detection of glucose). The presence of the stimulus may result in emission of a signal 120 that is read by processor (e.g. microcontroller chip 330) and communicated by communications interface, which may be wired or wireless (e.g. via Bluetooth® technology), to a treatment device (e.g. insulin pump 310), which may then adjust a relevant parameter 350 (e.g. increase, or decrease insulin). In a monitoring application, the signal 120 emitted by the piezoelectric sensor 100 may be simply used for monitoring a constituent of the patient environment (e.g, an in-situ glucose monitor). Implementations are not limited to detection of glucose, or detection of constituents in the blood. In another implementation, the biological stimulus may be a physiological signal, such as a "beat" produced by a vascular system component (e.g. heart, vein, artery) of an animal or human patient, wherein a change in dimension of the piezoelectric polymer due to the beats (e.g. local changes in pressure) generate the potential difference or voltage read by a processor 330 and communicated 320 to a monitoring or treatment device 310. Exemplary treatment devices 310 may include, for example, a pacemaker, which may adjust the pacemaker signal 350 in response to the measured result. An exemplary monitoring device in this example may include, for example, a blood pressure monitor. Implementations such sensors are not limited to any particular system of an animal or human body.

In another embodiment, a polymer product (e.g. electrospun fiber or other structure) as discussed herein may be configured for use as a sensor by metallization of the structure and adding capture molecules, such as is disclosed in U.S. Pat. No. 9,897,547, incorporated herein by reference.

More specifically, the following represents particular embodiments of the invention:

1. A polarized material which is essentially stable to approximately the crystalline melting temperature range, of the polar crystals of the material or to about the softening temperature range or glass transition temperature range of the material if it is not crystalline.
2. A polarized material of embodiment 1 in which there is distributed therein a plasticizing amount of solvent which can be removed without substantial loss in polarizing stability of the polarized material
3. A polarized material of embodiment 1 wherein the dielectric constant is increased substantially by the presence therein of a dielectric constant improving solvent over the dielectric constant of said polarized material free of said solvent.
4. A polarized material of embodiment wherein the dielectric constant is increased by at least 50 percent
5. A polarized material of embodiment 1 wherein the material is a polarized poly(hydroxybutyrate-co-hydroxyhexanoate) (PHBHx) copolymers in which the polarization is essentially stable to about the crystal melting range of its polar crystals.
6. A polarized material of embodiment 1 wherein the material is a polarized PHBHx copolymer.
7. A polarized material of embodiment 1 wherein the material is a polarized Poly(hydroxybutyrate)/poly(vinylidene fluoride) copolymer.
8. A polarized material of embodiment 1 wherein the material comprises one or more components selected from the group consisting of soluble ceramic materials, PHBHx copolymers, poly(vinylidene fluoride), vinylidene copolymers, Nylon-3, Nylon-5, Nylon-7, Nylon-11, and blends thereof.
9. A polarized material of embodiment 1 in which the material is a polymer having polymer units capable of being polarized and comprises one or more components selected from the group consisting of hydroxybutyrate units, hydroxyhexanoate units, vinyl units, vinylidene units, ethylene units, acrylate units, methacrylate units, Nylon units, carbonate units, acrylonitrile units, cellulose units, units having pendant fluoro, chloro, amide, ester other than ester of acrylate and methacrylate units, cyanide, nitrile other than of acrylonitrile units, or ether groups, protein units or combinations thereof.
10. A method for preparing polarized material which comprises the following steps:
    a) providing a melted composition of one or more polymers in the form of a film capable of being polarized in a preselected form;
    b) quenching the melted polymeric composition;
    c) cold drawing the polymeric composition;
    d) polarizing the cold drawn polymeric composition by applying an effectively high electric field which is of less intensity than that which would cause substantial dielectric breakdown of the polymeric material
    e) annealing the polarized polymeric composition at an annealing temperature less than the melting temperature of the crystals of the polarized polymeric composition whereby the polarization is retained and a thermal stability of the polarization is provided at or near the crystal melting point of the polar crystals of the polymeric composition.
11. The method of embodiment 10 wherein said composition comprises a solution of one or more polymers and a one or more solvents for said polymer or polymers.
12. The method of embodiment 10 wherein said polymer or polymers have polymer units capable of being polarized and comprises one or more components selected from the group consisting of hydroxybutyrate units, hydroxyhexanoate units, vinyl units, vinylidene units, ethylene units acrylate units, methacrylate units, Nylon units, carbonate units, acrylonitrile units, cellulose units, units having pendant fluoro, chloro, amide, ester other than ester of acrylate and methacrylate units, cyanide, nitrile other than of acrylonitrile units, or ether, groups, protein units or combinations thereof.
13. The method of embodiment 10 wherein said composition comprises one or more components selected from the group consisting of polyvinylchloride, polymethylacry-late, polymethylmethacrylate, poly(vinylidene cyani-de/vinyl acetated copolymers, vinylidene cyanide/vinyl benzoate copolymers, vinylidene cyanide/isobutylene copolymers, vinylidene cyanide/methyl methacrylate copolymers, polyvinylfluoride, polyacrylonitrile, poly-carbonate, cellulose, proteins, synthetic polyesters and ethers of cellulose, and poly(gamma-methyl-L-glutamate).
14. The method of embodiment 10 wherein said composition comprises one or more components selected from the group consisting of poly(vinylidene fluoride) and vinylidene fluoride copolymer.
15. The method of embodiment 14 wherein said composition comprises one or more copolymers selected from the group consisting of poly(hydroxybutyrate hydroxyhexanoate), poly(vinylidene fluoride/trifluoroethylene), poly(vinylidene fluoride/tetrafluoroethylene), poly(vinylidene fluoride/vinyl trifluoride) poly(vinylidene fluoride/vinyl chloride) and poly(vinylidene fluoride/methylmethacrylate).
16. The method of embodiment 10 wherein said composition comprises one or more components selected from the group consisting of soluble ceramic materials, PHBHx, poly(vinylidene fluoride), vinylidene copolymers, Nylon-3, Nylon-5, Nylon-7, Nylon-9 and Nylon-11 and blends thereof.
17. The method of embodiment 10 wherein said composition comprise: Nylon-7 and Nylon-11.
18. The method of embodiment 10 wherein said composition comprises about 50:50 by weight of each of Nylon-7 and Nylon-11.
19. The method of embodiment 10 wherein said composition comprises a melt or said polymer or polymers.
20. The method of embodiment 10 wherein said film comprises at least layers of one or more polymers capable of being polarized which are formed from a multiphase composition of said polymers.
21. The method of embodiment 10 wherein said film comprises at least two layers of one or more polymers capable of being polarized which are co-extruded and attached to one another.
22. The method of embodiment 10 therein said film comprises a self-supporting sheet of said composition.
23. The method of embodiment 10 wherein said film comprises a non-self supporting layer of said corn position disposed on a self supporting sheet.
24. The method of embodiment 10 wherein poling is conducted using a field of at least 1 Mv/cm at from about 20° C., to about 120° C. for up to about 5 hours.
25. The method of embodiment 10 wherein the film is annealed at a temperature of from about 125° C., to about 150° C., for at least one hour.
26. The method of claim 10 wherein the composition comprises a blend of PHBHx, poly(vinylidene fluoride) and vinylidene fluoride-vinyl fluoride (80/20) copolymer.
27. The method of embodiment 10 wherein the composition comprises a 50:50 by weight blend of PHBHx and vinylidene fluoride-vinyl fluoride (80/20) copolymer.
28. The method of embodiment 10 wherein the composition comprises a 50:50 by weight blend of PHBHx and poly(vinylidene fluoride).

EXAMPLES

Example 1: Formation of β-Form Crystal Structure in Electrospun Poly[(R)-3-hydroxybutyrate-co-(R)-3-hydroxyhexanoate] (PHBHx) Nanofibers Materials
Poly(3-hydroxybutyrate-co-3-hydroxyhexanoate) (PHBHx) with 3.9 mol % Hx content (Mw=843 000 g/mol, PDI=2.2) was supplied by the Procter & Gamble Company. The polymer was purified by dissolving in chloroform followed by filtration and subsequent precipitation in hexane. The solvent, 1,1,1,3,3,3-hexafluoro-2-propanol (HFIP), was purchased from Sigma-Aldrich and used as received.

Electrospinning

A 1 wt % electrospinning solution was prepared by dissolving the purified PHBHx into HFIP and stirring at 60° C. overnight to ensure complete dissolution. As part of the experimental protocol for electrospinning nanofibers, the polymer solution was loaded into a 3 mL BD plastic syringe With a 21 gauge stainless steel needle, which was connected to the positive terminal of a high-voltage supply held at 10 kV. Two different negatively charged collectors, a parallel-electrode collector and a rotary disk collector, were used to collect electrospun nanofibers with desired morphologies. For the parallel-electrode collector, a rectangular slot was cut in a piece of aluminum foil, leaving the slot as a 35 mm×mm air gap. For the rotary disk collector, the disk was designed to have a tapered edge with half angle of 30° in order to create a converging electric field. The angular velocity of the rotary disk was set to 3500 rpm, corresponding to a linear velocity of 1117 m/min at the edge of disk. The applied voltage between the needle and the collectors was 25 kV. The working distance and solution supply rate were 25 cm and 0.5 mL/h, respectively. All the electrospun mats were dried in vacuum for 24 h to remove any residual solvent prior to further investigation.

Characterization

Fiber Mats: The morphology of the electrospun PHBHx nanofibers was observed using a field-emission scanning electron microscope (SEM, JEOL 3SM 7400F) at an accelerating voltage of 3.0 kV. Fiber diameters were measured using ImageJ software. Wide-angle X-ray diffraction (WAXD) measurements were carried out under ambient conditions using a Rigaku Ultima (IV) instrument operating at 44 kV and 40 mA with Cu Kα ($\lambda$=1.5418 Å) as the X-ray source. Scans were performed in a 2θ range of 10°-40° at a speed of 1°/min and a sample step of 0.1°. The Fourier transform infrared (FTIR) spectra were collected using a Thermo Nicolet NEXUS 670 at room temperature in transmission mode. For each sample, 128 scans were signal-averaged at 4 $cm^{-3}$ spectral resolution.

Single Fibers: Selected area electron diffraction (SAED) patterns and bright-field images were recorded by a transmission electron microscope (TEM, Tecnai $G^2$ 12) with a low-dose CCD camera at an accelerating voltage of 120 kV. The nanofibers were deposited on 300 mesh copper grids coated with lacey carbon film to reduce specimen damage. When performing the SAED experiment, the diffraction patterns were obtained at a fixed camera length of 2.1 m, and the TEM images were taken at a constant magnification of 97000. A thin layer of gold polycrystals was sputtered on each of the copper grid before the deposition of the fibers, which was used to calibrate the camera constant and correct any system distortion.

The high-resolution AFM images and IR spectra of single electrospun fibers were acquired with a NanoIR2 AFM-IR (Anasys Instruments). In order to maintain a good contact between the sample and substrate, PHBHx nanofibers were electrospun directly on silicon wafer substrates that are transparent in the mid-IR region from 900 to 3600 $cm^{-3}$. The NanoIR spectra were collected with a spectral resolution of 2 cm$^{-1}$ coaveraging 256 cantilever ringdowns for each data point.

Results and Discussion

Studies on Fiber Mats: In recent years, many studies have illustrated the huge impact of the collectors on fiber morphologies, macroscopic alignment, and molecular orientation. The morphologies of electrospun PHBHx nanofibers collected using different collectors, while keeping the other electrospinning parameters the same, were examined with SEM, and the images are shown in FIG. 1. The SEM images clearly show how the collectors affect the fiber morphology. Because of the bending instability in the whipping region, the fibers collected on the aluminum foil off the gap are randomized (Al foil random fibers, FIG. 1a), while the fibers collected across the air gap (air gap aligned fibers, FIG. 1b) and on the tapered edge of the rotary disk (rotary disk aligned fibers, FIG. 1c) are well-aligned. Furthermore, the average diameter of the aligned fibers (270±20 nm) was much smaller than that of the Al foil random fibers (500±30 nm), indicating additional stretching and drawing during formation. It has long been accepted that under rotating collection the electrospun fibers were further stretched and aligned toward the rollup direction. However, in the case of the air gap aligned fibers, the stretching is caused by the electrostatic attractive forces between the positive residual charges on the fibers and the negative charges accumulated on the gap edge. These attractive forces, in concert with the repulsive forces between the residual charges on the undischarged fibers in the air gap, result in macroscopic alignment of the fibers.

Figure 2:
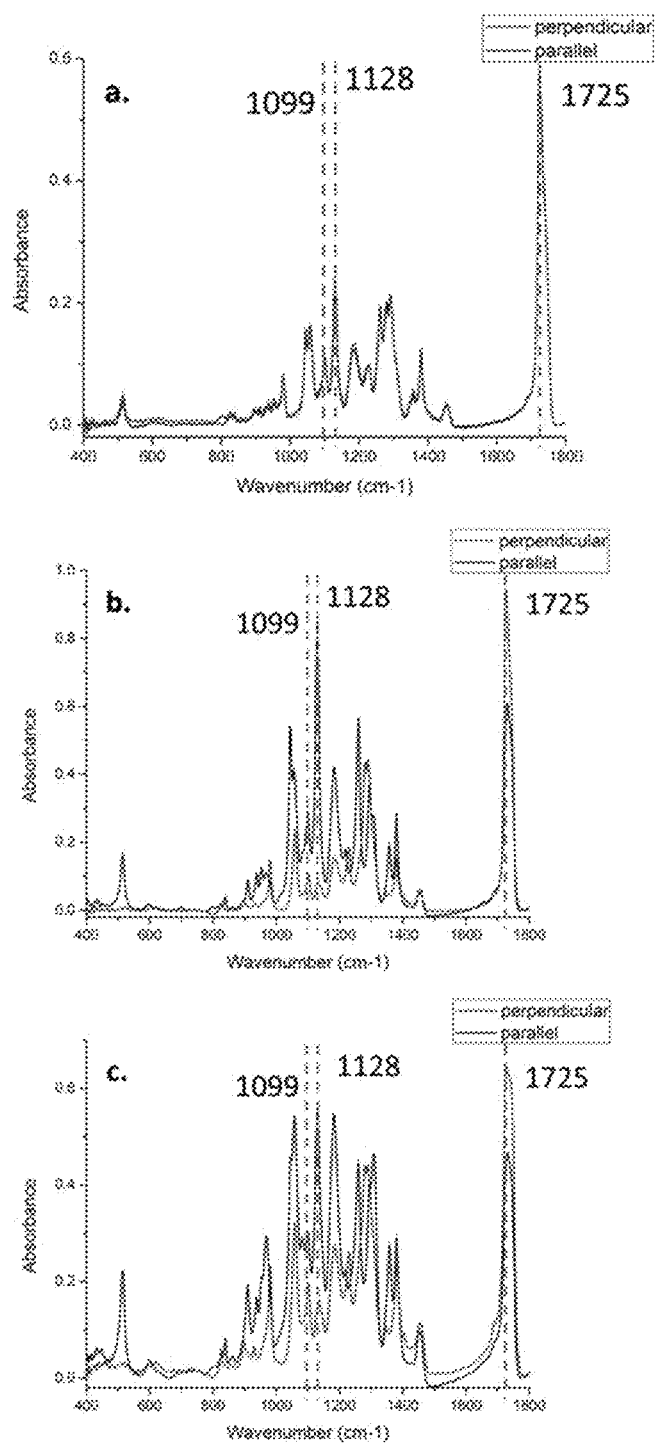
FIG. 2; Polarized FTIR spectra of the Al foil random fibers (a), air gap aligned fibers (b), and rotary disk aligned fibers (c). The incident IR beam is polarized in two mutually perpendicular directions which are perpendicular (red) and parallel (black) to the aligned fiber axis.

In this study, the molecular orientation in the fiber mats was characterized by polarized Fourier transform infrared spectroscopy (p-FTIR). P-FTIR has been widely used to study the molecular orientation and conformational changes of polymer chains during electrospinning. For FTIR spectra with the incident infrared beam polarized in certain directions, a high absorbance intensity will be measured if the change in dipole moment of the vibration has a component along the electric vector of the incident beam. FIG. 2 shows the parallel and perpendicular p-FTIR spectra of the Al foil random fibers (FIG. 2a), air gap aligned fibers (FIG. 2b), and rotary disk aligned fibers (FIG. 2c). As shown in the figure, the p-FTIR spectra for the aligned fibers in two mutually perpendicular directions exhibited a clear difference in absorbance intensity, which indicated the presence of molecular orientation of the PHBHx polymeric chains. In order to quantify this microscopic orientation, the normalized dichroic difference (NDD) of some characteristic peaks was calculated using the equation (assuming uniaxial symmetry)

$$NDD = \frac{A_{\parallel} - A_{\perp}}{A_{\parallel} + 2A_{\perp}}$$

where $A_{\parallel}$ is the parallel-polarized infrared absorbance intensity and $A_{\perp}$ is the perpendicular-polarized infrared absorbance intensity relative to the macroscopic fiber axis. As seen from this equation, the NOD ranged from −½ to 1 with NOD=0 when the sample is isotropic. As listed in Table 1, the NOD for the carbonyl stretch was calculated as 0.001, −0.134, and −0.100 for the Al foil random fibers, air gap aligned fibers, and rotary disk aligned fibers, respectively. NOD<0 indicates that the absorbance intensity of C=O is lower when the electric vector of the incident infrared beam is parallel to the fiber axis compared to that when the vector is perpendicular to the fiber axis ($A_{\parallel} < A_{\perp}$). This result suggested that the carbonyl bond exhibited a perpendicular orientation to the fiber axis, and polymer chains were oriented along the fiber axis because the carbonyl bond is approximately perpendicular to the molecular backbone as anticipated by its chemical structure. As the NOD of carbonyl bond approaches −½, the chains are more oriented along the fiber axis. On the other hand, NDD>0 for the C—O—C bond along the molecular backbone suggests that the C—O—C bonds were oriented approximately parallel to the fiber axis. As the NOD of C—O—C bond approaches unity (1.0), the chains are more oriented along the fiber axis. From Table 1 it should be noted that the air gap aligned fibers had the lowest NDD (highest absolute value) for C=O stretching and the highest NOD for C—O—C stretching, which suggests that the air gap aligned fibers had the highest level of chain orientation along the fiber axis. Particularly, it is noted that the NDDs of the three bands were always around 0 for the Al foil random fibers. This result is due to the lack of macroscopic alignment of the Fibers. Under these conditions, nothing can be said about the degree of chain alignment within the individual fibers.

Figure 3:
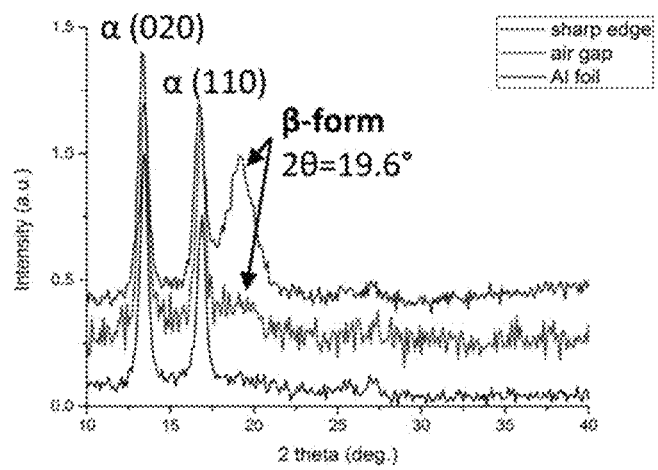
FIG. 3: WAXD profiles of electrospun PHBHx fibers obtained using different collectors.

The crystal morphology f electrospun PHBHx nanofibers was examined by WAXD and FTIR. FIG. 3 shows the WAXD profiles of the Al foil random fibers, air gap aligned fibers, and rotary disk aligned fibers. In all profiles, diffraction peaks assigned to the α-form with a 21 helical conformation were observed. Furthermore, in the WAXD profiles of the air gap aligned fibers and rotary disk aligned fibers, a diffraction peak assigned to the β-form with a planar zigzag chain conformation was observed at 2θ=19.6°. As is apparent, the rotary disk aligned fibers had significantly more β-form than the air gap aligned fibers. For display purposes, the intensity of α(020) at 2θ=13.7° in all the profiles was normalized to unity. Considering that no β-form was found in the Al foil random fibers, this extended chain conformation must be induced by the two modified collection methods where macroscopically aligned fibers were obtained since the different collection strategies (on an air gap vs on a rotary disk rotating, at 3500 rpm) involve substantially different stretching forces on the fiber and a corresponding increase in the amount of β-form produced in the latter.

TABLE 1

Normalized Dichroic Difference (NDD) of Different Vibrational Bands

| vibration band (cm$^{-1}$) | normalized dichroic difference | | |
|---|---|---|---|
| | Al foil | air gap | rotary disk |
| 1725 (C=O stretching) | 0.006 | −0.134 | −0.100 |
| 1128 (symmetric C—O—C stretching) | −0.009 | 0.758 | 0.453 |
| 1099 (asymmetric C—O—C stretching) | 0.009 | 0.348 | 0.151 |

Figure 4:
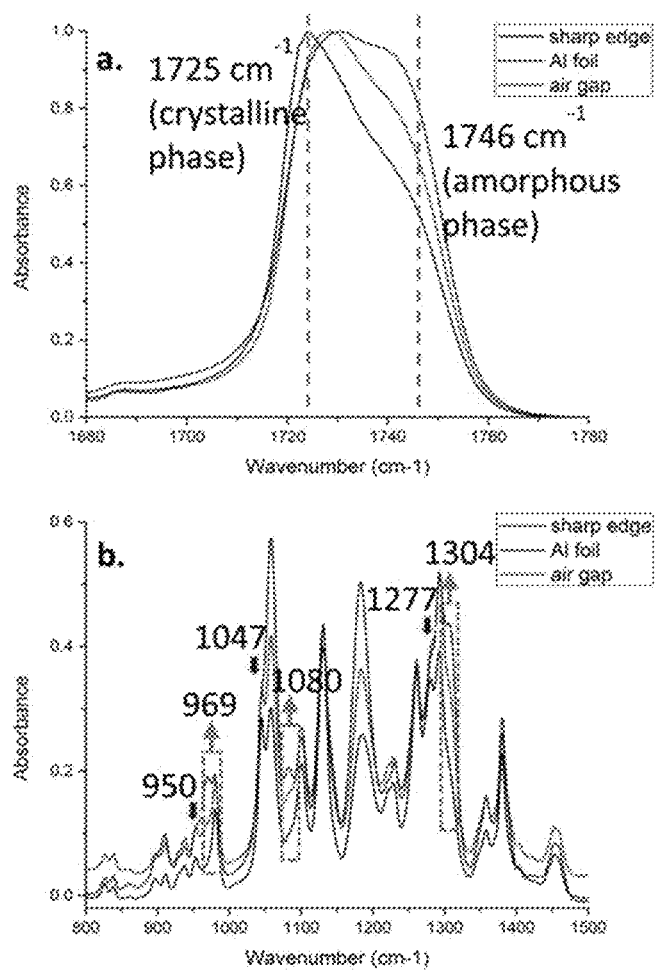
FIG. 4: FT-IR spectra of off-gap random fibers, in-gap aligned fibers, and rotary disk aligned fibers in (a) C☐O stretching region and (b) C—O—C stretching region.

The introduction of the planar zigzag chain conformation in the fibers collected across a gap or on a rotating disk was further confirmed by transmission FT-IR spectra (FIG. 4). The C=O stretching in PHAs is strongly correlated with the polymer backbone conformation. As seen in FIG. 4a, the C=O stretching band of the off-gap random fibers can be resolved into an intense peak at 1725 cm$^{-1}$ corresponding to the crystalline phase and a weak shoulder at 1746 cm$^{-1}$ corresponding to the amorphous phase. As the amount of the α-form increased, going from random fibers to aligned fibers (normalized WAXD result), the peak at 1725 cm$^{-1}$ became broader and shifted to higher frequency, while the shoulder at 1746 cm$^{-1}$ showed an increase in its relative intensity and shifted to lower frequency. In other words, the peak and the shoulder gradually approached each other and became more similar in shape as the concentration of the β crystalline form increased. In addition, some spectral changes also occurred in the fingerprint region. In FIG. 4b, peaks at 1304, 1080, and 969 cm$^{-1}$ developed along with the increase of β-form while peaks at 1277, 1047, and 950 cm$^{-1}$ receded into, shoulders, Similar observations have been made in other studies. These observations are important because they demonstrate a correlation between the presence of the metastable β-structure, (confirmed by WAXD) and the changes, especially the appearance of new bands, in the vibrational spectra. As a result, those peaks mentioned above could be regarded as indicators of the presence of the planar zigzag backbone characteristic of the crystalline polymorph.

Figure 5A:
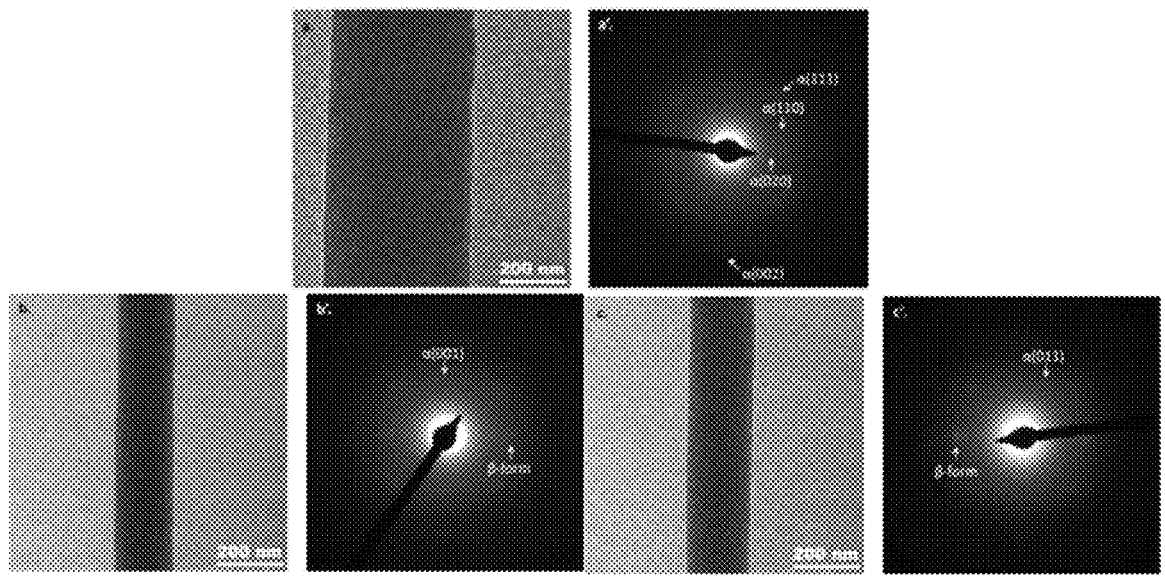
FIG. 5A: Bright-field TEM images of single electrospun PHBHx nanofibers from different collectors (a-c) and their corresponding SAED patterns (a'-c').
Figure 5B:
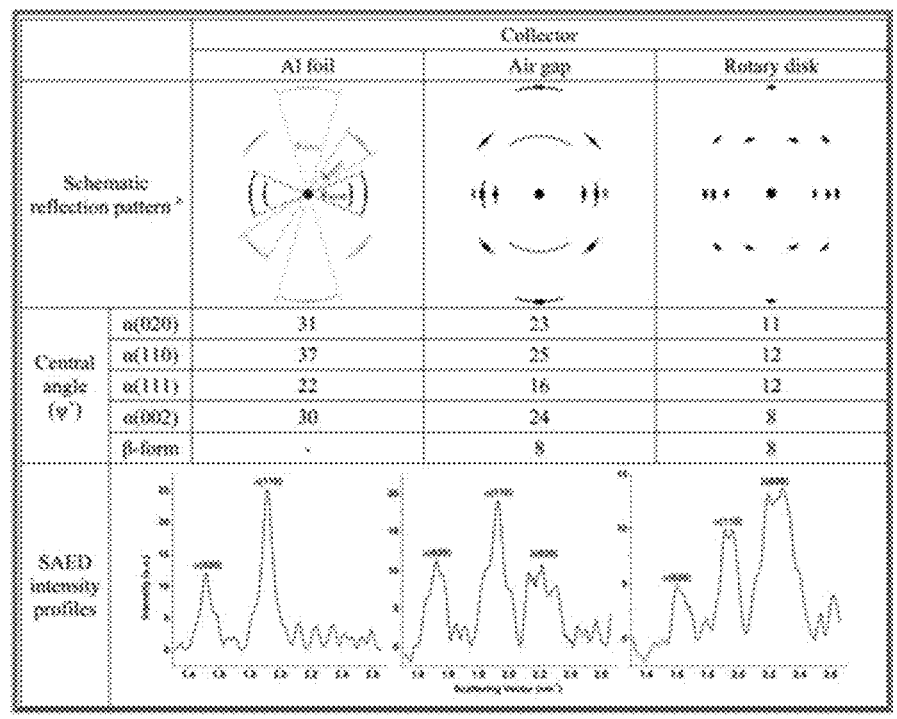

Studies on Single Fibers: Selected area electron diffraction (SAED) via low dose TEM was used to examine the crystal structure and orientation at the single fiber scale. FIG. 5 shows the bright-field images and SAED patterns of individual electrospun PHBHx fibers collected on aluminum foil (a, a'), across the air gap (b, b'), and on the tapered edge of the rotary disk (c, c') The fibers from the air gap (b) and the rotary disk (c) were comparable in size with diameters of 195 and 221 nm, respectively, while the fiber from the aluminum foil (a) was 2 times bigger with a diameter of 495 nm. The corresponding SAED patterns of these three fibers showed clear differences from each other, although all three SAED patterns had crystalline reflections characteristic of the orthorhombic αform crystals, the orientation of the crystals changed significantly when using different collectors. In this study, the crystalline orientation is quantified by the tangential spread of electron diffraction or the degree of the central angles ($\psi$) of the equatorial α(020) and α(110), meridional α(002), and layer α(111) arc-shaped reflections, which are summarized in FIG. 5B. The central angle of the arcs corresponds to the angular distribution of the indexed crystallographic planes, so smaller $\psi$ indicates higher degree of uniaxial orientation of the crystals. From FIG. 5B, it is noted that the fiber from the rotary disk always exhibited the smallest $\psi$ for all arcs, suggesting that in this single fiber α-form crystals had the highest degree of orientation among the three samples, and the polymeric chains in the crystals were highly oriented along the fiber axis. The crystalline reflection of the β-form crystals appeared in fibers from the two modified collectors where a pair of new equatorial arcs were observed in both 4b' and 4c', which are assigned to the β-form crystal plane. Since the β-form crystal structure is a strain-induced paracrystalline structure, this observation indicates that the two modified collectors indeed introduced extra stretching forces on the fibers which are strong enough to stretch the polymer chains to an essentially fully extended form. It is also noted that the β-form arcs always had a small central angle of 8° (FIG. 5B), suggesting a high orientation of the molecular chains in the β-crystals along the fiber axis under different collection conditions.

For each of the three SAED patterns, the intensity profile along the equatorial line was plotted against the scattering vector (1/d, reciprocal of space distance), and the profiles obtained are shown in FIG. 5B. In order to eliminate the influence of nonstructure-related factors, such as electron beam conditions and photorecording conditions, the background gray values for all three SAED patterns were equalized before analysis. The baseline was corrected by fitting the background for each of the profiles. The following observations were made from these intensity profiles, first, from left to right, the intensities of the α(020) and α(110) peaks both decreased while the intensity of the β peak increased, indicating a decrease in α-crystal structure content and a correlated increase in the β-crystal structure content. These observations indicate that the stretching forces from the insulated gap, which are caused by the electrostatic attraction between the positively charged fibers and the negatively charged gap edges and the electrostatic repulsion between the residual positive charges on each fiber, are significantly weaker than those from the rotary disk. In addition, the correlated increase of the β-crystal content along with the decrease of α-crystal content suggests that the formation of the β-form crystal structure is initiated by the stretching forces from the two modified collectors, and α- and β-form crystal structures were formed simultaneously from amorphous and mobile polymer chains by two competing crystallization processes during collection. It is noted that this formation mechanism of the β-form crystal structure is different from those proposed by Iwata and Ishii in which the β crystals are formed after α-crystals. Second, the full width at half-maximum (fwhm) of the two α-peaks increased, indicating a decrease in the effective crystal size according to the Scherrer equation. However, the fwhm of the β-peak in the last two profiles were similar, suggesting that the effective size of β crystals remains the same when experiencing different stretching forces. The decrease of the effective sizes of the α crystals may be due to faster solvent evaporation and thus more rapid solidification when using the modified collectors. As a result, the polymer chains were locked up at the initial state of crystallization. In short, the extra stretching forces provided by the modified collectors during the collection process would initiate the formation of the β-crystalline structure by extending the mobile amorphous chains to a planar zigzag conformation, which competes with the formation of α-crystalline structure. In addition, these stretching forces would enhance the orientation of α-crystals along the fiber axis and decrease their effective sizes. However, the influence of the stretching forces on the orientation degree and sizes of the β crystals is limited.

When the SAED patterns in 5b' and 5c' were carefully examined, it was found that for each indexed α-crystal plane listed in FIG. 5B there was always a superposition of two arcs with different widths in the azimuthal direction, especially in 5b' (see schematics in FIG. 5B). One arc had a larger central angle but was narrower, and the other one had a smaller central angle but was broader, indicating that there were two sets of α-crystals differing in orientation degree arid crystal size. It was also observed that the narrower arc became much smaller as the stretching forces increased from 5a' to 5c' while the broader arc was only slightly smaller, indicating that the stretching had different influences on the orientation of the two sets of αcrystals. Another interesting observation was the appearance of a large α(001) layer line across the meridian in 5b' while two pairs of distinct α(011) arc reflections were observed in 5c'. These results indicate a change in the packing states of the molecular chains in the α-form crystal structure along the fiber axis.

To summarize, the results from the SAED experiments tin single fibers confirm a significant influence of the collection methods on the crystal structure and orientation level of the crystals, which is consistent with the conclusions drawn from the investigations on fiber bundles. Furthermore, the SAED results also demonstrated that substantial polymer chain orientation does occur even in randomly collected fibers on aluminum foil, something that could not be previously determined in fiber bundle studies. These results further indicate that stretching forces during the electrospinning process are large enough to partially orient the chains but are not large enough to extend the chains to a planar zigzag conformation, which requires extra stretching forces during collection. In addition, in the SAED experiments, the rotary disk aligned fibers were observed to have the highest level of chain orientation. This is in contrast to the results obtained from polarized FT-IR experiments where the bundle of air gap aligned fibers apparently shows the highest level of chain orientation among all three samples. This discrepancy may be due to the misalignment and size/morphology nonuniformity (beads) of the rotary disk aligned fibers in the bundle which would cause averaging of the polarized FT-IR signals over fiber bundles. As a result, investigation of individual polymer nanofibers becomes increasingly more important.

As stated above, SAED is a powerful technique for the investigation of single electrospun nanofibers. However, SAED experiments are sometimes difficult and time-consuming. To complement these results a novel technique, AFM-IR, was used which allows direct investigation of both the crystalline and amorphous phases of ultrafine electrospun fibers at the single fiber scale. AFM-IR is a technique combining atomic force microscopy (AFM) and infrared spectroscopy (IR) for nanoscale characterization. It provides IR spectra and AFM images simultaneously of sub-100 nm features. The source is a tunable IR laser whose wavelength can be swept through the infrared "fingerprint" region in less than 1 min. If one of the wavelengths is absorbed by the sample, then thermal expansion of the sample occurs on the nanosecond time scale, which causes a modulation of the oscillating AFM cantilever. This creates a "ringdown" at that particular frequency which decays as the beat dissipates. The positive amplitude of the oscillation represents the IR band intensity, and hence as the frequency is tuned through the IR region (900-3600 $cm^{-1}$), an IR spectrum is obtained at a spatial resolution of 50-100 nm. More details of this instrumentation are reported elsewhere.

In order to test the feasibility of this technique, the IR spectra of a single Al foil fiber and a single rotary disk fiber were collected and compared with the transmission FT-IR spectra of their corresponding fiber mats (FIG. 3, spectra in black and blue). FIGS. 6a and 6b are the AFM images of the two fibers with diameters of 473 and 324 nm, respectively. The IR spectra of these two single fibers are displayed in FIG. 6c, As shown in the figure, the spectrum of the fiber collected on Al foil could be resolved into two features, an intense peak at 1725 $cm^{-1}$ and a weak shoulder at 1746 $cm^{-1}$, corresponding to the α crystalline phase and the amorphous phase, respectively. However, in the spectrum of the fiber collected on a rotary disk, two distinct peaks at 1728 and 1740 $cm^{-1}$ were observed, which were assigned respectively to the more ordered α crystalline phase and the crystalline phase. These nano-IR spectra are in good agreement with the traditional FT-IR spectra in terms of peak/shoulder position and relative intensity. However, it is noted that the peaks in the nano-IR spectra are more highly resolved compared to the corresponding FT-IR spectra which are broadened and smeared due to averaging over a distribution of slightly misaligned fibers.

Generation Mechanism of the β-Form Crystal Structure.

The generation of the α-form crystal structure could have a significant influence on various properties of the material. So far, this strain-induced metastable crystalline structure has been reported in highly crystallized materials of PHB and PHBV processed in different ways, including hot/cold drawn films, two-step-drawn fibers, and one-step-drawn fibers after isothermal crystallization. In these highly stretched PHB or PHBV thin films and fibers, the β-form was believed to originate from the free chains in the amorphous phase between well-developed α lamellar crystals. In other words, the β-form crystal structure is generated after the formation of the α crystals. However, by using similar processing methods, one cannot obtain the β-form crystal structure in PHBHx52 because of the large amount of amorphous chains in the material that could not be highly extended during processing.

Figure 7:
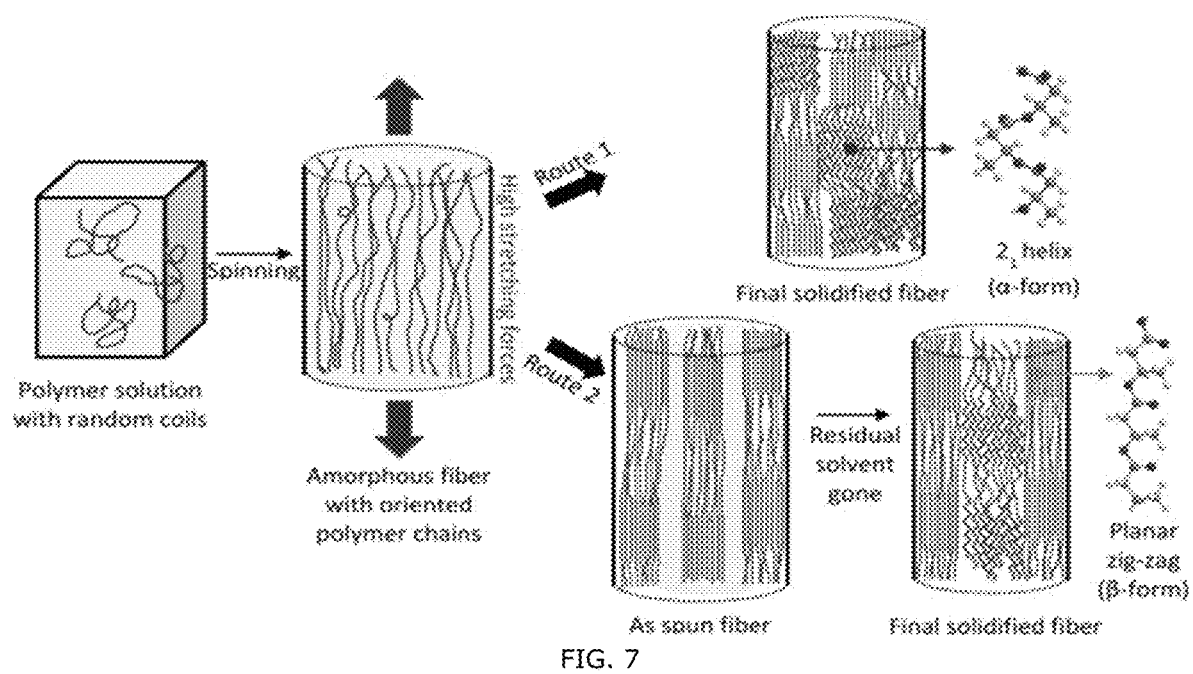
FIG. 7: Two possible generation mechanisms for the formation of the α- and β-form crystal structure during electrospinning and collection. Route 1 indicates the simultaneous formation of the α- and β-crystalline forms during nanofiber collection, Route 2 indicates that the α-crystalline form is generated after the formation of the β-form. The α-crystalline form is originated from the relaxed planar zigzag chains (β-form) due to the existence of residual solvent in the core. In this figure, wavy lines in the fiber illustrate the $2_1$ helical backbones of the chains in the α-phase, straight lines illustrate the planar zigzag backbones of the chains in the β-phase, and random curvy lines illustrate the free chains in the amorphous phase. Cyan color in the figure represents solvent.

In the present disclosure, the β-form crystalline structure in PHBHx was successfully generated by collecting the nanofibers on a high-speed-rotating disk, although the crystallinity of the resultant fibers is as low as 44±1% as suggested by a preliminary DSC measurement (if the crystallinity is calculated with the equation Xc=ΔHm/ΔHm0× 100%, where ΔHm0 is the melting enthalpy of 100% crystalline PHB homopolymer (146 J/g53)), On the basis of the experimental observations that the α- and β-form crystals coexist simultaneously in the resultant fibers and that the increase of the β-crystal content is correlated with the decrease of the α-crystal content with increasing stretching forces during collection (see SAED), it can be concluded that both the α and β crystalline forms are formed during collection. Both appear to be formed from amorphous and mobile chains by two distinct, competing crystallization processes. The possible generation mechanisms of the β crystalline structure are illustrated in FIG. 7. Unlike the generation mechanism reported previously (β-crystals are formed after the α-crystals), the ii-form in the electrospun PHBHx nanofibers is actually formed at the same time as (route 1) or even before the formation of the α-form (route 2). The dissolved polymer chains in their random coil state are highly stretched during electrospinning and thus extended and oriented along the stretching direction. As, a result, the amorphous fibers arriving at the air gap or rotary disk consist of oriented polymer chains along the fiber axis and are plasticized by remaining solvent. During collection, the amorphous fibers are further stretched by the additional elongational forces provided by stretching across a gap or by winding up on a high-speed rotating wheel. At the highest elongation, some oriented chains in the amorphous fiber would be fully extended and adopt a planar zigzag conformation. At high solvent evaporation rates, this metastable β-conformation would be locked in the solidified fiber, and thus β-crystals would be formed simultaneously with the α-crystals, as illustrated in route 1. An additional possibility is that under strong tensile forces during collection most of the polymer chains in the amorphous fiber are fully extended and adopt a planar zigzag conformation. At slower evaporation rates due to the trapping of residual solvent in the core of the as-spun fiber, a portion of the chains, especially in the core, would relax and convert to the mare stable helical conformation (α-form). Therefore, the final solidified fibers would contain both the α and β-crystalline structure, as illustrated in route 2. Realistically, the actual generation mechanism might be a combination of both, and ongoing studies will hopefully provide more insight into the formation process of the β-form in PHBHx.

Although the invention is illustrated and described herein with reference to specific embodiments, the invention is not intended to be limited to the details shown. Rather, various modifications may be made in the details within the scope and range of equivalents of the claims and without departing from the invention.

Conclusion

A microstructural investigation of electrospun PHBHx nanofibers was conducted on fiber mats and on single nanofibers. The molecular chain conformation, the crystal structure, and the orientation of the crystals/chains were investigated by polarized-FT-IR, WAXD, SAED, and AFM-IR and were found to be highly dependent on the collection methods. More importantly, for the first time, the strain-induced β-form crystal structure was obtained in electrospun PHBHx nanofibers by using two modified collectors. The β-form was identified based on the appearance of a new crystalline reflection in WAXD and SAED and the spectral changes observed in the IR spectra. In addition, the results from the SAED experiments on individual fibers provided insights about the correlations between stretching forces and the degree of orientation and size of the α- and β-crystals. Finally, the AFM-IR technique was demonstrated to be a powerful and efficient tool for the microstructural investigation of individual electrospun nanofibers. In addition, according to the experimental results, and without wishing to be bound by any particular theory, a new generation mechanism of the β-form crystal structure is proposed which is significantly different from those, previously reported. The β-crystals, originating from the oriented free chains in the fiber, were formed at the same time as or even before the formation of the α-crystals during collection. The present study has led to an additional investigation of the relationship between the β-structure and the mechanical properties and processing protocols of PHBHx. The corresponding changes in the macroscopic performance of the material, together with its excellent biodegradability and biocompatibility, make PHBHx a promising material in many application areas.

Example 2: Polymorphic Distribution in Individual Electrospun Poly[(R)-3hydroxybutyrate-co-(R)-3-hydroxyhexanoate] (PHBHx)

Polymer.

The bacterially produced poly(3-hydroxybutyrate-co-3hydroxyhexanoate) (PHBHx) with 3.9 mol % hydroxyhexanoate (Hx) comonomer content (Mw=843 000 g/mol, PDI=2.2) was supplied by the Procter & Gamble Company. The polymer was purified by dissolving in chloroform (Fisher Scientific) followed by filtration and subsequent precipitation in hexane (Fisher Scientific). The solvent for electrospinning, 1,1,1,3,3,3-hexafluoro-2-propanol (HFIP), was purchased from Sigma-Aldrich and used as received.

Electrospinning.

A 1 wt % electrospinning solution was prepared by dissolving the purified PHBHx in HFIP and stirring at 60° C. overnight to ensure complete dissolution. At room temperature, the polymer solution was loaded into a 3 mL BD plastic syringe with a 21 gauge stainless steel needle, which was connected to the positive terminal of a high-voltage supply held at 10 kV. A 5 mm thick, negatively charged (−5 kV) rotary disk was used to collect macroscopically aligned electrospun nanofibers. The angular velocity of the rotary disk was set to 3500 rpm, corresponding to a linear velocity of 1117 m/mm at the flat edge. The working distance and solution pumping rate were 25 cm and 0.5 mL/h, respectively. Mid-IR (900-3600 $cm^{-1}$) transparent silicon wafers (Addison Engineering, Inc.) were cut into 5 mm (width)×8 mm (length) pieces and stuck to the edge of the rotary disk. During electrospinning, the fibers were electrospun directly onto the silicon wafer to maintain a good contact between the fiber and the substrate. The density of fibers on the silicon wafer can be easily adjusted by controlling the length of electrospinning time, which, for this study, was set to 45 s to obtain an approximate fiber density of 2 fibers/mm (length). After fiber deposition, the silicon wafers were, put in vacuum for 24 h to remove any residual solvent prior to further investigation.

Microtoming

A bundle of rotary disk aligned nanofibers were parallel embedded in 2 Ton epoxy (ITW Devcon) prior to microtoming. After curing, 250 nm thick sections were cut by microtoming (Leica Ultracut UCT) at room temperature. The thin sections were later transferred to a 10 mm×10 mm ZnS flat for AFMIR studies.

Selected Area Electron Diffraction (SAED)

SAED patterns and bright-field images were recorded by transmission electron microscopy (TEM, Tecnai G2 12) with, a low-dose CCD camera using an accelerating voltage of 120 kV. The nanofibers were deposited on 400 mesh copper grids coated with carbon to reduce specimen damage. The diffraction patterns were obtained at a fixed camera length of 2.1 m. A thin layer of gold polycrystals was sputtered on each of the copper grid before the deposition of the fibers, which was used to calibrate the camera constant and correct any system distortion.

AFM-IR Measurement: Spectroscopy vs Imaging. The nanoscale infrared measurements were carried out with a nanoIR2 platform (Anasys Instruments, Santa Barbara, CA), which focuses radiation from a tunable IR laser source onto a location on the sample top surface from above. A gold-coated SiN AFM tip (Anasys Instruments) with a nominal tip radius of 20 nm was used to examine the fibers in contact mode. The power of the incident IR laser was adjusted to approximately 2% of the open beam intensity for this study in order to obtain a good ring-down signal. Also, an additional mesh filter was placed in front of the IR laser to further attenuate the beam in order to avoid sample melting/softening. For IR mapping, the system was tuned to coordinate the update of the IR signal and the pixel rate of the image. The AFM height and IR peak image were first order flattened using the instrument's built-in software (Analysis Studio, Anasys Instruments). The AFM-IR spectra were collected with a data point spacing of 2 $cm^{-1}$, coaveraging 256 cantilever ring-downs within the spectral range 1680-1780 $cm^{-1}$. The actual spectral resolution in this wavenumber range is 4 $cm^{-1}$, which is the laser line width. For each sampling spot on the fibers, five spectra from the same position were averaged to reach a satisfactory signal-to-noise ratio. All measurements were carried out under ambient conditions.

Results and Discussion

Figure 8:
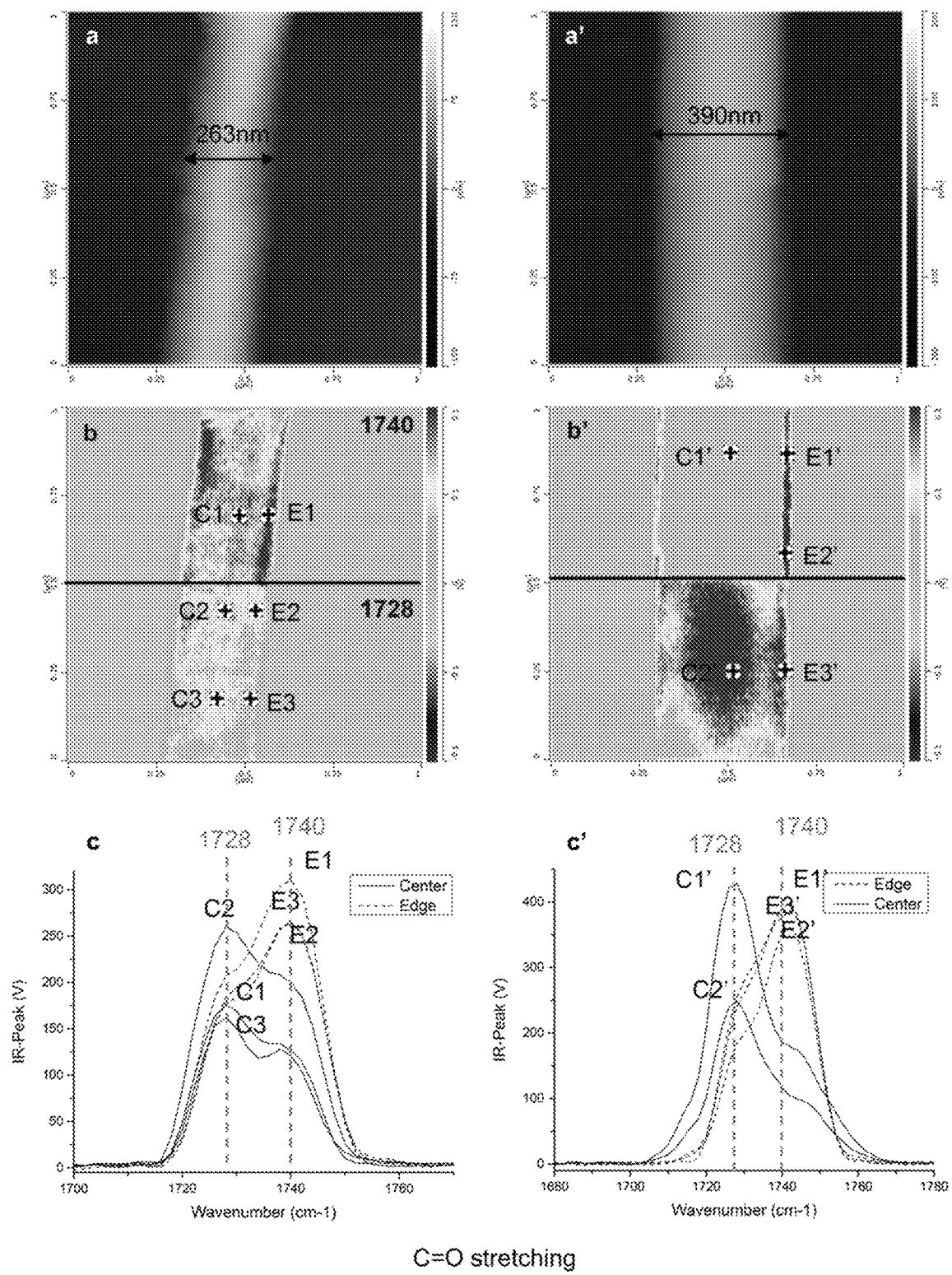
FIG. 8: AFM height images (a, a'), IR peak images (b, b'), and AFM-IR spectra (c, c') of two single electrospun PHBHx fibers. The black spots in (b) and (b') indicate the position of the AFM tip when collecting the AFM-IR spectra.

Macroscopically aligned, electrospun PHBHx nanofibers can be obtained by using a rotary disk as the fiber collector. In this study, individual PHBHx nanofibers from the same batch were examined by AFM-IR. FIGS. 8a and 8a' display the AFM height images of two, single, rotary disk aligned fibers. The two fibers differ in size with diameters of 263 and 390 nm, respectively. Example 1 showed that the strain induced, metastable β-form crystalline structure, with extended polymer chains adopting a planar zigzag conformation, was introduced when the fibers were collected on a high-speed rotary disk. Current results suggest that under this specific electrospinning condition the appearance of the β-crystalline phase is indicated by the characteristic IR absorption peak at 1740 $cm^{-1}$ in the IR spectrum. The IR absorption peak at 1728 $cm^{-1}$ is characteristic of the α-crystalline phase, which is the thermodynamically stable crystal structure of PHBHx. In order to investigate the spatial distribution of the two crystalline phases in the nanofibers, the two single fibers were imaged by tuning the frequency of the incident IR laser to 1740 and 1728 $cm^{-1}$, the two characteristic frequencies corresponding to the β form and α-form crystalline structure, respectively. The IR images are shown in FIGS. 8b and 8b'. For each IR image, the upper half was recorded at 1740 $cm^{-1}$ and the lower half at 1728 $cm^{-3}$. By carefully examining these IR images, one can make several observations. First, when comparing FIGS. 8b and 8b', it is observed that both fibers have detectable IR absorption at 1740 and 1728 $cm^{-1}$, indicating the coexistence of the α- and β-crystalline phase at the single fiber scale. In addition, under the same mapping conditions, the thinner fiber (263 nm) has higher absorption at 1740 $cm^{-1}$ yet lower absorption at 1728 $cm^{-1}$ indicating that the thinner fiber tends to have higher β-content than the thicker fiber (390 nm). Because the two fibers were fabricated under the same electrospinning conditions, the difference in diameter should be due to the different stretching forces they experienced during electrospinning and collection. Assuming extensional strain, the draw ratio of the 263 nm fiber is approximately 2.2 times larger than that of the 390 nm fiber. Since a higher draw ratio favors an extended chain, more molecular chains in the thinner fiber would be found in the planar zigzag conformation and pack to form the β-crystalline form.

Figure 9:
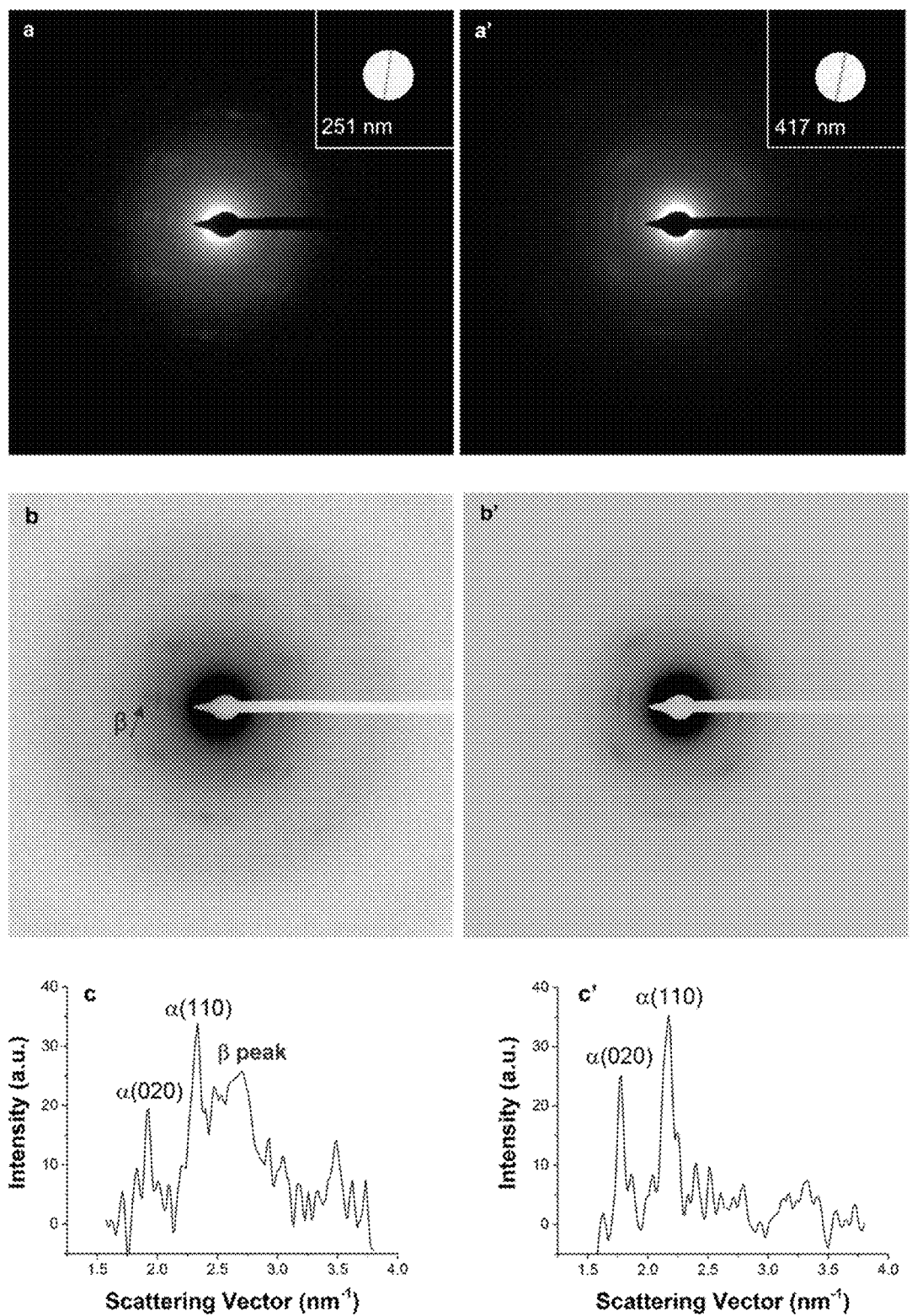
FIG. 9: Original (a, a') and contrast-inverted (b, b') SAED patterns of two individual electrospun PHBHx nanofibers with diameters of 251 and 417 nm, respectively. The insets are bright-field TEM images of the two fibers. The intensity profiles of (a) and (a') along the equatorial line are plotted in (c) and (c'), respectively.

The coexistence of both α- and β-form crystal structures in single PHBHx nanofibers as well as the dependence of the β-form content on fiber diameter is reaffirmed by the SAED patterns of individual PHBHx nanofibers. FIGS. 9a and 9a' display the original SAED patterns of two single PHBHx nanofibers from the same batch. The insets show the bright-field TEM images of the two single fibers. The diameters of the two fibers are 251 and 417 nm, respectively, which are comparable with those of the two fibers in the AFM-IR study. For comparative purposes, the original SAED patterns were contrast-inverted as shown in FIGS. 9b and 9b'. By comparing the two inverted SAED patterns, it is observed that the equatorial arcs assigned to the β-form crystal plane 14 are clearly visible in FIG. 9b (indicated by the red arrow), while in FIG. 9b' they can barely be recognized. For each of the SAED patterns, the intensity profile along the equatorial line was platted in FIGS. 9c and 9c' correspondingly against the scattering vector (1/d, reciprocal of space distance). Obviously, the intensity of the O-peak in FIG. 9c is much higher than that in FIG. 9c', indicating that the thinner fiber contains more β-form crystals than the thicker fiber. In addition, it is also observed that the arcs in FIG. 9b are less tangentially spread, or have a smaller central angle than those in FIG. 9b', which indicates that the thinner fiber (251 nm) has a higher molecular orientation compared to the thicker fiber (417 nm). That is both the content of the β-form crystalline structure and the degree of molecular orientation in a single electrospun PHBHx nanofiber increase as the fiber diameter decreases. On the basis of the results from the AFM-IR and SAED studies, a strong correlation between the β-form content in single PHBHx fibers and the fiber diameter Was observed, which is governed by the stretching forces experienced during the electrospinning and nanofiber collection process. The thinner the fibers are, the higher the β-form content and the higher the degree of molecular orientation.

The second observation that can be mode from the IR images in FIGS. 8b and 8b' is that for both of the fibers the absorption at 1740 $cm^{-1}$ is always higher along the fiber edges, especially in FIG. 8b' where the absorption is almost completely concentrated on the two edges. This observation suggests a heterogeneous spatial distribution of the α- and β-crystalline structures throughout the fiber. More importantly, it suggests an interesting core-shell structure where the shell contains much more β-crystalline polymorph than the core. In addition, by carefully examining the two IR images, it was found that the thickness of the shell, which is indicated by the width of the red lines along the fiber edges, is approximately 10 nm regardless of the fiber size.

In order to test the hypothesis of a core-shell structure for the fiber, for each of the two fibers AFM-IR spectra were collected at different positions where the IR image indicates the existence of heterogeneity. The AFM-IR spectra are shown in FIGS. 8c and 8c'. All the AFM-IR spectra have two characteristic peaks at 1740 and 1728 $cm^{-1}$, which are known 14 to be correlated with the carbonyl stretching of the β- and α-crystalline form, respectively. However, the relative intensity of the two peaks depends on the fiber size and the position within the fiber. For example, in FIG. 8c, the three spectra collected on the fiber edge, E1, E2, and E3, have a relatively higher 1740 $cm^{-1}$ peak while the three spectra collected in the fiber center, C1, C2, and C3, have a relatively higher 1728 $cm^{-1}$ peak. Similar observations were made in FIG. 8c'. For each fiber, the spectra collected at different spots on the edge or in the center share the same spectral shape but differ in absolute intensity. This might be due to the rough surface of the fiber affecting the contact of the AFM tip on the fiber surface from spot to spot.

Figure 10:
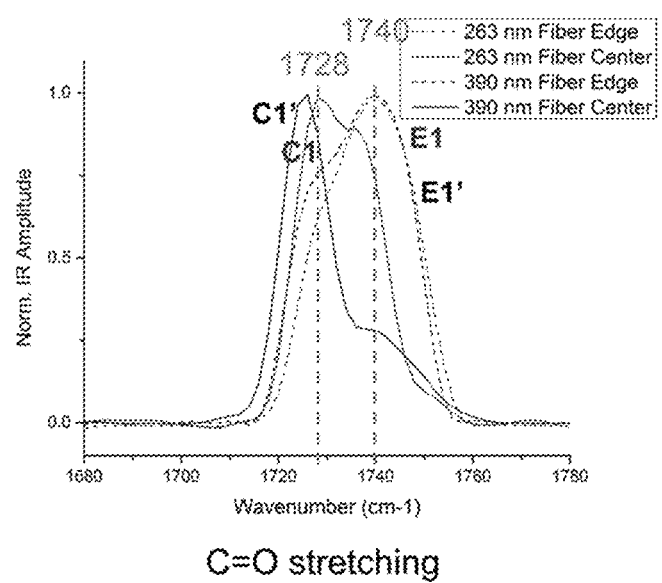
FIG. 10: Comparison of AFM-IR spectra collected from different positions on the two individual electrospun PHBHx nanofibers.

Spectra C1, E1 (spectra in red) and C1', E1' (spectra in black) were plotted in the same figure as shorn in FIG. 10. For comparative purposes, the intensities of the highest peaks of ail spectra were normalized to 1.0. By comparing C1 and C1', it was observed that both spectra have characteristic peaks at 1728 and 1740 $cm^{-1}$, although the 1740 $cm^{-1}$ peak in C1 has a much higher intensity than that in C1', indicating that through the core area the 263 nm diameter fiber has more β crystalline content than the 390 nm diameter fiber. By comparing the color paired two groups of curves, i.e., E1 (solid spectra) and C1', E1' (dashed spectra), it should be noticed that E1 and E1' always tend to have much higher 1740 $cm^{-1}$ peak compared to C1 and C1'. This observation indicates that the morphology of the polymer chains indeed shows heterogeneity throughout a single fiber, and the shell contains more β-form crystals than the core. Interestingly, when comparing E1 and E1', there is not much difference between the two spectra in terms of band shape, which suggests that the crystal structure or the chain morphology in the shell is independent of fiber size.

Figure 11:
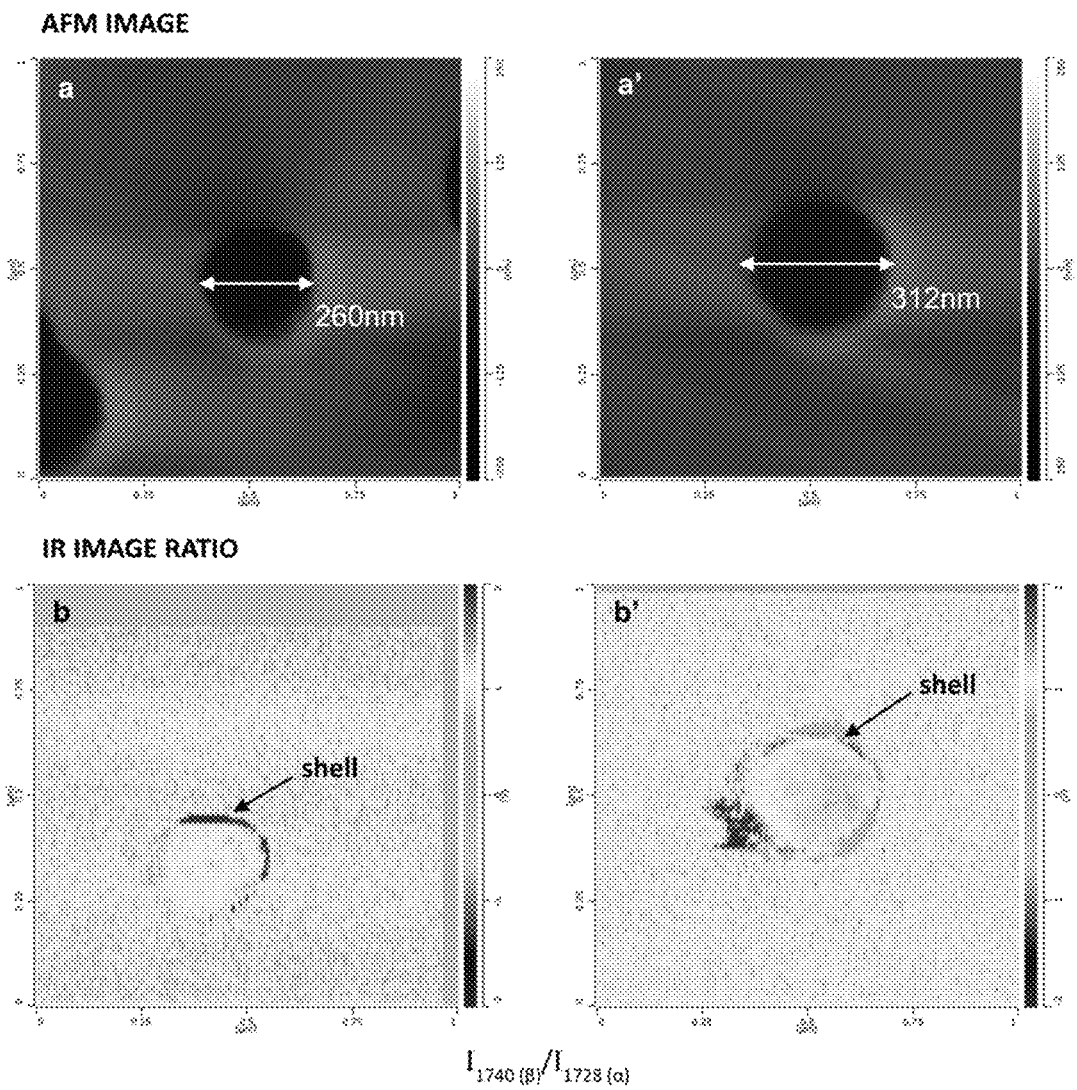
FIG. 11: AFM height image (a, a') and IR peak image ratios (b, b') of the cross sections of two individual electrospun PHBHx nanofiber

Additional support for the conclusion that the rotary disk aligned, electrospun PHBHx nanofibers have a core-shell structure comes from an investigation of the cross sections of the fibers. FIGS. 11a and 11a' show the AFM height image of the cross sections of two rotary disk aligned fibers from the same batch with diameters of 260 and 312 nm, respectively. Again, IR images were captured at the two characteristic frequencies of 1740 and 1728 $cm^{-1}$, In order to eliminate the influence of sample thickness variation and thermal drift, the ratio of the two mappings, i.e. 11740/11728, was taken as shown in FIGS. 11b and 11b'. The color bar indicates the increase of the relative intensity of the IR absorption from purple to red. Since the 2 Ton epoxy has negligible absorption of the IR laser at 1740 and 1728 $cm^{-1}$, the IR mapping ratio in the epoxy area should equal 1, which is represented by the green/yellow color in FIGS. 11b and 11b'. As shown, for each of the two fiber cross sections, a clear red ring was observed at the circumference of the fiber cross section, making a clear differentiation of the fiber cross section and the epoxy. This indicates that in the ring area the ratio of $I_{1740}/I_{1728}$ is is larger than 1, or the IR absorption at 1740 $cm^{-1}$ is higher than that at 1728 $cm^{-1}$. This observation confirms the existence of a thin shell, which contains more β-form crystals, in the rotary disk aligned electrospun nanofibers. Furthermore, for both of the cross sections, the thickness of the ring is consistently found to be approximately 10 nm, which is comparable with the width of the red lines along the fiber edges in FIGS. 8b and 8b'. This strongly suggests that the thickness of the shell in the fibers is about 10 nm, regardless of the fiber diameter. In addition, it is also observed that in FIG. 11b the color in the core area of the fiber cross section is yellow, which shifts toward the red direction compared to the green color in the epoxy area. This indicates a slightly higher content of β-form than the α-form in the core.

Conversely, in FIG. 11b' the color in the core area is green, which shifts toward the purple direction compared to the yellow color in the epoxy area, indicating a lower content of β-form than the α-form. This observation, is consistent with the observation in FIG. 10 where the 1740 $cm^{-1}$ peak in spectrum C1 is higher than that in C1'. However, the ring is not intact around the circumference of the fiber cross section (FIG. 11b), and there is some extra red area beyond the ring (FIG. 11b'). This most likely is due to the smearing of the polymer during the microtoming process, which causes a random burst or contraction of the polymer if the diamond knife is dull or the cutting speed is slow.

Figure 12:
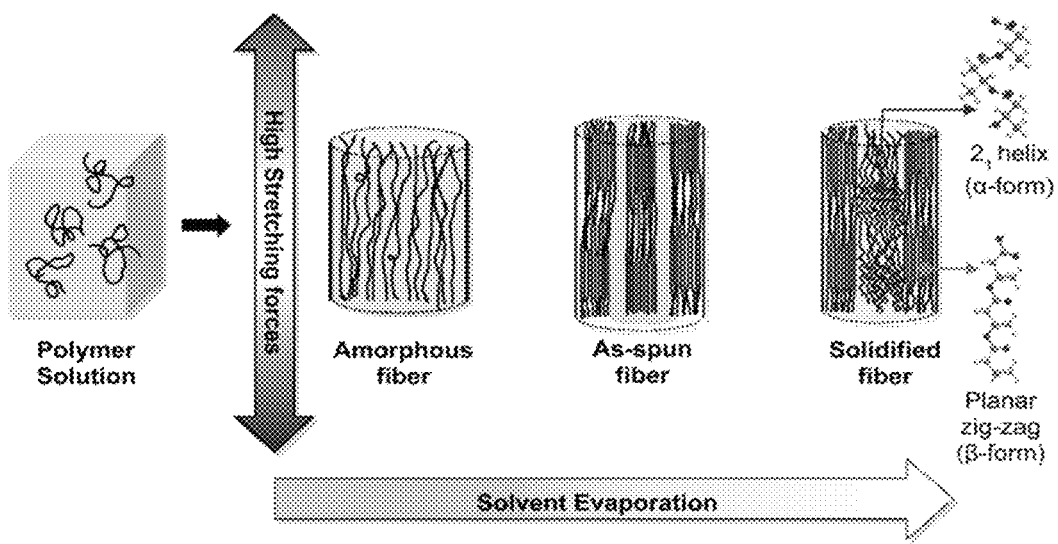
FIG. 12: Possible generation mechanism for the formation of the core-shell structure of the electrospun PHBHx nanofibers collected with a rotary disk. The wavy curves in the core of the final solidified fiber are indicative of the 21 helical backbones of the chains in the α crystalline form; the straight lines in the as spun fiber and the shell of the final solidified fiber illustrate the planar zigzag backbones of the chains in the β-crystalline form; the random curves illustrate the free chains in the amorphous region. The blue color in this figure represents solvent. The thickness of the shell is exaggerated for display purposes.

On the basis of the experimental observations, and without wishing to be bound by any particular theory, a possible mechanism for the generation of polymorphic heterogeneous core-shell structure in the electrospun PHBHx nanofibers collected with a rotary disk is proposed herein, which is illustrated in FIG. 12. The dissolved polymer chains in their random coil state are highly stretched during electrospinning resulting in chain extension and orientation along the stretching direction. As a result, the amorphous fibers arriving at the rotary disk consist of oriented polymer chains along the fiber axis that are plasticized by remaining solvent. During collection, the amorphous fibers are further stretched by the additional elongation forces provided by the high-speed rotating wheel. At the highest elongation, most of the polymer chains in the amorphous fiber are fully extended and adopt a planar zigzag conformation as depicted in the as spun fiber in FIG. 12. Because of the extremely rapid solvent evaporation rate at the surface of the fiber, the planar zigzag chains near the surface will be kinetically frozen and crystallize into the metastable β-form. Thus, a thin layer of skin or shell is formed. Later, the solidified shell would act as a semipermeable barrier, limiting evaporation of the residual solvent in the core. As a result, a portion of the chains, especially in the core, would relax and convert to the more stable helical conformation (α-form). Therefore, the final solidified fibers would have a core-shell structure where crystal structures are different in the core and in the shell.

This core-shell model of the spatial distribution of the α and β-form polymorphs could largely facilitate the understanding of the structure/processing/properties relationships for PHBHx nanofibers. The α- and β-form crystal structures, with the same chemical composition but different molecular packing, have been reported to have distinctive properties, including mechanical properties, biodegradability, and piezoelectricity. For instance, it has been widely recognized that the β-form P(3HB) has much higher strength and modulus than its α-form counterpart. Study of the enzymatic degradation of P(3HB) revealed that the degradation rate of the α-phase with an all-trans conformation is higher than that of the α-phase with a helical conformation. More interestingly, recent experimental results have shown that a piezoelectric response of the PHBHx nanofibers is most likely correlated with the introduction of the β-form crystal structure. Therefore, the final properties of the PHBHx nanofibers can be largely influenced by the composition of the α- and β-phases, which is highly dependent on the electrospinning conditions. According to the core-shell model, if the application of the PHBHx nanofibers requires properties dominated by the β-crystalline structure, one could increase the absolute content of the β-form by increasing the overall stretching forces during electrospinning or expediting solvent evaporation to make it faster than solvent diffusion in the radial direction. In addition, one could increase the relative content of the β-form by reducing the fiber diameter in order to increase the relative volume fraction of the β-phase-rich shell.

Conclusion

For the first time, the spatial distribution of crystalline polymorphs its single electrospun nanofibers was studied with the aid of the AFM-IR technique Electrospun PHBHx nanofibers containing two crystalline polymorphs, the thermodynamically stable α-form consisting of chains with a $2_1$ helical conformation and the metastable β-form consisting of chains with a planar zigzag conformation, were investigated. The coexistence of the α- and β-form polymorphs at the single fiber scale was demonstrated by the AFM-IR spectra and imaging of single PHBHx nanofibers and was reaffirmed by the SAED results. In addition, the molecular orientation level and the concentration of the β-form were confirmed to be highly dependent on the fiber diameter. More importantly, the AFMIR spectra and imaging revealed that the two crystalline polymorphs were spatially distributed as a heterogeneous, core-shell structure consisting of a α-form-rich core and β form-rich shell. The thickness of the shell remained constant though the fiber size varied, indicating that the formation of the shell is predominantly controlled by the competition between the evaporation and diffusion of the solvent. Based on the above experimental observations, a possible generation mechanism of the core-shell structure was proposed. During fiber solidification, the planar zigzag chains, originating from the highly oriented free chains in the fiber, were kinetically frozen near the fiber surface and formed the β-form-rich shell due to the extremely high solvent evaporation rate at the surface. The zigzag chains in the core area of the fiber relax and convert to more stable helical, chains forming the α-form-rich core. This is allowed by the existence of residual solvent, evaporation of which was hindered by the more densely packed shell. This study showed that the AFM-IR technique is indeed an effective and efficient tool for the nanoscale investigation of single electrospun fibers providing both topographic and structural information at a spatial resolution well below the diffraction limit in the infrared. This study could be considered as a template for the nanoscale structural investigation of a variety of polymorphic materials when electrospinning facilitates the formation of metastable crystalline phases, such as nylon-6 and poly(vinylidene fluoride) (PVDF). The investigation of the polymorphic distribution in nanofibers as a function of processing/collection conditions provides s with a deeper understanding of the molecular chain behavior under extremely high shearing/stretching forces plus ultrafast solvent evaporation rate during electrospinning. This level of fundamental understanding of structure/property/process relationships is a critical first step toward the rational design and fabrication of polymeric nanofibers with specific properties which are end-use driven.

Example 3: Measurement of Piezoelectric Effect in Electrospun Poly(R)-3-Hydroxybutyrate-CO—(R)-3-Hydroxyhexanoate) (PHBHx) Nanofibers Electrospinning Macroscopically aligned PHBHx nanofibers containing the metastable β-form crystalline structure were fabricated using a high-speed rotary disk as the collector. Details of the electrospinning process can be found in the Example 1. Specifically, the rotary disk was carefully wrapped with non-sticky aluminum foil, so that free-standing ribbons of highly aligned PHBHx nanofibers can be easily peeled from the flat edge of the rotary disk.

Annealing

It has been reported that the metastable β-form crystalline structure of PHBHx can be annealed back to the α-form by heating to 130° C. Accordingly, ribbon of fibers were annealed at 130° C. in an oven for 24 hours in order to facilitate the conversion of any β-polymorph back to the thermodynamically stable α-polymorph. In order to retain the macroscopic alignment of the fibers, the two ends of the ribbon of fibers were clamped onto a glass slide and held there during annealing.

Fiber Mat Characterization

The morphology and crystal structure of the rotary disk aligned fibers before and after annealing were characterized by Scanning Electron Microscopy (SEM) and Wide Angle Xray Diffraction (WAXD).

Measurement of Piezoelectric Response

Figure 13:
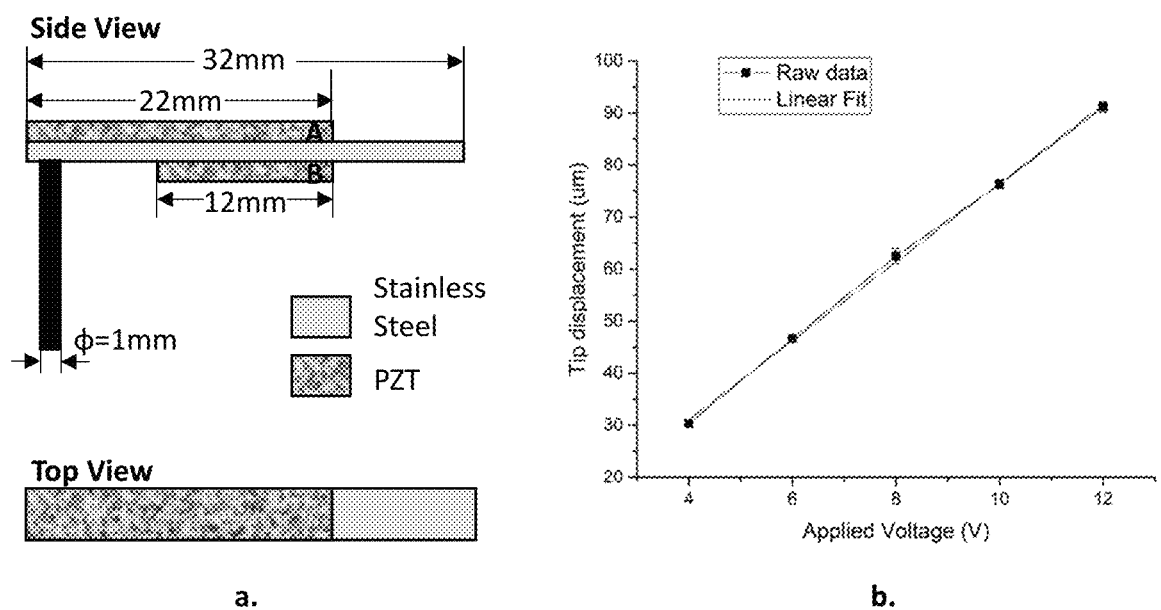
FIG. 13: Schematic diagram of the piezoelectric cantilever (a) and a plot of the displacement of the probe against applied voltage (b).
Figure 14:
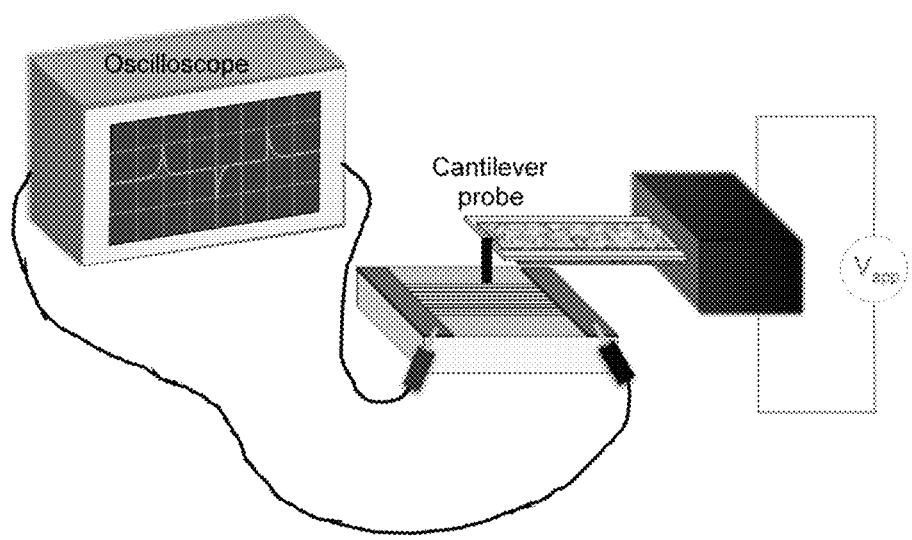
FIG. 14: Schematic diagram of the piezoelectric response testing instrument.

A piezoelectric cantilever was used to test the piezoelectric response of the macroscopically aligned PHBHx nanofibers. As illustrated in FIG. 13(a), two piezoelectric lead zirconate, titanate (PZT) sheets (T105-H4E-602, Piezo Systems), A and B, were glued onto the top and bottom of a 32 mm long×3.5 mm wide rectangular stainless steel layer. PZT sheet A at the top has a dimension of 22 mm (length)×3.5 mm (width), while sheet B at the bottom is slightly shorter with a dimension of 12 mm×3.5 mm. A thin brass cylinder with a diameter of 1 mm was glued to the tip of the cantilever to act as the testing probe. More details about the piezoelectric cantilever can be found elsewhere. Due to a converse piezoelectric effect, the application of external voltages across the PZT sheet A will generate axial displacement of the cantilever, as well as the testing probe, FIG. 13(b) shows the displacement of the probe at different applied voltages. The probe displacement was measured using a laser displacement sensor (LC-2450, Keynece Corporation) with a resolution of 0.5 µm. The external voltage was supplied by a function generator (Agilent 33220A, 20 MHz).

For measuring the piezoelectric response of the fibers, a 5 mm wide×10 mm long ribbon of fibers was interfaced with a flexible PDMS substrate. In order to reduce the background noise, this PDMS substrate was covered with insulating Kapton® tape. Conductive copper tape (3M 3313, ½ inch), serving as the electrodes, was used to stick the two ends of the ribbon of fibers onto the substrate in a way such that the aligned fibers are completely straight without load. The piezoelectric test started with a careful engagement of the cantilever probe onto the surface of the ribbon of fibers, Square wave voltages, supplied by the function generator, were applied across the cantilever to generate the vibration of the cantilever at a frequency of 10 Hz. The probe, in contact with the ribbon of fibers, thus deformed the straight fibers synchronously. The induced voltages resulting from the deformation of the aligned fibers were recorded on a digital oscilloscope (Agilent Infinitum 1.5 GHz, 8 GSa/s).

The experimental set-up is illustrated in FIG. 2. Control experiments were performed to verify that no obvious voltage signal was observed without the ribbon of fibers. All experiments were performed on a Newport optical table (RS100, Newport Corporation) to minimize background vibrations.

Results and Discussion

Figure 15:
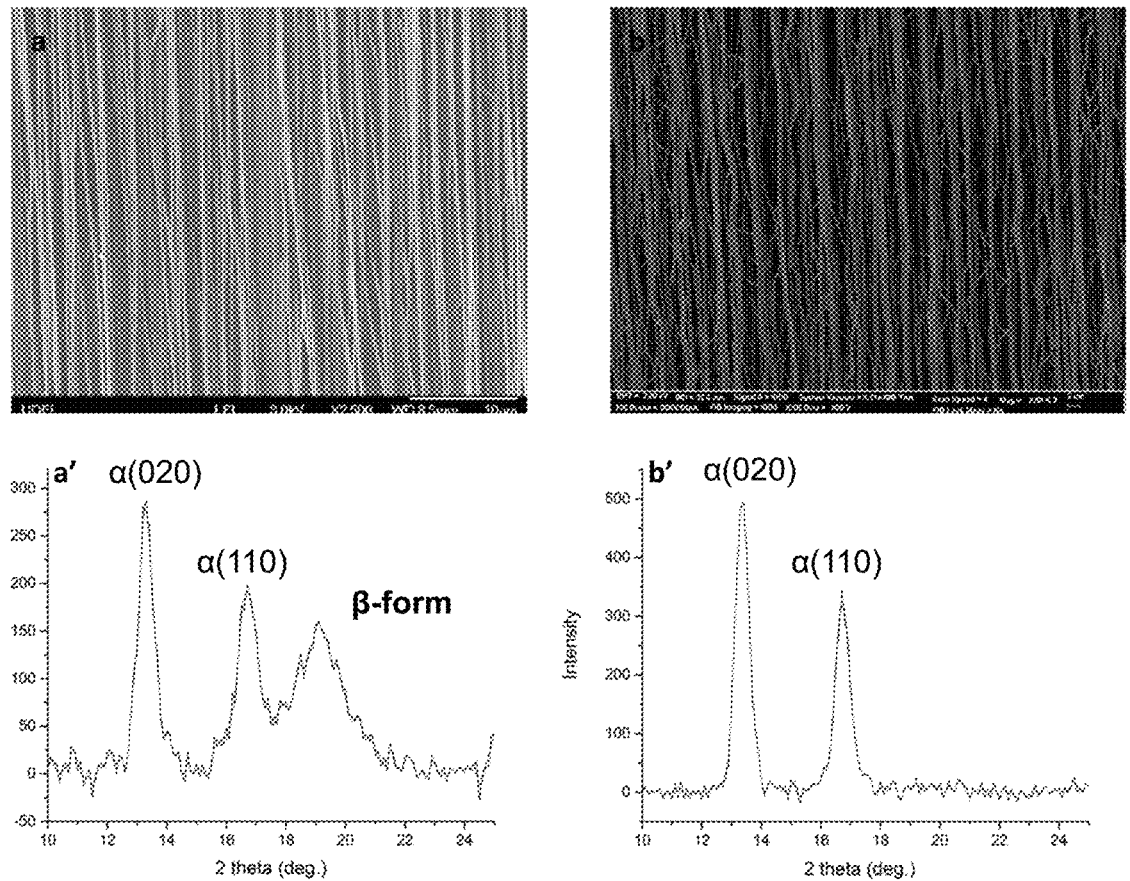
FIG. 15: SEM images and WAXD patterns of the macroscopically aligned nanofibers before annealing (a, a') and after annealing (b, b') at 130° C. for 24 hours.

The morphologies and crystal structures in macroscopically aligned PHBHx nanofiber bundles before and after annealing are shown in FIG. 15. It is observed that after annealing, the macroscopic alignment of the fibers remained constant. The β-form crystals disappeared, presumably by conversion to the thermodynamically stable α-form, as demonstrated by the loss of the X-ray diffraction peak of the β-form at 19.6° shown in FIG. 15b'. Furthermore, the two diffraction peaks of the α-form became narrower, i.e. the FWHM of the two α-peaks became smaller after annealing, indicating that the size of the α-crystals increased due to the reorganization of the molecular chains during annealing.

The piezoelectric response of the PHBHx nanofibers before and after annealing was measured with an applied voltage of 10V. The results are presented in FIG. 4, Quantitatively, the fibers before annealing (signal in black) exhibit a much higher voltage output (c.a. 240 mV peak to peak) than the fibers after annealing (signal in red), indicating a strong correlation of the piezoelectricity of the fibers with the presence of the β-form crystal structure.

Figure 16:
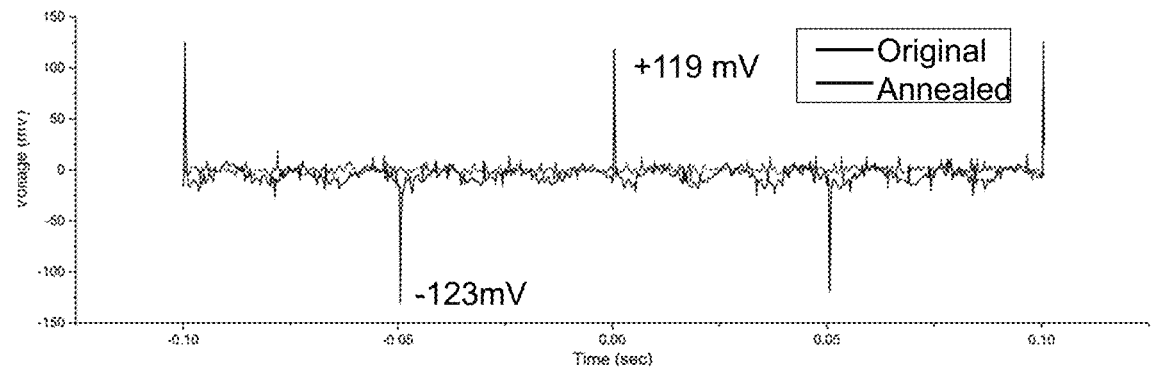
FIG. 16: Induced voltage vs, time output of the rotary disk aligned PHBHx nanofibers before annealing (black signal) and after annealing (red signal).
Figure 17:
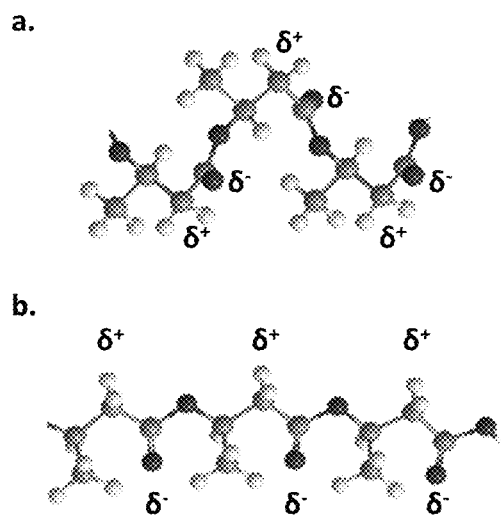
FIG. 17: Electric dipoles in (a) 21 helical PHB chains (α-form) and (b) planar zig-zag PHB chains (β-form)
Figure 18:
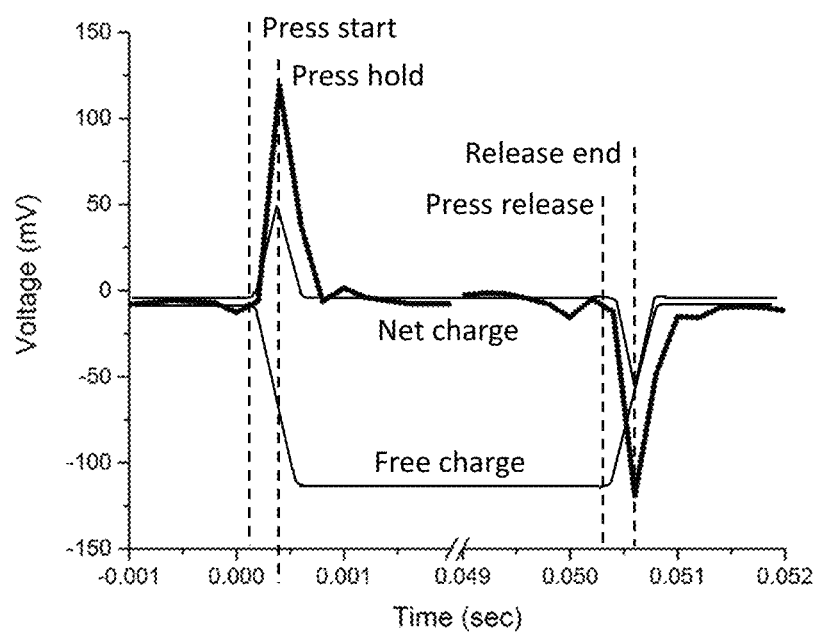
FIG. 18: Electric charge movements during a press-hold-release cycle. The black line represents the real voltage signal. The dark green line represents the free charge transport from the external circuit to the fibers. The pink line represents the net charges in the ribbon of fibers.

The β-crystalline form contains molecular chains that exhibit a planar zig-zag conformation. As shown in FIG. 17b, the electronegative O atoms from the C=O group and the electropositive H atoms from the adjacent $CH_2$ group reside on opposite sides of the polymer backbone. As a result, a net dipole moment is formed perpendicular to the polymer backbone. Previous studies showed that the polymer chains in the rotary disk aligned fibers are highly oriented along the fiber axis. Therefore, when aligned fibers are bent, the oriented polymer chains confined in the fibers are deformed, which causes a change of the dipole moment. Consequently, a potential difference is generated between the two ends of the fibers, which appears as the positive black voltage spikes in FIG. 16. On the other hand, although electric dipoles exist in the molecular chains of α-form, the left-handed 21 helical conformation aligns all the dipole moments in a way that they cancel each other (FIG. 17a). This results in a zero net dipole moment in α-crystals, and thus the annealed aligned fibers containing only α-form crystalline structure exhibit no piezoelectric response. Interestingly, Ando and his co-workers (doi: 10.1109/ TEI.1986.349101: doi: 10.1016/0141-8130(86)90056-5; doi:10.1002/pol.1984.180221010) investigated the piezoelectric properties of α-PHB and found that oriented α-form PHB exhibits intrinsic shear piezoelectricity. The internal rotation of dipolar atomic groups associated with the asymmetric carbon atoms (O=C—$CH_2$, FIG. 17a) in the helical chains of α-form seem to cause electric polarization when shear stress is applied. However, this shear piezoelectricity was not observed in FIG. 16. This difference might be due to: (1) the molecular chains are not sufficiently sheared in this experiment to display the shear piezoelectricity, since the shear piezoelectric coefficient of α-PHB is low; or (2) the annealing process may have degraded the high orientation level of the chains, so α-crystals after annealing are randomly distributed in the fibers. Further investigations are necessary to gain a better insight into this observation.

Figure 6:
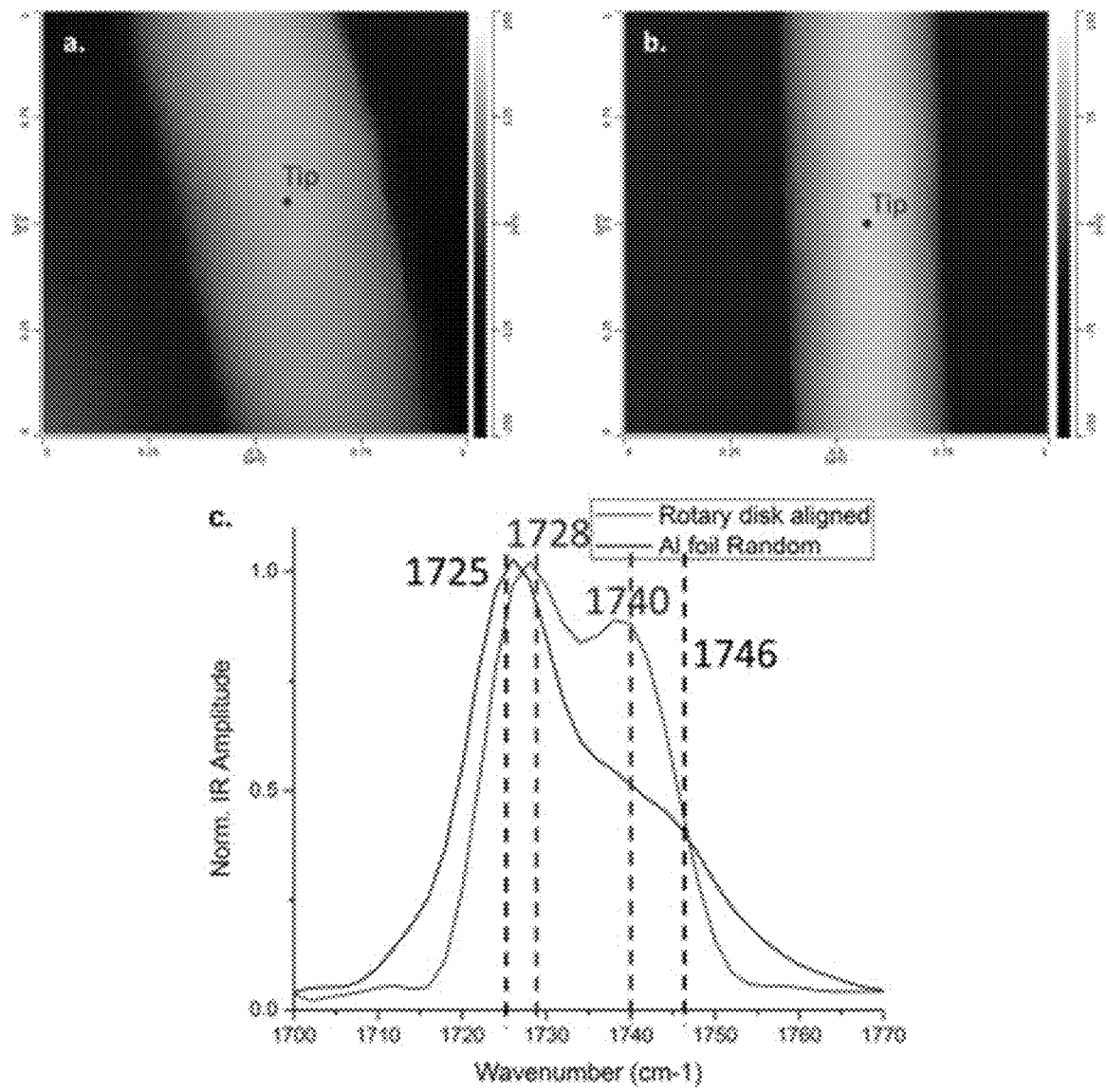
FIG. 6: AFM images of single electrospun PHBHx fibers collected on (a) aluminum foil (473 nm) and (b) the tapered edge of a rotary disk (324 nm). (c) IR spectra of fibers shown in (a) and (b). The red dots on the two individual fibers indicate the position of the AFM tip.

Another interesting feature in FIG. 4 is the alternative appearance of positive and negative voltage spikes. This phenomenon can be explained by the charge and discharge of the piezoelectric PHBHx fibers during the press-hold-release cycle (FIG. 6). When the brass probe starts to press the ribbon of fibers, the oriented molecular chains in the fibers are deformed, which results in an instantaneous potential difference between the two ends of the ribbon of fibers. Quantitatively, this potential difference is represented by the positive voltage signal of 119 millivolts in FIG. 6. In response to this induced potential difference, external free charges (green line) are driven to the ribbon of fibers to neutralize this potential difference. During this process, the net charge (pink line) on the ribbon of fibers increases. When the press is held, i.e. the mechanical strain remains constant, both the induced potential difference and the net charge are gradually diminished, as the piezoelectric bound charges are balanced by the external free charges. At zero potential difference, the ribbon of fibers is fully charged. When the press is released, the built-in potential difference disappears, and the external free charges accumulated at both ends of the ribbon of fibers flow back in a direction opposite to the accumulation process. This reversal results in a quantitative opposite potential difference (−123 millivolts) which is observed as the negative voltage signal. As shown in FIG. 6, the opposite potential difference and net charge also experience a gradual reduction. As soon as the potential difference reaches zero, the discharge of the ribbon of fibers is complete.

Figure 19:
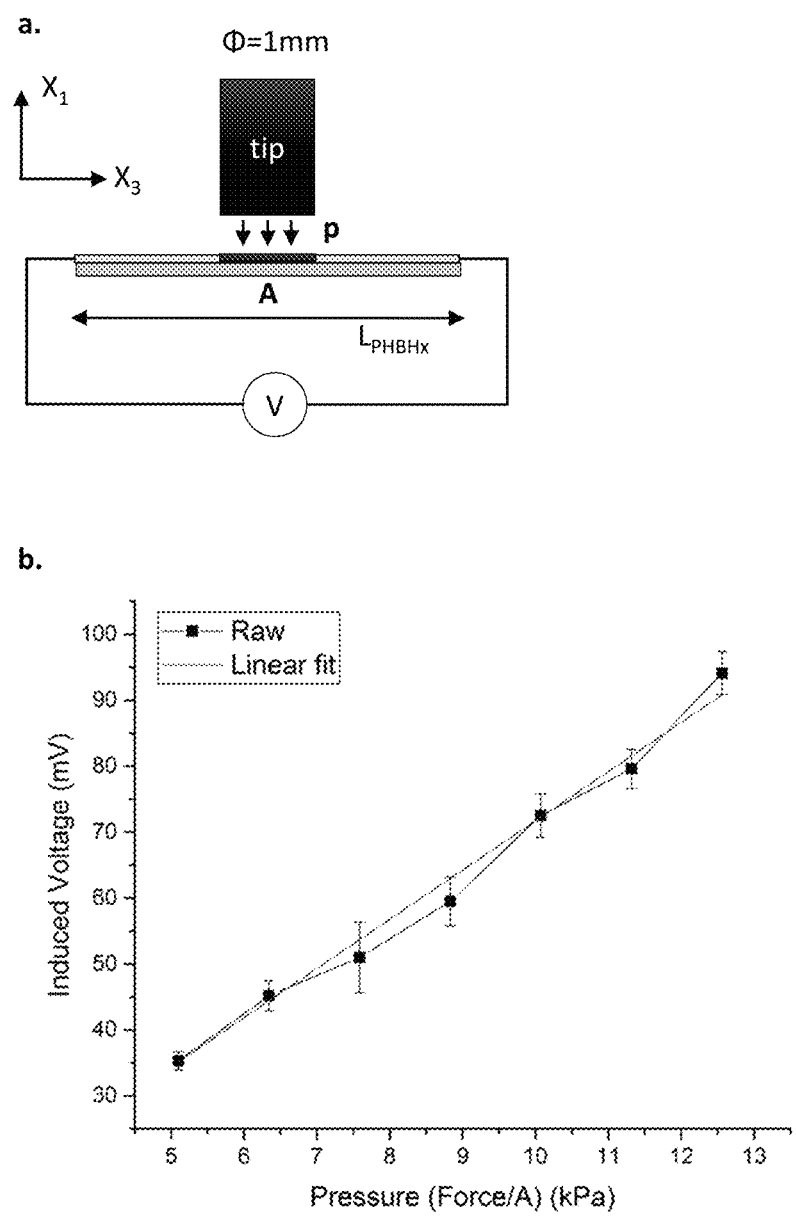
FIG. 19: (a) Schematic illustration of an analytical model for the response of the PHBHx ribbon of fibers under applied pressure. The blue letter p and red letter A denote the applied pressure and the contact area of the probe and the ribbon of fibers, respectively. (b) Experimental (black) and linear fitted (red) pressure response curves

The above experimental results suggest the possibility of using piezoelectric PHBHx nanofibers as nanogenerators, Meanwhile, the piezoelectric characteristics make the ribbon of fibers promising budding blocks for piezoelectric sensors. In order to evaluate the sensitivity of the ribbon of fibers, the applied voltage was adjusted to explore the relationship between the induced voltage and the applied pressure using the apparatus shown in FIG. 19. The pressure applied on the fibers is calculated by the equation:

$$p=(K \times D)/A$$

where K represent the spring constant of the cantilever, D is the axial displacement of the probe, and A is the contact area of the probe with the ribbon of fibers. It is known that K=128.9±2.2 N/m.

D is measured by the laser displacement sensor as shown in FIG. 19a and A=$\pi r^2$ where r=0.5 mm. The induced voltages were recorded through a range of applied voltages from 4 to 10 V with increments of 1 V. A plot of the induced voltage as a function of the applied pressure is shown in FIG. 19b, and a linear relationship was observed. Hence, the sensitivity of the ribbon of fibers can be calculated from the slope of the linear fit, which turns out to be 7.46 mV/kPa. Although this sensitivity seems to be much low compared to other piezoelectric sensors, it can be improved by methods including; 1) changing the sensor architecture, stacking multiple layers of piezoelectric ribbon of fibers together; or 2) increasing the concentration of the piezoelectric-active component (β-crystals) in the fibers.

Conclusions

In this study, the piezoelectric properties of the electrospun PHBHx nanofibers were investigated as a function of crystal structure. The piezoelectric response of the rotary disk aligned fibers, before and after annealing, was characterized. The results showed that nanofibers containing the metastable β-form crystalline structure consisting of planar zig-zag chains, exhibit an obvious piezoelectric response (240 millivolts peak-to-peak) when mechanically deformed. However, after annealing and conversion of the β-form crystals to the α polymorph this piezoelectric response disappeared. This observation indicated a strong correlation between the piezoelectric properties of the fibers and the presence of the β-form crystalline structure. Subsequently, the sensitivity of the piezoelectric PHBHx nanofibers to the applied pressure was measured. The induced voltages were recorded as the applied pressure was changed and a linear relationship was observed. From the slope, a piezoelectric sensitivity for the fibers was measured to be 7.46 mV/kPa. The implications of these preliminary investigations of the piezoelectricity of PHBHx are far reaching. Piezoelectric performance of this material can be significantly improved by increasing the concentration of the active β-form crystalline structure. That goal can be accomplished by utilizing innovative polymer processing techniques, such as those discussed herein. The piezoelectric PHBHx distinguishes itself from all the other piezoelectric polymers with its excellent biodegradability and biocompatibility, environmental-friendliness and most importantly, low manufacturing cost. It is a very promising piezoelectric polymer that may find applications in many advanced areas including portable and foldable electronic devices, artificial electronic skin and implantable sensors.

Example 4: Stress-Induced Beta Crystallization of Poly[(R)-3-hydroxybutyrate-co-(R)-3-hydroxyhexanoate] in FILMS Materials Poly[(R)-3-hydroxybutyrate-co-(R)-3-hydroxyhexanoate] (PHBHx) copolymers with 3.9 and 13 mol % 3HHx comonomer content were supplied by the Procter & Gamble Company, Cincinnati, Ohio with no further purification. The weight average molecular weight of the 3.9 and 13 mol % 3HHx copolymers were 843 and 792 kg/mole, respectively. Chloroform was purchased from Sigma-Aldrich Co., Ltd and used without further purification.

Sample Preparation

Films of PHBHx were prepared by dissolving the polymer in chloroform and solvent casting the film on a Teflon block to avoid binding to the casting surface. The annealed films were conditioned in an oven at 70° C. for 4 hours prior to analysis. Samples for IR spectroscopy were cast from 3 wt % PHBHx solutions and those for the Raman and XRD analyses were cast from 10 wt % PHBHx solutions. Lower concentration was required for the IR measurements to generate films thin enough to avoid total absorption of the IR beam. Conversely, higher concentration was required for the Raman and the XRD to provide a thick enough sample to focus the laser on for the Raman and to generate diffraction in the XRD. The cast films were dried in a vacuum chamber for approximately 4 hours to remove all residue chloroform. After solvent removal, the films were melted in a convection oven at 140° C. for 20 minutes to completely melt the polymer and then immediately quenched into ice water to retain the amorphous state below the Tg. The films were stored at −25° C., loaded on a mechanical stretcher at −25° C., stretched to approximately 50% strain at −25° C., and returned to room temperature. The final strain was applied sequentially while IR or Raman spectra were collected, up to approximately 150% strain. XRD diffraction profiles were collected on the samples after they were fully strained and measured in the Raman.

Fourier Transform Infrared (FTIR) Spectroscopy

The infrared absorbance spectra were recorded using a Thermo Nicolet 670 Nexus FTIR spectrometer equipped with a DTGS KBr detector and a KBr beamsplitter in transmission with the polymer films mounted on a mechanical stretching device. Spectra were collected by co-adding 16 scans at 4 cm-1 resolution over the region of 4000 to 600 cm$^{-1}$, IR spectra were processed by baseline correction with a cubic spline fit, truncating the spectra from 1550 to 700 cm$^{-1}$, and normalizing them using SNV normalization, Truncation was performed to avoid distortion of the normalization coefficient by the carbonyl, which was over absorbing due to the thickness of the film.

Raman Spectroscopy

Raman measurements were performed using a Raman instrument composed of a diode laser (Ondax) with 785 nm excitation and an Ondax probe head optical filtering module. The collected scattered light was analyzed using a Kaier Optical Systems Holospec1.4 spectrograph equipped with an Andor CCD system. Raman spectra were processed using Kasier Optical Systems Holospec software. Spectra were collected with a 20 second exposure time and accumulating 10 exposure with equivalent dark subtraction, Raman spectra were processed by dividing by the spectrum of a white light source, baseline correction using a cubic spline fit, and normalized using SNV normalization.

Wide Angie X-Ray Diffraction (WAXD)

Wide angle X-ray diffraction profiles were measured using a Bruker D8 XRD with a Cu tube source at 40 kV and 40 mA producing a 1.5418 Å X-ray beam. The scattered X-rays were detected utilizing the LYNXEYE_XE detector in OD mode. WAXD profiles were, recorded in a 2θ range of 10 to 25 degrees or 10 to 30 degrees with a 0.025 2θ increment and each point collected for 1 second. Data collection was cycled and co-added until reasonable signal to noise level was achieved. The polymer film was measured in the mechanical stretcher with the X-ray beam perpendicular to the strain direction.

Results and Discussion

Characterization of the beta form in PHA's is some that am area of controversy. Though the beta form is typically discussed as a crystal form of the polymer, it is not a true crystal form but rather a metastable partial packing of polymer chains with the same conformation. Thus, the structure of the unit cell is unknown and the lattice parameters are undefined, save c (fiber period)=0.470 nm, Conversely, the alpha crystal form displays an α(020) peak at 2θ=13.3°, α(110) peak at 2θ=16.7°, and an α(101) peak at 2θ=21.1°. The alpha peak d-spacing results in an overlap between the alpha and beta forms when studied in using XRD. This, overlap makes diffraction studies to confirm the presence of beta form ambiguous at times, especially with one-dimensional WAXD. Because there is a difference in the conformation of the polymer chain in the alpha versus the beta form, IR and Raman spectroscopy should be used as comparative analysis methods with diffraction studies for confirming the presence of beta form. The backbone region of the spectrum has several vibrational modes from the C—O—C and C—O stretching in the polymer chain that change in vibrational frequency between the two phases. However, because of the simplicity of studying a single band, some prefer to observe the carbonyl peak to determine beta content, as is performed for alpha versus amorphous content of the polymer. The issue is that the position of the beta carbonyl peak is still up for debate. Some groups report a vibrational frequency around 1730 cm$^{-1}$, while others report 1740 cm$^{-1}$. The second peak position is the most problematic, for if it is true that the carbonyl vibrational mode is the same in the beta form as in the amorphous polymer, then any analysis of the beta content of a PHA sample using the carbonyl band could just as correctly be interpreted as an variation in the amorphous content of the polymer. With the goal of differentiating the position of the beta form carbonyl band, films of 13 mol % 3HHx PHBHx were generated with strain induced beta form for analysis using Raman, IR, and WAXD.

Figure 20:
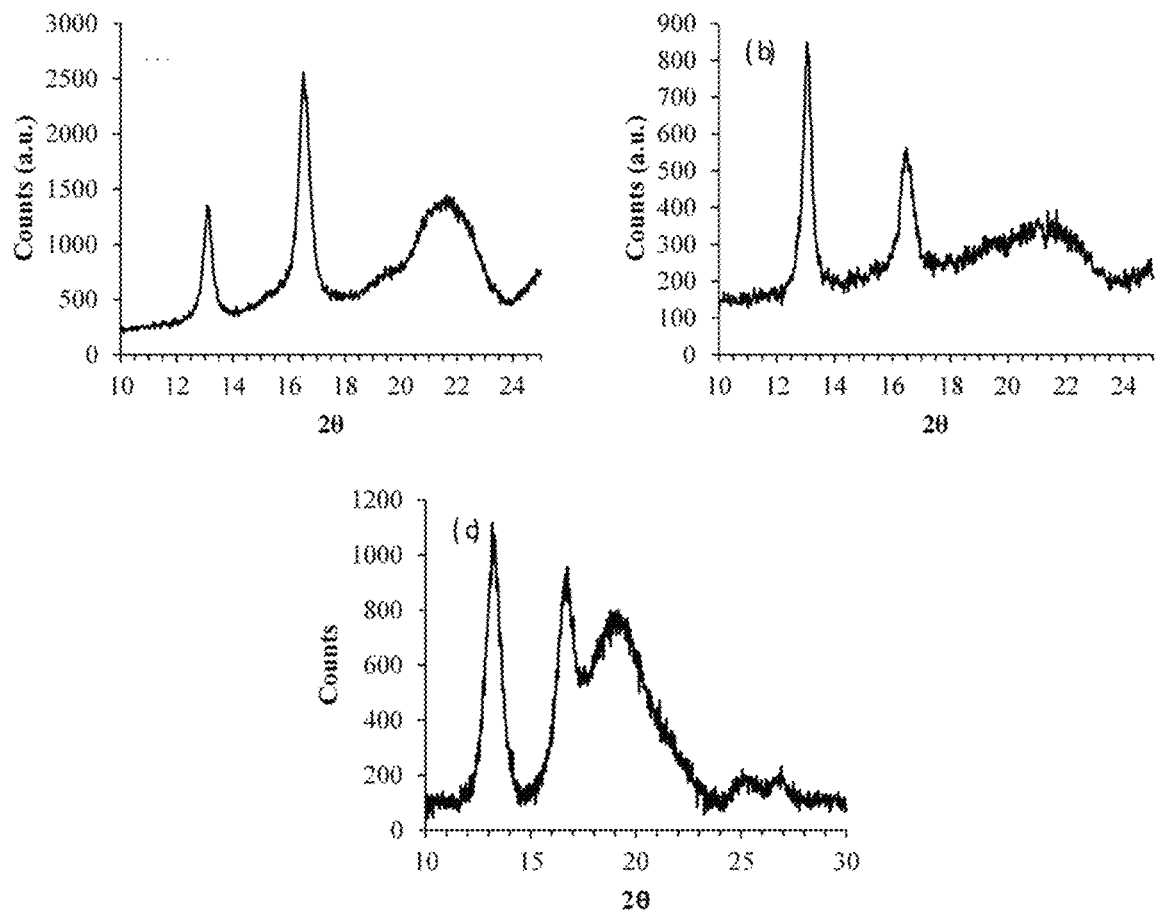
FIG. 20: WAXD profile of a eat, annealed 3.9 (a) and 13 (b) mol % 3HHx PHBHx films and stretched (C) 13 mol % 3HHx PHBHx film oriented with X-ray beam perpendicular to stretching direction.

Although, as was previously mentioned, XRD results can be ambiguous for determining the presence of beta form, it is still important to obtain a diffraction profile for comparison with the alpha form. Additionally, in highly oriented samples, the majority of the alpha diffraction peaks tend to go unobserved in one-dimensional diffraction studies, due to the crystal orientation in the sample. FIG. 20 contains the diffraction profile of neat 3.9 and 13 mol % 3HHx PHBHx polymer films after annealing and 13 mol % 3HHx PHBHx polymer film after strain was applied. The 3.9 mol % 3HHx PHBHx annealed film was included in the study to demonstrate the number of alpha crystal diffraction peaks for comparison to the stretched film.

3.9 mol % 3HHx PHBHx WAXD profile contains the three diffraction peaks listed previously, in addition to another alpha peak at ~19.5 2θ while the 13 mol % 3HHx PHBHx annealed film includes the alpha (020) and (110) peaks in addition to a broad peak centered at 21.5 2θ. The stretched film WAXD profile also contains the alpha (020) and (110) peaks, but shows an additional large, broad peak centered at 19.5 2θ. This broad diffraction peak is typical of a PHA sample containing beta form. Notice, however, that the higher 2θ diffraction peaks of the alpha crystal are nearly unobservable. The lack of diffraction from the other crystal planes is due to the high amount of orientation that was introduced into the sample during the two step stretching. Because the sample is oriented in the XRD with the stretching direction perpendicular to the X-ray beam, the alpha crystal lamella are oriented with the c axis parallel to the stretching direction. Additionally, the beta form is also oriented with the c axis parallel to the stretching direction. A comparison to the other diffraction profiles FIG. 20 illustrates the issue with using XRD to confirm the presence of the beta form. In the same position as the maximum of the beta peak is a diffraction peak arising from the alpha form, seen in the 3.9 mol % 3HHx PHBHx film. If a sample is oriented a certain way with respect to the X-ray beam path, this peak could increase in relative intensity and give the illusion of beta form, especially if the alpha crystals are small in diameter, which causes the diffraction peaks to broaden, Overall, these profiles strongly suggest that the beta form was produced in the stretched film, but further analysis was required.

Figure 21:
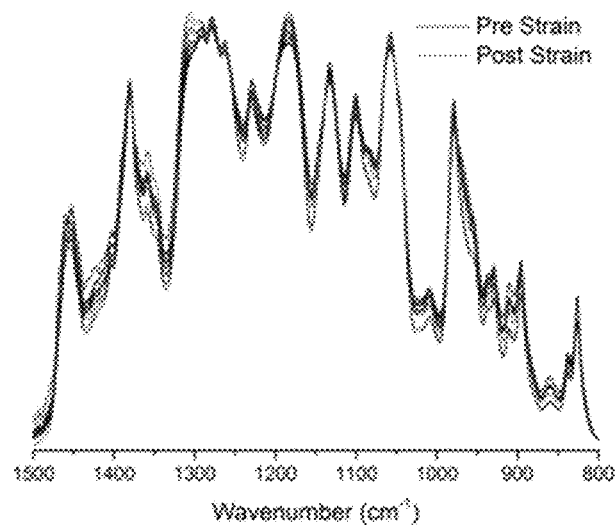
FIG. 21; IR spectra of neat 13 mol % 3HHx PHBHx polymer film as a function of increasing strain.

To confirm the presence of the beta form in the stretched films of 13 mol % 3HHx PHBHx, IR spectra were taken as the film was stretched at room temperature after the first strain was applied below Tg. These spectra only contain the backbone region because the films were too thick, causing over-absorbance of the carbonyl. Thinner samples were not mechanically stable enough for use in the mechanical stretching device. FIG. 21 contains the IR spectra of neat 13 mol % 3HHx PHBHx polymer film as a function of increasing strain.

Based on the presence and consistency of the bands at 1278, 1263, and 1228 cm$^{-1}$, all of which are assigned to the helical conformation, the polymer crystallized into, the alpha form before spectral collection began. Chaturvedi et al compared IR and FT-Raman spectra of PHB samples containing beta form to quantum chemical calculations of the vibrational dynamics of a linear zigzag PHB chain to determine the vibrational bands related to the beta form of the polymer. Their analysis yielded a large number of vibrational frequencies, some of which are not a function of the conformation of the polymer chain, but included the bands that are increasing in the IR spectra as a function of increasing strain. Specifically, the bands at 1305, 1142, 1080, 969, and 911 cm$^{-1}$ are all increasing in the spectra as the film is stretched. All of these vibrational modes are not attributed to either the amorphous or alpha crystal phases of PHB and were calculated for the beta conformation. With the results from the XRD, the IR spectra confirm that stretching PHBHx can induce beta form just as is observed with the homopolymer, despite the high 3HHx content of the sample.

Figure 22:
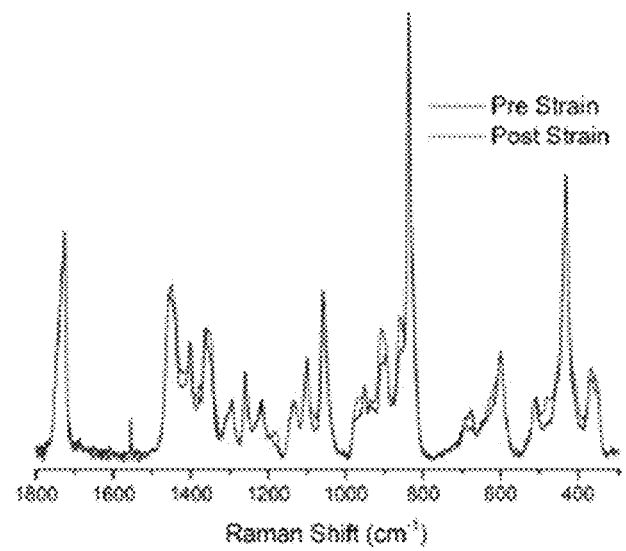
FIG. 22: Raman spectra of neat 13 mol % 3HHx PHBHx polymer film before and after strain.
Figure 23:
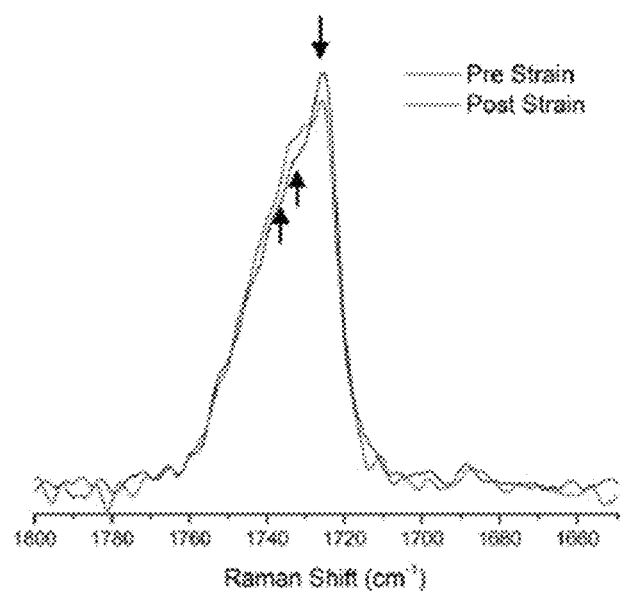
FIG. 23: Raman spectra of neat 13 mol % 3HHx PHBHx polymer film before and after strain focused on the carbonyl region.

Although the XRD and IR, analyses have revealed that beta form can be generated in PHBHx films when strain is applied, the limitations imposed on the IR measurements by the thickness of the sample made observation of the carbonyl impossible. The carbonyl is greatly affected by its local environment and is often used to determine the presence of amorphous and alpha crystalline phases in PHA'S. Specifically, the alpha crystal IR band is centered at 1720 cm$^{-1}$ and the amorphous band is centered at 1740 cm$^{-1}$. For this reason, Raman spectra were also collected for the stretched films. Raman spectroscopy does not measure the absorption of light like IR spectroscopy, but rather what is known as Raman scattering of a material. When the light from a laser in a Raman spectrometer interacts with a sample the photons can couple with a vibrational mode of a functional group of the sample. The energy difference between the photon before and after this coupling corresponds to the energy difference between two resonant states of the material. Plotting intensity of the scattered light as a function of the frequency difference between the scattered and the incident photon forms the Raman spectrum. Therefore, because this method does not require the light to pass through the sample, intense peaks cannot over-absorb due to sample thickness. Additionally, the stretching vibrational mode of the carbonyl is much weaker in the Raman compared to the IR, because the IR is more sensitive to changes in dipole moment while the Raman is more sensitive to changes in the polarizability. FIG. 22 contains the Raman spectra of neat 13 mol % 3HHx PHBHx polymer film before and after strain.

Because the photons in Raman and IR spectra interact differently with the sample, the spectrum appears somewhat different compared to those in FIG. 21. However, the vibrational frequency of the bands should not vary between the methods. With that in mind, the variation in the spectra with increasing strain is very similar to those in the IR. Specifically, the bands at 1451, 1379, 1354, 1177, 1080, 966, 908, 858, 627, 478, and 454 cm$^{-1}$ all increase as strain is applied to the polymer film. These vibrational bands are all attributed to the beta conformation of the polymer and help to reinforce the results of the XRD and the IR analyses. To better observe the carbonyl peak in the Raman, FIG. 22 shows the scale expanded spectra of neat 13 mol % 3HHx PHBHx polymer film before and after strain focused on the carbonyl region.

It would appear that as strain is applied to the film there is an exchange between the alpha crystal peak and the amorphous peak, with another peak in between. The alpha crystal band decreases in intensity, while this new band and the amorphous peak increase. The position of the new peak is around 1730 cm$^{-1}$ which is the same position that was reported Chaturvedi et al for the beta form conformation. These results strongly suggest that the correct position for the beta carbonyl peak is 1730 cm$^{-1}$ and not 1740 cm$^{-1}$. However, due to the weakness of the Raman scattering of the carbonyl function group, there is a large amount of noise in the spectra, making the new band difficult to resolve. Further work is required in this area to produce better spectra as a function of percent strain. Ultimately, a more in-depth analysis utilizing a tool such as 2DCOS should be applied to such data sets to not only determine the carbonyl band for the beta form, but also to analyze the process through which beta is generated when the polymer is stretched.

Example 5: Mechanical Stretching of Films for the Formation of, β-form of Poly((R)-3-hydroxybutyrate-co-(R)-3-hydroxyhexanoate) (PHBHx)

Experimental Procedure

Solutions of 10 weight percent PHBHx in chloroform were made. The Hx content of the PHBHx was 13 mole percent. Then, films were cast at room temperature onto glass slides, with 2.5 mL of solution being used for each film. These films were dried at room temperature for a minimum of an hour and then placed in a vacuum chamber overnight.

After spending the night vacuum chamber, the films were placed on Teflon blocks and melted in an oven at 140° C. for 20 minutes. Immediately after being removed from the oven, the films were quenched into ice water and transferred to a freezer. These films were shown by the ATR FTIR and XRD measurements to be amorphous.

Figure 24:
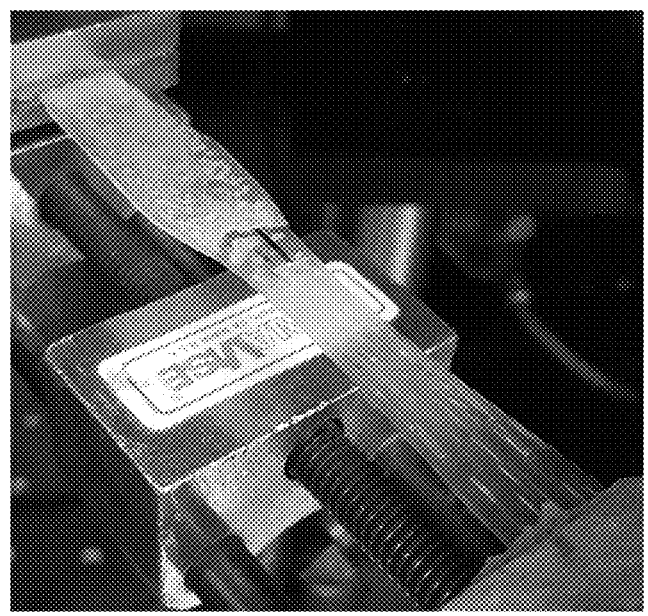
FIG. 24: Stretched film showing unstretched s and stretched regions.

Next, the films were brought out of the freezer and left at room temperature for the desired amount of time. The films were then stretched at room temperature, as shown in FIG. 24, and subsequently analyzed.

Results and Discussion

Planar Zigzag Formation

The planar zigzag conformation of PHBHx was successfully formed via isothermal crystallization at room temperature followed by a one-step stretch at room temperature. The stretched films consistently behaved in the same way when forming the β conformation. The majority of the film would not stretch and remained stationary. This section of the film does not result in formation of the β conformation. A section of the film adjacent to the stretcher clamp would elongate and form a distinct clear region, a process called "necking". This stretched region is where the β conformation is formed. Initially, the β region of the film tended to break at low elongation amounts. To alleviate this, tape was attached to the ends of the films before being put into the stretcher. This reduces the direct contact between the film and the clamp allowing the film to be stretched farther before breaking.

Figure 25:
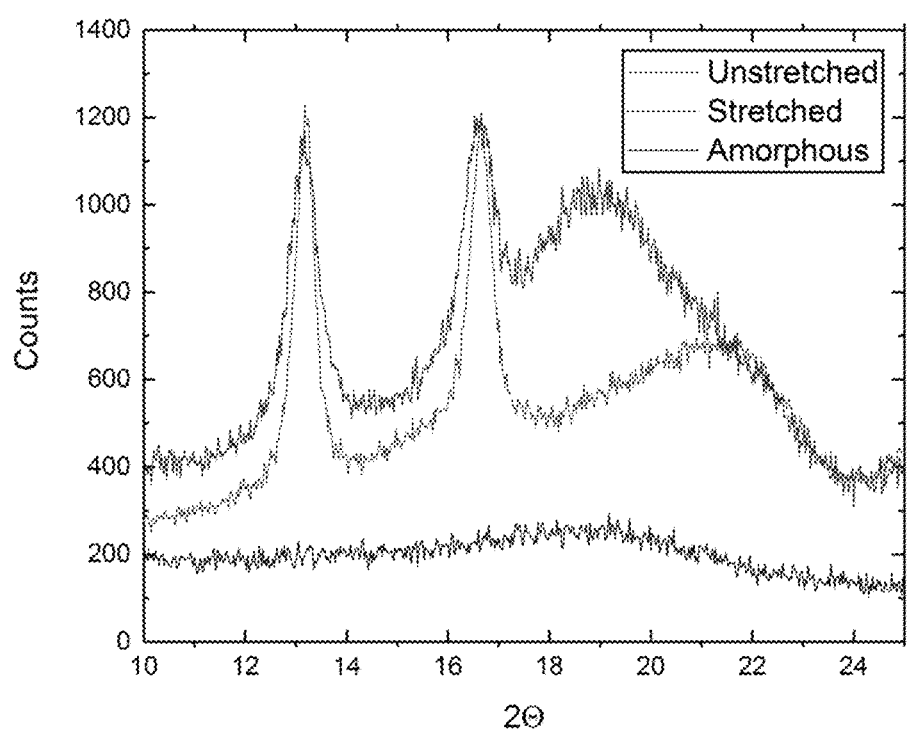
FIG. 25: XRD of amorphous, unstretched a region, and stretched β region of same film.
Figure 26:
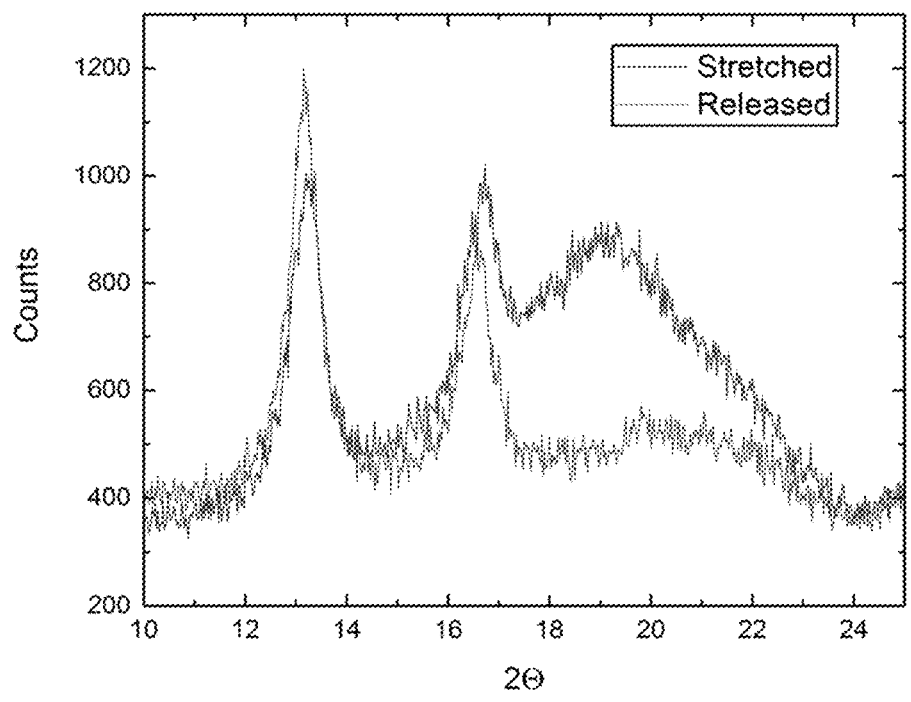
FIG. 26: XRD spectrum of a film after stretching and being released

The conformation was confirmed using XRD and Raman spectra. In the XRD spectrum, the peaks at 2θ values of 13 and 16 correspond to, the α crystal planes of 020 and 110, respectively. The apparent peak at a 2θ value of 22.5 is actually an overlap of 3 peaks from the a crystal structure. The peak at 19.2 arises from the existence of the planar zigzag conformation[7,8]. FIG. 25 shows the XRD spectra for the unstretched and stretched portions, respectively, of the same film. It can be clearly seen that the mechanical strain causes the β conformation to form. Additionally, the size of the α crystals in the stretched area of the film are smaller than the size of the α crystals in the unstretched area. In the stretched area of the films, the average alpha crystalline domain size was 21.3 nm far the 020 plane and 20.4 nm for the 110 plane. All crystalline domain sizes are calculated using the Scherrer equation with a K value of unity. This suggests that the formation of the planar zigzag conformation also brings a decrease in the size of the α crystals. Such results have been seen in other PHAs as well.

The size of the crystals formed via this procedure are small, as seen by the broad peak corresponding to the β structure. Quantitatively, the β crystalline domains average 3.8 nm in size. This raises questions as to whether true β crystals are being formed. It is possible that instead of true crystals, this procedure leads to the formation of an ordered planar zigzag phase which has too few aligned chains to form a crystal. This could be due to the lack of alignment in the amorphous prior to crystallization and formation of the α crystallites.

Planar Zigzag Reversibility

Figure 27:
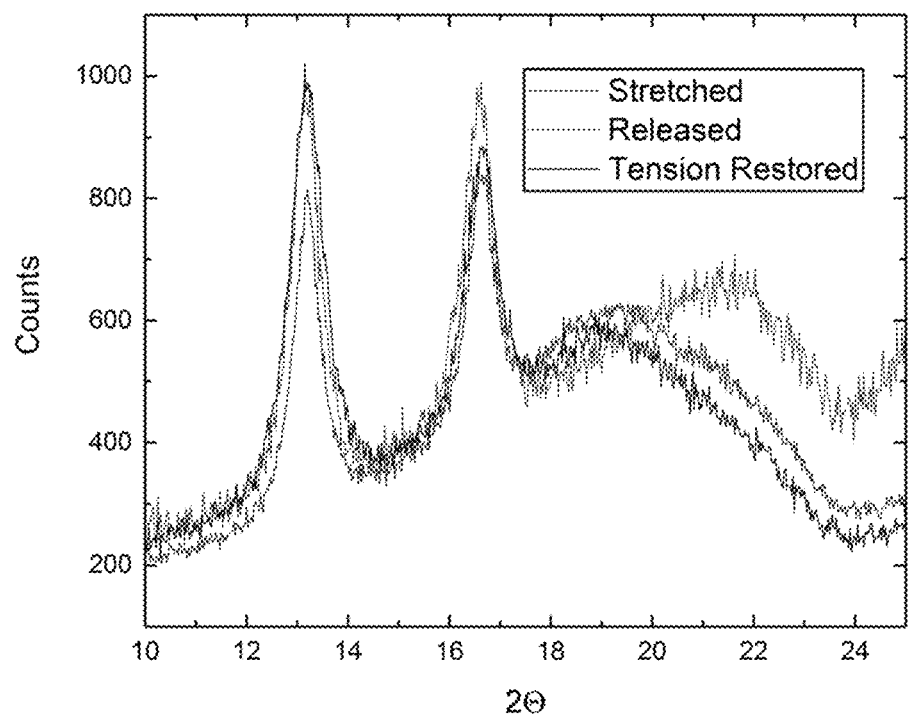
FIG. 27; XRD spectrum of film after being stretched, released, and had tension restored.

After being stretched at room temperature and fort forming the planar zigzag conformation, films that are then released the from the mechanical stress do not maintain the planar zigzag conformation. Only α crystals remain after the tension is released. However, upon restoration of the tension, the β conformation returns. This effect can be seen in FIG. 27 in a film that has been stretched, released, and had tension immediately restored, respectively. In addition to the XRD spectrum, a Raman spectrum of the released film was obtained to be sure that the β conformation had disappeared.

Figure 28:
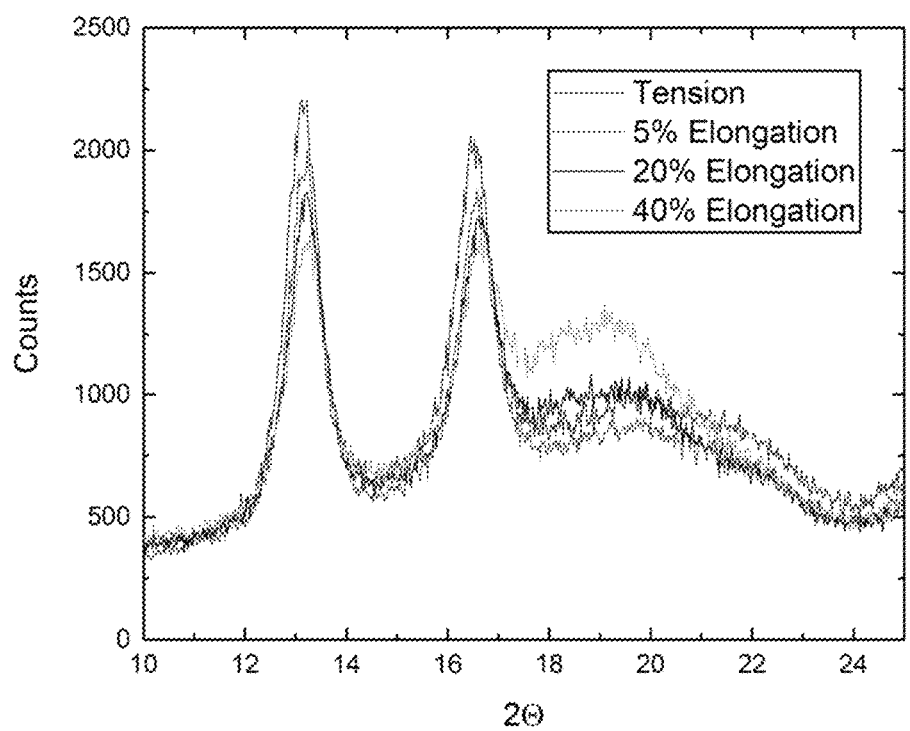
FIG. 28 XRD as a function of strain.

This was not the case when re-stretching the released films that had been left at room temperature for 24 hours. As seen in FIG. 28, the β content gradually increased as the elongation increased. Due to the increased crystallization, when the film was re-stretched, the necked area continued to stretch more and more as the film was elongated. The surrounding non-necked regions were too crystalline and rigid to become necked, so the already necked region continued to elongate. It can be seen that the peaks associated with the α crystal structure decrease in size before the peak associated with the β structure increase. The size of the α crystalline domains also seems to decrease slightly, although this is less prominent than the overall decrease in the height of the peaks. This shows that when the film is, re-stretched the α crystals melt first into an intermediate state and then form the β structure.

It is Clear that the β Conformation Did Not Remain After Tension was Released.

Figure 29:
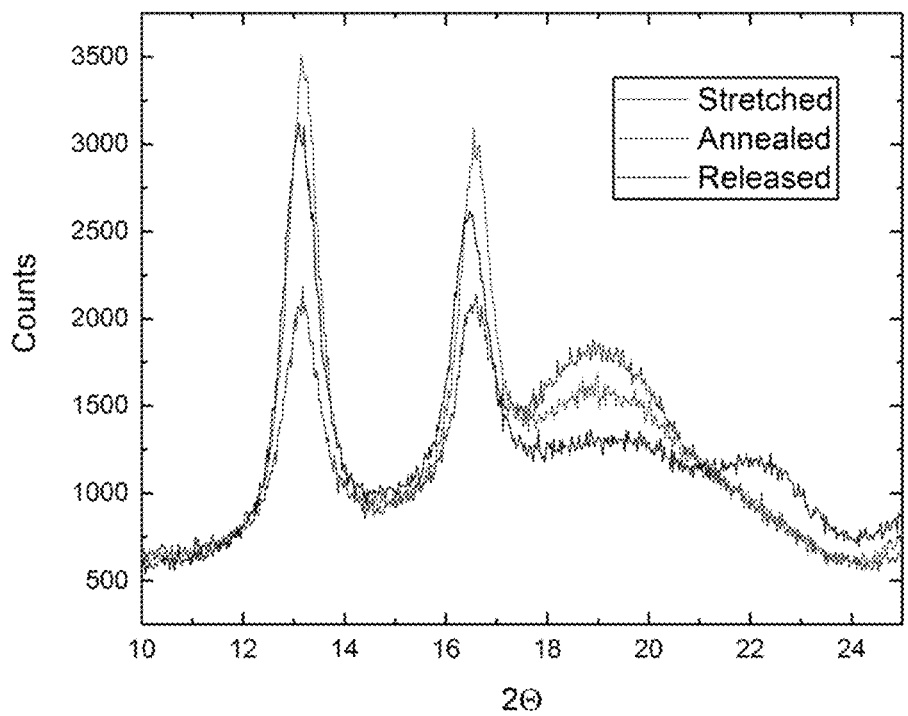
FIG. 29: XRD spectrum of stretched film annealed for 2 hours at 48° C.

Additional annealing was done at 48° C. for 2 hours. An XRD spectrum of this film is shown in FIG. 29. The α content of the stretched film increases significantly as a result of this treatment. Additionally, the amount of β conformation decreased as a result of the annealing. Upon being released, it seems that a small amount of β conformation may remain. However, this film was taped to the XRD sample holder, and it is possible that this process put slight tension on the film, restoring the β conformation.

Figure 30:
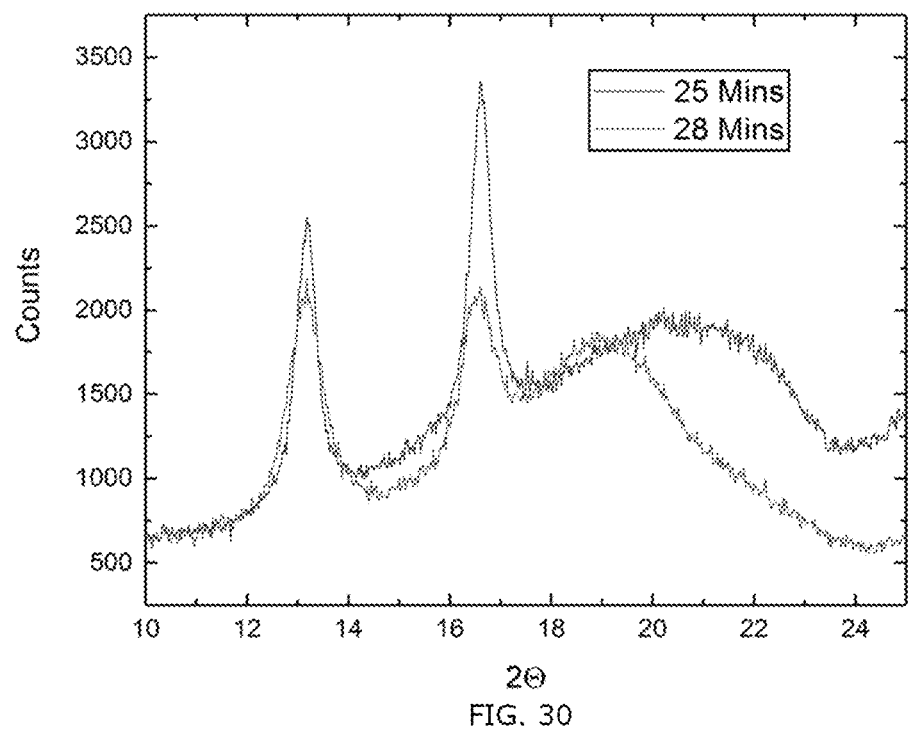
FIG. 30: XRD spectrum of stretched films after isothermal crystallization at room temperature
Figure 31:
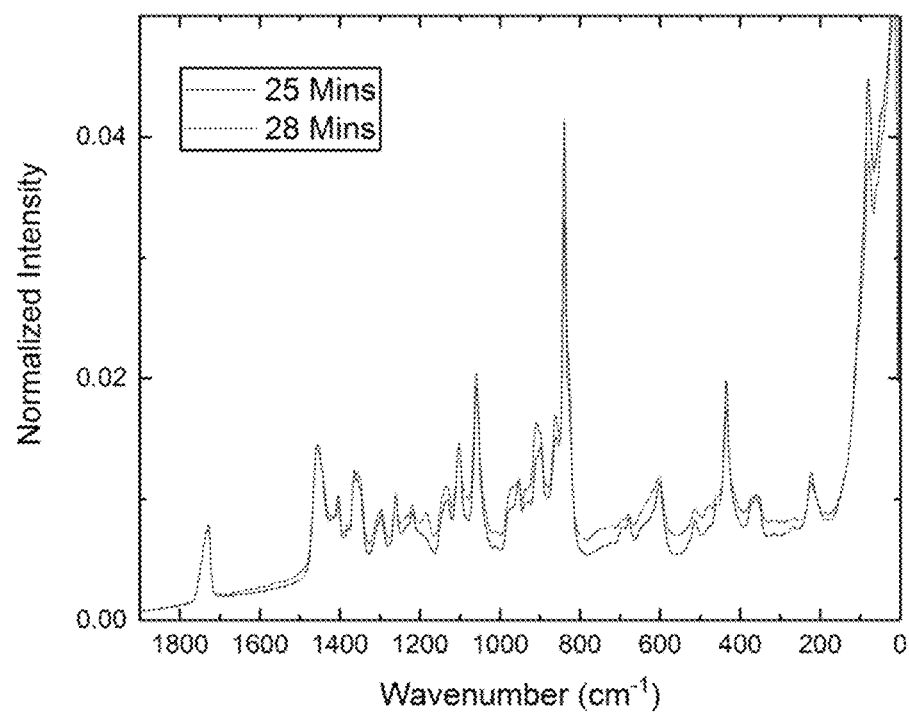
FIG. 31: Raman spectrum of retched films after isothermal crystallization at room temperature.

To optimize the formation of the conformation, films were left to isothermally crystallize for differing amounts of time before being stretched. Films were stretched after 25, 28, 30, 35, and 40 minutes. When stretched after 25 minutes of crystallization, the entire film elongated over 200% without signs of breaking. The stretched films after 25 and 28 minutes of crystallization were analyzed using XRD and Raman, seen in FIGS. 30 and 31, respectively.

The above spectra show that the film stretched after 25 minutes of crystallization did not form any β conformation, while the film stretched after 28 minutes did form a large amount of the β conformation.

It has been shown in this example that isothermal crystallization of 13 mole percent Hx in PHBHx films at room temperature can form the β conformation using a single stretch. However, the XRD peak for this conformation is broad, and it is unclear whether this β conformation is in the form of very small crystals or a noncrystalline ordered phase.

Capturing XRD and Raman spectra as a function of time while the films are annealed at different temperatures would give insight into these changes and ways to lock in the β conformation after tension is released.

Additionally, the example disclosed herein is for PHBHx with an Hx content of 13 mole percent. This is a high amount of Hx monomer, and many compositions of PHBHx are available that have lower Hx content. These polymers behave differently from the 13 mole percent PHBHx, and a parallel study of each of these PHBHx compositions would generate interesting results concerning the relationship between the Hx content and formation of the β conformation.

Conclusion

The β conformation of PHBHx has been shown to be formed in 13 mol % Fix content PHBHx films via a novel method of room temperature isothermal crystallization followed by mechanical stretching. A distinct stretching region of the film was seen after 28 minutes of crystallization which resulted in large sections of the film forming the β conformation. Stretching earlier than this does not result in any β formation, and stretching after this results in a rigid film that does not form as large a section of β conformation and is prone to breaking. Through XRD and Raman analysis, it was confirmed that α crystals must be present prior to stretching in order to form the β conformation, and that the size of the α crystals decreases during this process. This agrees with the formation mechanism suggested by previous literature involving α crystal tie points.

The β conformation was shown to be reversible and the stretching process is different for the initial β formation and the re-stretching process. In the initial formation process, the β forms immediately and does not change as a function of elongation. Rather, more of the film is converted into the β conformation as elongation increases. After being released, β conformation disappears. If the film is left at room temperature for 24 hours and re-stretched, the β conformation forms gradually as a function of elongation due to the fact that the rest of the film is rigid, and only the previously stretched section can elongate. However, in the stretched section of the film, the α content does not drastically increase, while the unstretched section of the film undergoes a drastic increase in a content.

The β conformation could also be annealed back into the a conformation at temperatures as low as 48° C., but interestingly the size of the α crystals did not increase. Therefore, the number of α crystals must be increasing during this process while not changing size.

With the β conformation of PHBHx being easily formed in films under readily accessible conditions, its future development into commercial products is promising. Through additional investigation, the potential of this biodegradable, biocompatible, durable, and piezoelectric material for novel products can be realized.

Figure 32:
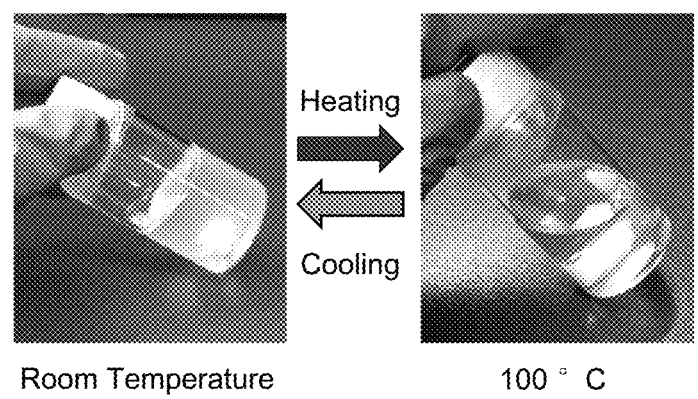
FIG. 32: Thermally reversible sol-gel transition PHBHx $CHCl_3$/DMF solution.
Figure 33:
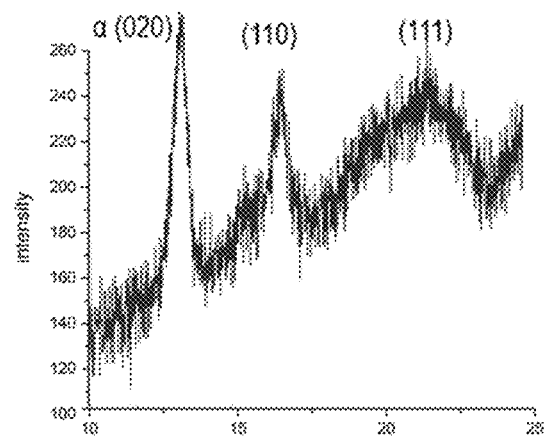
FIG. 33 WAXD profiles of (a) raw PHBHx powder and (b) freeze-dried gel.
Figure 33:
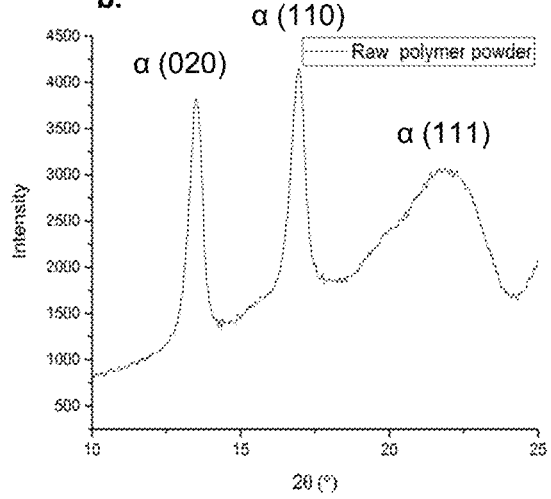

Example 6: Stretching for the Formation of β-form of Poly((R)-3-hydroxybutyrate-co-(R)-3-hydroxyhexanoate) (PHBHx) in Gel Films A thermally reversible sol-gel transition was observed in PHBHx in $CHCl_3$/DMF or $CHCl_3$/1,4-dioxane solutions, PHBHx was dissolved in $CHCl_3$/DMF or $CHCl_3$/1,4-dioxane binary solvent, system at elevated temperatures (100° C.) under stirring, where $CHCl_3$ is recognized as a good solvent for PHBHx while DMF and 1,4-dioxane are poor solvents for PHBHx at room temperature. The clear PHBHx solution, slowly cooled to room temperature (c.a. 20° C.), yielded an opalescent gel. As seen in FIG. 32, a sol-gel transition occurs as the temperature was raised from room temperature to 100°, and this transition was found to be reversible.

Figure 34:
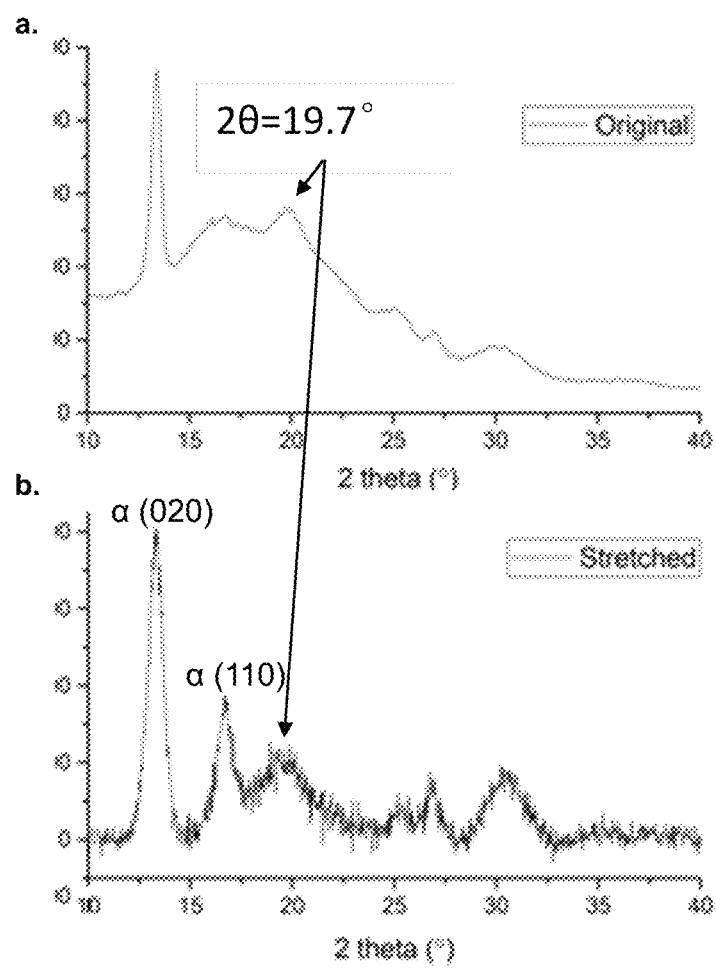
FIG. 34: WAXD profiles of the gel film (a) before and (b) after stretching.
Figure 35:
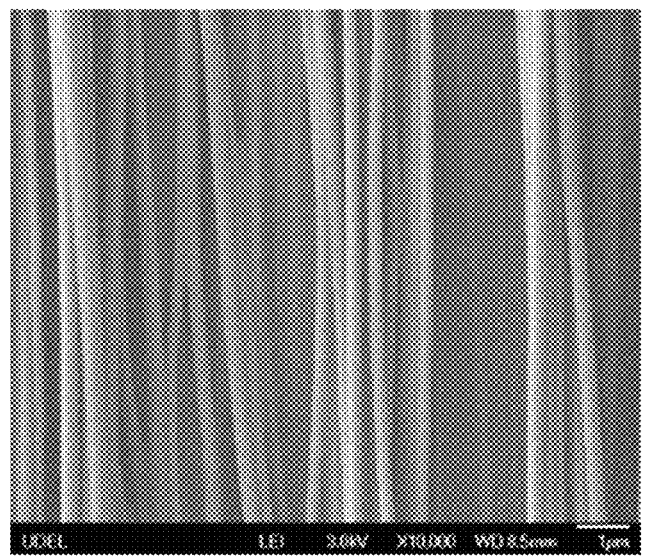
FIG. 35: Scanning Electron Microscope image of PHBHx 3.9 mol % electrospun nanofibers collected on a rotating wheel 3500 rpm) and shown to beta crystalline form by wide angle x-ray scattering.
Figure 36:
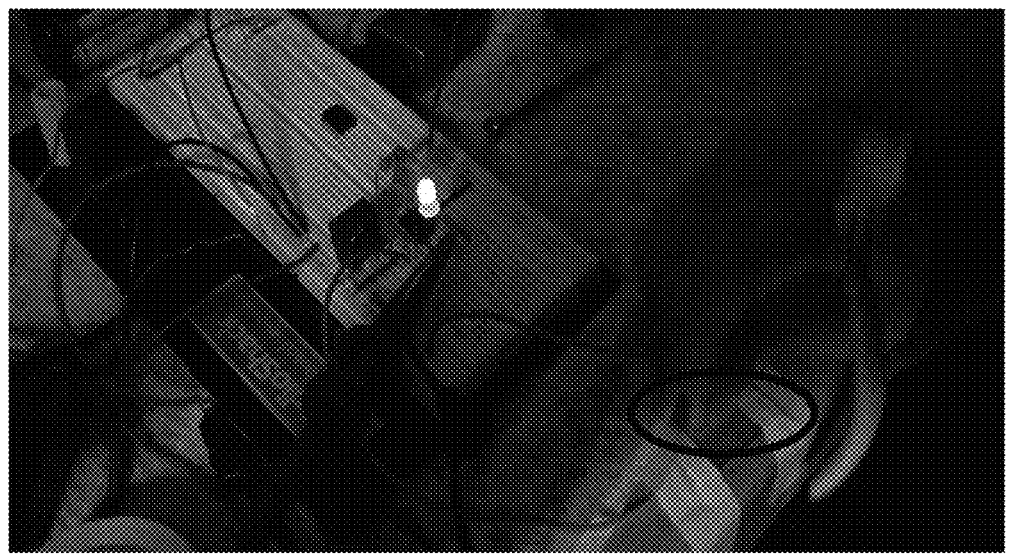
FIG. 36: The aligned PHBHx 3.9 mol % nanofibers of FIG. 35, as part of an electrical circuit (see red oval) and deformed by handle of pliers to produce a voltage to light up LED bulb.

Thin films of the thermoreversible gel were produced by smearing the gel onto a glass slide and subsequently drying the wet smeared gel under ambient conditions. After the solvent evaporated, clear and smooth gel films were obtained. Again, the crystal structure of the gel films was characterized with WAXD and found that the diffraction profile obtained was very different from those of raw PHBHx powder and freeze-dried gel plotted in FIG. 31. In FIG. 34a it should be noted that the α (111) peak (2θ=22°) disappeared, and the α (110) peak became broad and weakened. Meanwhile, a new diffraction peak at 2θ=19.7° appeared. This new peak is very similar to the β-form diffraction peak observed in the WAXD profile of the rotary disk aligned fibers in terms of peak position and peak width (FWHM). More interestingly, the WAXD profile of the stretched gel film (FIG. 34b) shows an increase of the relative intensity of this new peak as well as the reappearance of the a (110) peak. These observations indicate that β-form crystallites may exist in the gel film, and the stretching of the gel film facilitates the development of both the α and β-crystalline structures. The recrystallization of the kinetically frozen molecular chains in the gel film during stretching caused an enthalpy change in the system, which may explain the massive heat observed physically when stretching the gel film.

These preliminary results show the appearance of the β-crystalline structure in the gel film, which indicates that it might be possible to massively produce PHBHx thin films with a large concentration of β-crystals. These β-form-rich PHBHx thin films may find many new applications, which never were β-form crystalline observed for α-PHBHx.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

Example 7: Method of Making Poled PHA Copolymer Based Articles

Five parts of PHBHx3.9 powder are dissolved in 95 parts chloroform ($CHCl_3$) at 100-125 degrees centigrade and the solution is transferred to a tray and put in a vacuum oven. Oven is maintained at 10-3 torr and a temperature range within 120-140 degrees C. until a PHBHx solution is obtained having approximately 80% PHBHx3.9 by weight and 20% DMF by weight. The PHBHx3.9 solution is transferred as a film to a press subjected to a pressure of 3000 PSI and heated to various temperatures ranging from 95-125° C. The film is then rapidly cooled in an ice bath. The film is then transferred to a poling apparatus consisting of two polished copper plates, which are in turn connected to a high voltage DC power supply. The temperature of the film is raised to slightly above the melting point and the film is poled. In one embodiment, during the poling, the temperature is decreased linearly at 24° C./min to 30° C./min and the poling field I increased linearly from 25 KV/cm to 1000 KV/cm. At room temperature the poling field is reduced to zero.

What is claimed:

1. A process for preparing a polarized material comprising the steps of:
   a) forming a film or sheet of a polarizable polymeric composition, wherein the polarizable polymeric composition comprises a polyhydroxyalkanoate (PHA) based copolymer;
   b) directionally perturbing the film or sheet to induce polarization to form a polarized polymeric composition by at least one of:
   (i) subjecting the film or sheet cast from solution to calendar rolling,
   (ii) subjecting the film or sheet cast from a solution to melt crystallization under shear or pressure,
   (iii) mechanically stretching the film or sheet formed from the polarizable polymeric composition in a gel state,
   (iv) freezing the polarizable polymeric composition in a gel state to induce shear by crystallization,
   (v) applying shear or pressure during molding of the film or sheet, or
   (vi) applying electrical field during molding of the film or sheet from the polarizable polymeric composition in a melt state;
   wherein the polarized polymeric composition comprises a β-form of the PHA based copolymer, present in an amount from about 10% to about 99%, as measured by x-ray diffraction.

2. The process of claim 1 wherein the step of forming a film or sheet comprises forming a film or sheet from a solution of the polyhydroxyalkanoate based copolymer in one or more solvents by casting.

3. The process of claim 1 wherein the step of forming a film or sheet comprises forming the film or sheet from a melted composition of the polyhydroxyalkanoate based copolymer.

4. The process of claim 3, wherein the step of directionally perturbing the film or sheet comprises calendar rolling, shearing or cold drawing the film or sheet after quenching.

5. The process of claim 1 wherein the step of forming a film or sheet comprises forming a film from a gel composition of the polyhydroxyalkanoate based copolymer.

6. The process of claim 5, wherein the step of directionally perturbing the film comprises drying the gel under shear pressure or freezing gel to induce shear by crystallization of solvent.

7. The process of claim 1 wherein the polyhydroxyalkanoate based copolymer comprises at least one monomer unit selected from the group consisting of hydroxybutyrate units, hydroxyhexanoate units, vinyl units, vinylidene units, ethylene units, acrylate units, methacrylate units, Nylon units, carbonate units, acrylonitrile units, cellulose units, units having pendant fluoro, chloro, amide, ester other than ester of acrylate and methacrylate units, cyanide, nitrile other than of acrylonitrile units, or ether groups, protein units and combinations thereof.

8. The process of claim 1 wherein the polarizable polymeric composition further comprises one or more polymers selected from the group consisting of polyvinylchloride, polymethylacrylate, polymethylmethacrylate, poly(vinylidene cyanide/vinyl acetate) copolymers, vinylidene cyanide/vinyl benzoate copolymers, vinylidene cyanide/isobutylene copolymers, vinylidene cyanide/methyl methacrylate copolymers, vinylidene fluoride copolymer, polyvinylfluoride, polyacrylonitrile, polycarbonate, cellulose, proteins, synthetic polyesters and ethers of cellulose, poly(gamma-methyl-Lglutamate), vinylidene copolymers, Nylon-3, Nylon-5, Nylon-7, Nylon-9, Nylon-11 and blends thereof.

9. The process of claim 1, further comprising polarizing the polarizable polymeric composition or polarized polymeric composition of the film or sheet by applying the electric field of at least 1 MV/cm at a temperature from about 20° C. to about 120° C. for up to about 5 hours.

10. The process of claim 1, further comprising annealing the polarized polymeric composition of the film or sheet at a temperature in a range of from about 125° C. to about 150° C. for at least one hour, wherein the temperature is less than a melting temperature of crystals of the polarized polymeric composition, and whereby the polarization is retained up to the melting temperature of crystals of the polarized polymeric composition.

11. The process of claim 1,
wherein the film or sheet is configured to monitor one of the following properties, humidity, temperature, salinity, nutrient attachment or infusion and metalloid attachment;
wherein upon exposing the film or sheet to one or more of the said properties the film or sheet undergo a change in dimension caused by a change in one or more of the said properties; and
whereby a potential difference or voltage is detected in response to a change in dimension of the film or sheet.

12. A process for preparing a polarized material comprising the steps of:
a) forming a film or sheet of a polarizable polymeric composition, wherein the polarizable polymeric composition comprises at least one of:
   i. a polymer blend of two or more poly[(R)-3-hydroxybutyrate-co-(R)-3-hydroxyhexanoate] (PHBHx) copolymers, each of the two or more PHBHx copolymers having a different comonomer content,
   ii. a PHA based copolymer with longer side chain selected from poly(3-hydroxybutyrate-co-3-hydroxyoctanoate) (PHBO) with pentyl side group, poly(3-hydroxybutyrate-co-3-hydroxydecanoate) (PHBD) with heptyl side group, PHBO or PHBD with C15 side group chains, and medium-chain-length branched polyhydroxyalkanoates (mcl-PHA),
   iii. a polymer blend of a copolymer of PHBHx and one or more PHA based copolymer with longer side chain, and
   iv. a polymer blend comprising polyhydroxyalkanoate (PHA) based copolymer and one or more polymers selected from the group consisting of polyvinylchloride, polymethylacrylate, polymethylmethacrylate, poly(vinylidene cyanide/vinyl acetate) copolymers, vinylidene cyanide/vinyl benzoate copolymers, vinylidene cyanide/isobutylene copolymers, vinylidene cyanide/methyl methacrylate copolymers, vinylidene fluoride copolymer, polyvinylfluoride, polyacrylonitrile, polycarbonate, cellulose, proteins, synthetic polyesters and ethers of cellulose, poly(gamma-methyl-L-glutamate), vinylidene copolymers, Nylon-3, Nylon-5, Nylon-7, Nylon-9, Nylon-11 and blends thereof; and
b) directionally perturbing the film or sheet to induce polarization to form a polarized polymeric composition by at least one of:
   (i) subjecting the film or sheet cast from solution to calendar rolling,
   (ii) subjecting the film or sheet cast from a solution to melt crystallization under shear or pressure,
   (iii) mechanically stretching the film or sheet formed from the polarizable polymeric composition in a gel state,
   (iv) freezing the polarizable polymeric composition in a gel state to induce shear by crystallization,
   (v) applying shear or pressure during molding of the film or sheet,
   (vi) applying electrical field during molding of the film or sheet from the polarizable polymeric composition in a melt state, or
   (vii) in situ polarization during step of forming a film or sheet by electrospinning a ribbon of fibers from a solution of the polarizable polymeric composition in one or more solvents, wherein each fiber of the electrospun ribbon of fibers comprises a shell formed of $\beta$-form and a core formed of $\alpha$-form;
c) optionally polarizing the polarizable polymeric composition of the directionally perturbed film or sheet by applying a high electric field which is of less intensity than that which would cause substantial dielectric breakdown of the PHA based copolymer; and
d) optionally annealing the polarized polymeric composition of the film or sheet at a temperature less than a melting temperature of crystals of the polarized polymeric composition, whereby polarization is retained up to the melting temperature of crystals of the polarized polymeric composition, wherein the polarized polymeric composition comprises a $\beta$-form of the PHA based copolymer, present in an amount from 10% to 99%, as measured by x-ray diffraction.

13. The process of claim 12,
wherein the film or sheet is configured to monitor one of the following properties, humidity, temperature, salinity, nutrient attachment or infusion and metalloid attachment;
wherein upon exposing the film or sheet to one or more of the said properties the film or sheet undergo a change in dimension caused by a change in one or more of the said properties; and
whereby a potential difference or voltage is detected in response to a change in dimension of the film or sheet.

* * * * *